US010861584B2

(12) United States Patent
Sharma et al.

(10) Patent No.: US 10,861,584 B2
(45) Date of Patent: Dec. 8, 2020

(54) ANTIBODY SELECTION APPARATUS AND METHODS

(71) Applicant: Genentech, Inc., South San Francisco, CA (US)

(72) Inventors: Vikas K. Sharma, Millbrae, CA (US); Trevor E. Swartz, San Carlos, CA (US); Thomas W. Patapoff, San Carlos, CA (US)

(73) Assignee: GENENTECH, INC., South San Francisco, CA (US)

( * ) Notice: Subject to any disclaimer, the term of this patent is extended or adjusted under 35 U.S.C. 154(b) by 519 days.

(21) Appl. No.: 15/166,939

(22) Filed: May 27, 2016

(65) Prior Publication Data

US 2017/0091377 A1   Mar. 30, 2017

Related U.S. Application Data

(63) Continuation of application No. PCT/US2014/067580, filed on Nov. 26, 2014.

(60) Provisional application No. 61/910,200, filed on Nov. 29, 2013.

(51) Int. Cl.
| | |
|---|---|
| *G16B 15/00* | (2019.01) |
| *G16B 35/00* | (2019.01) |
| *G16C 20/60* | (2019.01) |
| *C07K 16/00* | (2006.01) |
| *G01N 33/531* | (2006.01) |

(52) U.S. Cl.
CPC ............ *G16B 15/00* (2019.02); *C07K 16/00* (2013.01); *G01N 33/531* (2013.01); *G16B 35/00* (2019.02); *G16C 20/60* (2019.02); *C07K 2317/10* (2013.01)

(58) Field of Classification Search
None
See application file for complete search history.

(56) References Cited

U.S. PATENT DOCUMENTS

| | | | |
|---|---|---|---|
| 6,172,213 B1 | 1/2001 | Lowman et al. | |
| 2016/0132634 A1* | 5/2016 | Trout ................ | G01N 33/6803 702/19 |

FOREIGN PATENT DOCUMENTS

| | | |
|---|---|---|
| EP | 2006381 | 12/2008 |
| EP | 2196541 | 6/2010 |
| WO | 2004039337 | 5/2004 |
| WO | 2014186692 | 11/2014 |

OTHER PUBLICATIONS

Kanai et al Database Caplus, 2006:864513 (Abstracts of Papers, 232nd ACS National Meeting, San Francisco, CA, United States, Sep. 10-14, 2006 ).*
Lauer et al. J Pharm Sci 101:102-115, 2012.*
Yadav et al. Pharm Res (2011) 28:1750-1764.*
Bailey, "The CCP4 Suite: Programs for Protein Crystallography" Acta Cryst. 50:760-763 (1994).
Bas et al., "Very Fast prediction and rationalizaiton of pKa values for protein-ligand complexes" Proteins 73:765-783 ( 2008).
Berendsen et al., "Molecular dynamics with coupling to an external bath" J. Chem. Phys. 81(8):3684-3690 (Oct. 15, 1984).
Boswell et al., "Effects of Charge on Antibody Tissue Distribution and Pharmacokinetics" Bioconjugate Chem. 21:2153-2163 ( 2010).
Bumbaca et al., "Physiochemical and Biochemical Factors Influencing the Pharmacokinetics of Antibody Therapeutics" The AAPS Journal 14(3):554-558 (Sep. 2012).
Bussi et al., "Canonical sampling through velocity rescaling" The Journal of Chemical Physics 126:014101-014101-7 ( 2007).
Cacia et al., "Isomerization of an Aspartic Acid Residue in the Complementarity-Determining Regions of a Recombinant Antibody to Human IgE: Identification and Effect on Binding Affinity" Biochemistry 35:1897-1903 ( 1996).
Chaudhri et al., "The Role of Amino Acid Sequence in the Self-Association of Therapeutic Monoclonal Antibodies: Insights from Coarse-Grained Modeling" The Journal of Physical Chemistry B 117(5): 1269-1279 (Feb. 7, 2013).
Chennamsetty et al., "Design of Therapeutic proteins with enhanced stability" PNAS 106(29):11937-11942 (Jul. 21, 2009).
Conolly et al., "Weak Interactions Govern the Viscosity of Concentrated Antibody Solutions: High-Throughput Analysis Using the Diffusion Interaction Parameter" Biophysical Journal 103:69-78 (Jul. 2012).
Darden et al., "Particle mesh Ewald: An N log(N) method for Ewald sums in large systems" J. Chem. Phys. 98(12):10089-10092 (Jun. 15, 1993).
Du et al., "Hydrophobic Salts Markedly Diminish Viscosity of Concentrated Protein Solutions" Biotechnology and Bioengineering 108(3):632-636 (Mar. 2011).
Eisenberg et al., "Hydrophobic Moments and Protein Structure" Faraday Symp. Chem. Soc. 17:109-120 ( 1982).
Eisenhaber et al., "The Double Cubic Lattice Method: Efficient Approaches to Numerical Integration of Surface Area and Volume and to Dot Surface Contouring of Molecular Assemblies" Journal of Computational Chemistry 16(3):273-284 ( 1995).
Gao et al., "In Silico Modeling of Nonspecific Binding to Human Liver Microsomes" Drug Metabolism & Disposition 36(10):2130-2135 ( 2008).
Hess et al., "GROMACS 4: Algorithms for Highly Efficient, Loas-Balanced, and Scalable Molecular Simulation" J. Chem. Theory Comput. 4:435-447 ( 2008).

(Continued)

Primary Examiner — Michael L Borin
(74) Attorney, Agent, or Firm — Kilpatrick Townsend & Stockton LLP

(57) ABSTRACT

Apparatus, systems, computer-readable media, articles of manufacture and methods for selecting an antibody. Apparatus, systems, computer-readable media, articles of manufacture and methods for producing the selected antibody. The selecting may include determining one or more physiochemical characteristics of the antibody. The determining may be based on antibody structural parameters.

13 Claims, 21 Drawing Sheets

(56) References Cited

OTHER PUBLICATIONS

Hess et al., "LINCS: A Linear Constraint Solver for Molecular Simulations" Journal of Computational Chemistry 18(12):1463-1472 ( 1997).
Hotzel et al., "A strategy for risk mitigation of antibodies with fast clearance" mAbs 4(6):753-760 ( 2012).
Igawa et al., "Engineering the variable region of therapeutic IgG antibodies" mAbs 3(3):243-252 ( 2011).
Igawa et al., "Reduced elimination of IgG antibodies by engineering the variable region" Protein Engineering, Design & Selection 23(5):385-392 ( 2010).
International Search Report ( dated Aug. 2015).
Iwao et al., "Oxidation of Arg-410 Promotes the Elimination of Human Serum Albumin" Biochimica et Biophysica Acta 1764:743-749 ( 2006).
Ji et al., "Methionine, Tryptophan, and Histidine Oxidation in a Model Protein, PTH: Mechanisms and Stabilization" Journal of Pharmaceutical Sciences 98(12):4485-4500 (Dec. 2009).
Jorgensen et al., "Comparison of simple potential functions for simulating liquid water" J. Chem. Phys. 79(2):926-935 (Jul. 15, 1983).
Jorgensen et al., "Development and Testing of the OPLS All-Atom Force Field on Conformational Energicts and Properties of Organic Liquids" J. Am. Chem. Soc. 118:11225-11236 ( 1996).
Kanai et al., "Reversible Self-Association of a Concentrated Monoclonal Antibody Solution Mediated by Fab-Fab Interaction that Impacts Solution Viscosity" Journal of Pharmaceutical Sciences 97(10):4219-4227 (Oct. 2008).
Kortkhonjia et al., "Solution Dynamics of Monoclonal Antibodies: Experimental and Computatiional Approach" Cell press 98(3 SUPPL 1):443a (Feb. 2010).
Lange et al., "Full correlation analysis of conformational protein dynamics" Proteins 70:1294-1312 ( 2008).
Lauer et al., "Developability Index: A Rapid In Silico Tool for the Screening of Antibody Aggregation Propensity" Journal of Pharmaceutical Sciences 10(1):112-114 (Jan. 2012).
Li et al., "Framework Selection Can Influence Pharmacokinetics of a Humanized Therapeutic Antibody Through Differences in Molecule Charge" mAbs 6(5):1255-1264 ( 2014).
Li et al., "Very Fast Empirical Prediction and Rationalization of Protein pKa Values" Proteins: Structure, Function, and Bioinformatics 61:704-721 ( 2005).
Liu et al., "Reversible Self-Association Increases the Viscosity of a Concentrated Monoclonal Antibody in Aqueous Soution" Journal of Pharmaceutical Sciences 94(9):1928-1940 (Sep. 2005).
Miyamoto et al., "SETTLE: An Analytical Version of the SHAKE and RATTLE Algorithm for Rigid Water Models" Jounal of Computational Chemisty 13(8):952-962 ( 1992).
Neergaard et al., "Viscosity of High Concentration Protein Formulations of Monoclonal Antibodies of the IgG1 and IgG4 Subclass—Prediction of Viscosity Through Protein-Protein Interaction Measurements" European Journal of Pharmaceutical Sciences 49:400-410 ( 2013).
Radkiewicz et al., "Neighboring Side Chain Effects on Asparaginyl and Aspartyl Degradation: An Ab Initio Study of the Relationship between Peptide Conformation and Backbone NH Acidity" J. Am. Chem Soc. 123:3499-3506 ( 2001).
Rojko et al., "Formation, Clearance, Deposition, Pathogenicity, and Identification of Biopharmaceutical-related Immune Complexes: Review and Case Studies" Toxicologic Pathology 42:725-764 ( 2014).
Sali et al., "Comparative Protein Modelling by Satisfaction of Spatial Restraints" J. Mo. Biol. 234:779-815 ( 1993).
Sharma et al., "In Silico Selection of Therapeutic Antibodies for Development: Viscotiy, Clearance, and Chemical Stability" PNAS 111(52):18601-18606 (Dec. 30, 2014).
Sharma et al., "Predictive tools toward screening monoclonal antibodies with optimal physicochemical properties" American Chemical Society, Abstracts of Papers 241 (Mar. 1, 2011).
Shire et al., "Challenges in the Development of High Protein Concentration Formulations" Journal of Pharmaceutical Sciences 93(6):1390-1402 (Jun. 2004).
Skogh et al., "Physicochemical Properties and Blood Clearance of Human Serum Albumin Conjugated to Different Extents with Dinitrophenyl Groups" Int. Archs Allergy appl. Immun. 70:238-244 ( 1983).
Sreedhara et al., "Characterization of the Isomerization Products of Aspartate Residues at Two Different Sites in a Monoclonal Antibody" Pharm. Res. 29:187-197 ( 2012).
Wakankar et al., "Aspartate Isomerization in the Complementarity-Determining Regions of Two Closely Related Monoclonal Antibodies" Biochemistry 46:1534-1544 ( 2007).
Wang et al., "Monoclonal Antibody Pharmacokinetics and Pharmacodynamics" Clinical Pharmacology & Therapeutics 84(5):548-558 (Nov. 2008).
Wu et al., "Development of Motavizumab, an Ultra-potent Antibody for the Prevention of Respiratory Syncytial Virus Infection in the Upper and Lower Respiratory Tract" J. Mol. Biol. 368:652-665 ( 2007).
Xu et al., "Modigying the OPLS-AA Force Field to Improve Hydration Free Energies for Several Amino Acid Side Chains Using New Atomis Charges and an Off-Plane Charge for Aromatic Residues" J. Comput. Chem. 28:689-697 ( 2007).
Yadav et al., "Establishing a Ling Between Amino Acid Sequences and Self-Associating and Viscoelastic Behavior of Two Closely Related Monoclonal Antibodes" Pharmaceutical Research 28:1750-1764 ( 2011).
Yadav et al., "Specific Interactions in High Concentration Antibody Solutions Resulting in High Viscosity" Journal of Pharmaceutical Sciences 99(3):1152-1168 (Mar. 2010).
Yadav et al., "The Influence of Charge Distribution on Self-Association and Viscosity Behavior of Monoclonal Antibody Solutions" Molecular Pharmaceutics 9:791-802 ( 2012).
Yi et al., "Isomerization of Asp-Asp Motif in Model Peptides and a Monoclonal Antibody Fab Fragment" Journal of Pharmaceutical Sciences 102(3):947-959 (Mar. 2013).
Yu et al., "Accurate Determination of Succimide Degradation Products Using High Fidelity Trypsin Digestion Peptide Map Analysis" Anal. Chem. 83:5912-5919 ( 2011).
Zheng et al., "Minipig as potential translatable model for monoclonal antibody pharmacokinetics after intravenous and subcutaneous adminisration" mAbs 4(2):243-255 ( 2012).
B. Helk et al., "PEGS Europe".
Kanai et al., "Rheological properties of high concentration therapeutic antibody solutions" Abstract 232nd ACS National Meeting, San Francisco, CA United States, ( Sep. 10-14, 1006).
Vikas K. Sharma, "Predictive Tools Towards Screening Monoclonal Antibodies with Optimal Physicochemical Properties" American Chemical Society, Denver, Colorado, 22 slides (2011).

\* cited by examiner

| mAb | η, High IS 150 mg/mL | η, High IS 180 mg/mL | Fv q | Fv CAP | HI |
|---|---|---|---|---|---|
| mAb1 | 7 | 12 | 7.9 | 14.5 | 0.78 |
| mAb2 | 5 | 7.1 | 7.7 | 12.1 | 0.93 |
| mAb3 | 7.4 | 13 | 6.1 | 8.4 | 0.92 |
| mAb4 | 8 | 14 | 3.6 | 1.3 | 1.01 |
| mAb5 | 8.4 | 15 | 1.5 | -4.5 | 1.1 |
| mAb6 | 11 | 20 | 3.9 | 3.8 | 1.19 |
| mAb7 | 20 | 46 | 3.3 | 2.6 | 1.32 |
| mAb8 | 12 | 22 | 4.5 | 0.9 | 0.99 |
| mAb9 | 26 | 70 | 0.5 | -7.5 | 1.44 |
| mAb10 | 15 | 33 | 1.8 | -6.5 | 0.93 |

FIG. 1A

| mAb | η, Low IS 150 mg/mL | Fv q | Fv CAP |
|---|---|---|---|
| mAb1' | 3 | 6.5 | 9.46 |
| mAb2' | 5 | 7.7 | 12.1 |
| mAb3' | 5.6 | 7.9 | 14.5 |
| mAb4' | 8.5 | 3.6 | 1.28 |
| mAb5' | 10 | 3.9 | 3.8 |
| mAb6' | 20 | 3.3 | 2.6 |
| mAb7' | 35 | 1.5 | -4.5 |
| mAb8' | 48 | 4.9 | 0.94 |
| mAb9' | 180 | 0.5 | -7.5 |
| mAb10' | 250 | 1.8 | -6.48 |

FIG. 1B

| mAbs | HI (CDRs) | LC1 | LC2 | LC3 | HC1 | HC2 | HC3 | HI Sum, LC1, LC3 HC3 | Fv Charge, pH 5.5 | Fv Charge, pH 7.4 | Clearance, mL/kg/day |
|---|---|---|---|---|---|---|---|---|---|---|---|
| mAb1 | 1.2 | 1.2 | 1.4 | 0.5 | 1.4 | 1.1 | 3.9 | 5.8 | 4.3 | 3.0 | 61.9 |
| mAb2 | 1.3 | 1.0 | 4.0 | 1.6 | 14.3 | 0.8 | 0.9 | 3.4 | 2.2 | -3.0 | 55 |
| mAb3 | 1.3 | 0.9 | 5.7 | 1.7 | 2.5 | 1.6 | 1.5 | 4.1 | 0.6 | -1.0 | 53.7 |
| mAb4 | 1.2 | 1.2 | 1.5 | 0.5 | 1.4 | 1.1 | 3.9 | 5.8 | 2.4 | 1.0 | 20.2 |
| mAb5 | 0.8 | 0.6 | 0.3 | 1.9 | 2.3 | 0.6 | 0.6 | 3.0 | 8.5 | 2.1 | 16.2 |
| mAb6 | 1.1 | 0.8 | 5.8 | 0.2 | 3.2 | 1.5 | 0.6 | 1.6 | -2.3 | -3.9 | 14 |
| mAb7 | 1.0 | 1.6 | 0.2 | 0.6 | 6.1 | 0.5 | 1.7 | 3.9 | 8.1 | 4.1 | 10.1 |
| mAb8 | 1.0 | 0.6 | 0.2 | 0.2 | 1.9 | 1.4 | 1.5 | 2.8 | 0.4 | -0.9 | 7.7 |
| mAb9 | 1.1 | 0.6 | 5.7 | 0.1 | 8.3 | 0.8 | 1.3 | 2.1 | 1.4 | 0.0 | 6.7 |
| mAb10 | 0.8 | 0.7 | 0.3 | 0.2 | 3.5 | 1.4 | 1.0 | 1.8 | 1.1 | -1.9 | 6 |
| mAb11 | 0.9 | 0.8 | 5.7 | 0.2 | 1.2 | 0.7 | 1.2 | 2.1 | 6.1 | 4.1 | 5.9 |
| mAb12 | 0.9 | 0.6 | 1.0 | 0.7 | 3.6 | 0.6 | 2.5 | 3.8 | 4.9 | 2.0 | 5.4 |
| mAb13 | 1.1 | 0.7 | 1.6 | 0.5 | 3.3 | 1.3 | 1.1 | 2.3 | 5.7 | 3.0 | 3.0 |
| Avg (SD) mAb 1-7 | 1.1 (0.2) | 1.0 (0.3) | 2.7 (2.4) | 1.0 (0.7) | 4.4 (4.6) | 1.0 (0.4) | 1.9 (1.5) | 3.9 (1.4) | | | |
| Avg (SD) mAb 8-13 | 1.0 (0.1) | 0.7 (0.1) | 2.4 (2.6) | 0.4 (0.3) | 3.6 (2.5) | 1.0 (0.4) | 1.4 (0.6) | 2.5 (0.7) | | | |

FIG. 2

| Clearance | Charge | HI Sum Value (LC CDR1, LC CDR3, HC CDR3) |
|---|---|---|
| Normal (<10 mL/kg/day) | -2.0 - 6.2 | > 4.0 |
| Fast (>/=10 mL/kg/day) | <= -2.0 or >/= 6.2 | <= 4.0 |

FIG. 3

| mAb | HI, SUM | Fv Charge, pH 5.5 | CI | Experimental Clearance Assignment | Predicted Clearance Assignment |
|---|---|---|---|---|---|
| mAb1 | 2.4 | 2.6 | 3 | Normal | Normal |
| mAb2 | 2.2 | 4.3 | 3 | Normal | Normal |
| mAb3 | 2.7 | 3.1 | 3 | Normal | Normal |
| mAb4 | 4.0 | 0.4 | 4 | Normal | Normal |
| mAb5 | 2.2 | 5.3 | 4 | Normal | Normal |
| mAb6 | 1.2 | 3.3 | 4 | Normal | Normal |
| mAb7 | 3.3 | 3.4 | 4 | Normal | Normal |
| mAb8 | 2.8 | 5.6 | 4 | Normal | Normal |
| mAb9 | 3.4 | 4.4 | 4 | Normal | Normal |
| mAb10 | 2.6 | 0.6 | 4 | Normal | Normal |
| mAb11 | 2.3 | 1.8 | 5 | Normal | Normal |
| mAb12 | 2.8 | 5.1 | 5 | Normal | Normal |
| mAb13 | 2.6 | 4.8 | 5 | Normal | Normal |
| mAb14 | 3.6 | 4.5 | 5 | Normal | Normal |
| mAb15 | 4.1 | 3.6 | 5 | Normal | Fast |
| mAb16 | 3.8 | 4.9 | 5 | Normal | Normal |
| mAb17 | 3.6 | 7.7 | 5 | Normal | Fast |
| mAb18 | 4.3 | 3.2 | 6 | Normal | Fast |
| mAb19 | 3.5 | 3.9 | 6 | Normal | Normal |
| mAb20 | 2.1 | 6.1 | 6 | Normal | Normal |
| mAb21 | 1.8 | 1 | 6 | Normal | Normal |
| mAb22 | 1.0 | 3.7 | 7 | Normal | Normal |
| mAb23 | 2.1 | 1.4 | 7 | Normal | Normal |
| mAb24 | 2.6 | 8.3 | 7 | Normal | Fast |
| mAb25 | 3.1 | 7 | 8 | Normal | Fast |
| mAb26 | 2.8 | 0.4 | 8 | Normal | Normal |
| mAb27 | 3.7 | 3.3 | 8 | Normal | Normal |

FIG. 4

| | | | | | |
|---|---|---|---|---|---|
| mAb28 | 1.9 | -1.5 | 9 | Normal | Normal |
| mAb29 | 3.3 | 3.4 | 9 | Normal | Normal |
| mAb30 | 5.5 | 1.4 | 10 | Fast | Fast |
| mAb31 | 1.7 | -2.5 | 10 | Fast | Fast |
| mAb32 | 3.9 | 8.1 | 10 | Fast | Fast |
| mAb33 | 3.1 | 10.6 | 11 | Fast | Fast |
| mAb34 | 5.5 | 1.4 | 12 | Fast | Fast |
| mAb35 | 3.2 | 0.4 | 13 | Fast | Normal |
| mAb36 | 4.0 | 6.3 | 14 | Fast | Fast |
| mAb37 | 3.0 | 6.5 | 16 | Fast | Fast |
| mAb38 | 2.1 | 8.1 | 17 | Fast | Fast |
| mAb39 | 1.6 | -2.3 | 20 | Fast | Fast |
| mAb40 | 5.6 | 2.4 | 20 | Fast | Fast |
| mAb41 | 1.6 | 8.1 | 22 | Fast | Fast |
| mAb42 | 6.1 | 2.4 | 26 | Fast | Fast |
| mAb43 | 4.1 | 0.6 | 54 | Fast | Fast |
| mAb44 | 3.4 | -2.2 | 55 | Fast | Fast |
| mAb45 | 5.6 | 4.3 | 61 | Fast | Fast |

FIG. 4 (Cont.)

| mAb | Chain | Resnum | Sasa Sidechain | % SASA | AAPH Oxidation | Experimental Hot Spot | Predicted Hot Spot (>30% SASA) |
|---|---|---|---|---|---|---|---|
| mAb1 | HC | 33 | 83 | 31 | 97 | Yes | Yes |
| mAb2 | HC | 100 | 133 | 50 | 94.8 | Yes | Yes |
| mAb3 | HC | 107 | 60 | 23 | 90 | Yes | No |
| mAb4 | HC | 33 | 97 | 37 | 84 | Yes | Yes |
| mAb5 | HC | 105 | 189 | 71 | 80 | Yes | Yes |
| mAb6 | HC | 104 | 117 | 44 | 80 | Yes | Yes |
| mAb7 | HC | 103 | 114 | 43 | 80 | Yes | Yes |
| mAb8 | HC | 103 | 83 | 31 | 69 | Yes | Yes |
| mAb9 | HC | 28 | 140 | 53 | 65 | Yes | Yes |
| mAb3 | HC | 33 | 90 | 34 | 60 | Yes | Yes |
| mAb10 | HC | 106 | 105 | 39 | 55 | Yes | Yes |
| mAb11 | HC | 52 | 168 | 63 | 54 | Yes | Yes |
| mAb12 | LC | 94 | 173 | 65 | 53 | Yes | Yes |
| mAb13 | HC | 53 | 169 | 64 | 38 | Yes | Yes |
| mAb14 | HC | 107 | 43 | 16 | 20 | No | No |
| mAb15 | LC | 92 | 117 | 44 | 9.6 | No | Yes |
| mAb15 | HC | 33 | 91 | 34 | 8.6 | No | Yes |
| mAb16 | LC | 101 | 75 | 28 | 1.7 | No | No |
| mAb14 | LC | 90 | 66 | 25 | 0.2 | No | No |
| mAb10 | LC | 90 | 22 | 8 | 0.2 | No | No |
| mAb12 | HC | 109 | 129 | 49 | 0 | No | Yes |
| mAb7 | HC | 33 | 113 | 43 | 0 | No | Yes |
| mAb17 | HC | 106 | 63 | 24 | 0 | No | No |
| mAb13 | HC | 106 | 48 | 18 | 0 | No | No |
| mAb18 | HC | 33 | 38 | 14 | 0 | No | No |
| mAb6 | HC | 105 | 18 | 7 | 0 | No | No |
| mAb7 | HC | 105 | 14 | 5 | 0 | No | No |
| mAb8 | LC | 96 | 11 | 4 | 0 | No | No |
| mAb11 | LC | 100 | 8 | 3 | 0 | No | No |
| mAb17 | HC | 111 | 4 | 1 | 0 | No | No |
| mAb18 | LC | 152 | 2 | 1 | 0 | No | No |
| mAb19 | HC | 48 | 2 | 1 | 0 | No | No |
| mAb20 | HC | 35 | 1 | 1 | 0 | No | No |
| mAb21 | HC | 162 | 1 | 0 | 0 | No | No |
| mAb22 | LC | 39 | 0 | 0 | 0 | No | No |
| mAb8 | HC | 35 | 0 | 0 | 0 | No | No |
| mAb22 | HC | 37 | 0 | 0 | 0 | No | No |
| mAb13 | LC | 186 | 29 | 11 | 0 | No | No |

FIG. 5

| mAb | Asp | Seq (N+1) Residue | Measured Rate %/Week | SASA Asp (nm²) | RMSF Å | SASA (N+1, N) (nm²) | Measured Binary Input | Predicted Binary Output (All) | Predicted Binary Output (LOOCV) |
|---|---|---|---|---|---|---|---|---|---|
| mAb 1 | L30 | DD | 22 | 96 | 3.0 | 0.7 | 1 | 1 | 1 |
| mAb 2 | L32 | DG | 12 | 126 | 2.1 | 0.8 | 1 | 1 | 1 |
| mAb 3 | H102 | DG | 8 | 131 | 3.1 | 3.4 | 1 | 1 | 1 |
| mAb 5 | L30 | DG | 7 | 79 | 1.3 | 1.3 | 1 | 0 | 0 |
| mAb 1 | H62 | DD | 7 | 110 | 1.7 | 3.1 | 1 | 1 | 1 |
| mAb 6 | H105 | DD | 5 | 106 | 2.2 | 0.0 | 1 | 1 | 1 |
| mAb 2 | H55 | DG | 0 | 101 | 1.2 | 0.0 | 0 | 0 | 0 |
| mAb 2 | H73 | DG | 0 | 42 | 1.0 | 3.3 | 0 | 0 | 1 |
| mAb 1 | L31 | DD | 0 | 72 | 2.6 | 0.2 | 0 | 0 | 0 |
| mAb 7 | H106 | DD | 0 | 47 | 1.0 | 0.0 | 0 | 0 | 0 |
| mAb 3 | H62 | DS | 0 | 116 | 1.1 | 1.4 | 0 | 0 | 1 |
| mAb 2 | L34 | DS | 0 | 81 | 1.7 | 1.3 | 0 | 0 | 0 |
| mAb 1 | L92 | DT | 0 | 79 | 2.9 | 0.1 | 0 | 0 | 0 |
| mAb 4 | H31 | DT | 0 | 108 | 1.6 | 0.0 | 0 | 0 | 0 |
| mAb 4 | H90 | DT | 0 | 9 | 1.0 | 0.0 | 0 | 0 | 0 |

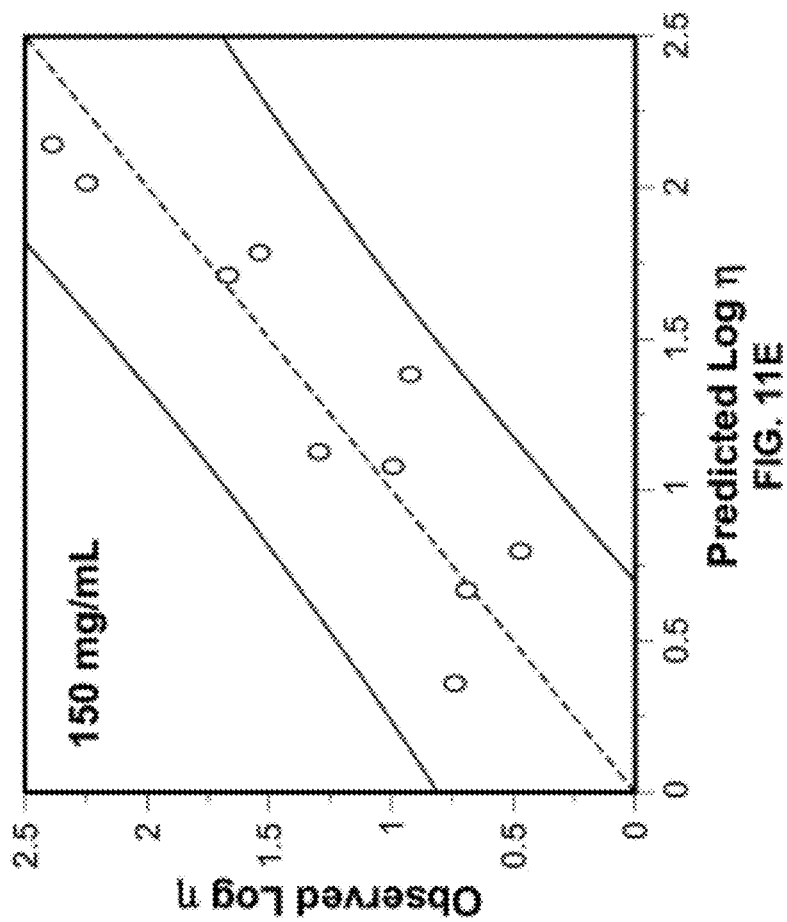
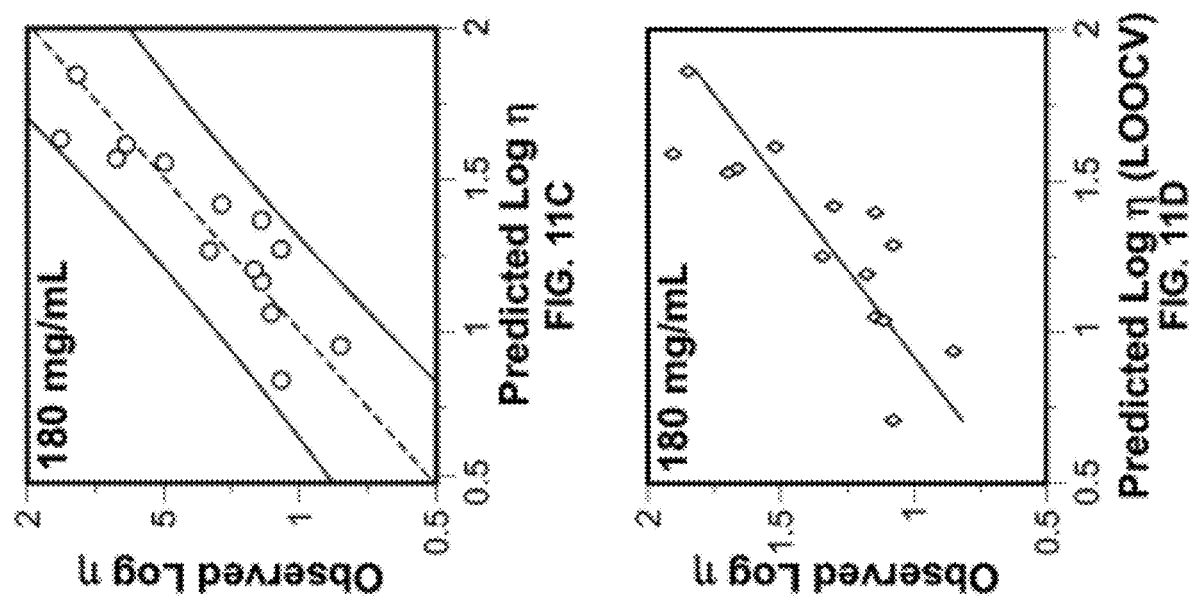

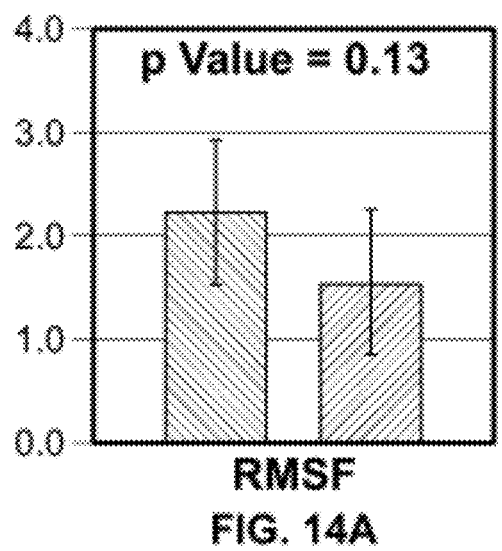
FIG. 14A RMSF
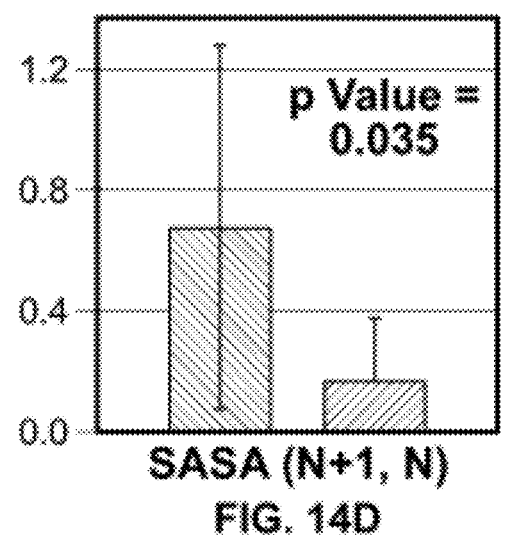
FIG. 14D SASA (N+1, N)
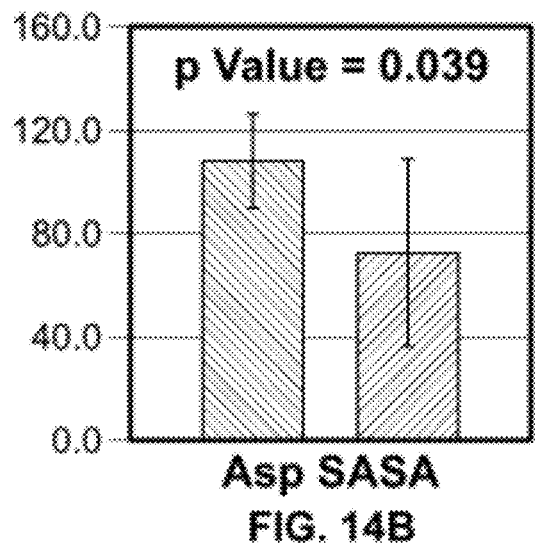
FIG. 14B Asp SASA
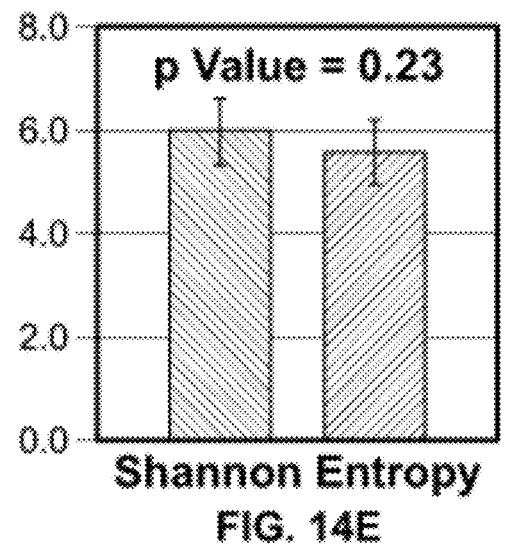
FIG. 14E Shannon Entropy
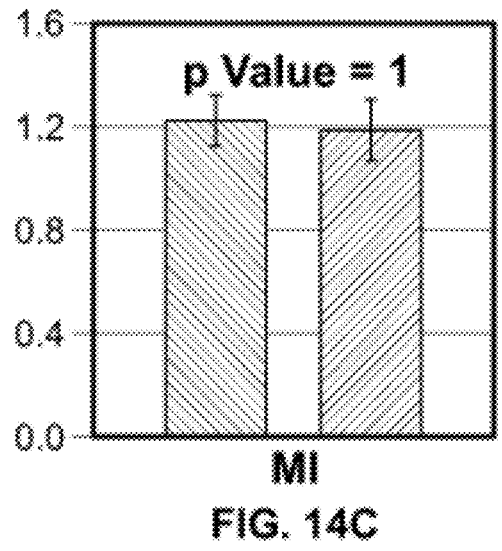
FIG. 14C MI

ANTIBODY SELECTION APPARATUS AND METHODS

CROSS REFERENCE TO OTHER RELATED APPLICATIONS

This application is a continuation of International Application No. PCT/US2014/067580 having an international filing date of Nov. 26, 2014, the entire contents of which are incorporated herein by reference, and which claims benefit under 35 U.S.C. § 119 to U.S. Provisional Patent Application No. 61/910,200 filed Nov. 29, 2013.

FIELD OF TECHNOLOGY

Aspects of the disclosure relate to apparatus, systems, computer-readable media, articles of manufacture and methods for selecting an antibody with one or more desirable properties, especially desirable properties for a therapeutic agent, and for manufacturing the antibody or the therapeutic agent comprising the antibody.

BACKGROUND OF THE INVENTION

Monoclonal antibodies ("monoclonal Ab" or "mAb") continue to emerge as an important class of therapeutic agents for the treatment of a variety of diseases including cancers, autoimmune disorders, and infections. For ease of use, patient convenience and less frequent dosing, it is preferred that an aqueous pharmaceutical is developed which is stable for its shelf-life (typically 2 years) and that the therapeutic mAb itself has normal clearance and plasma half-life (typically 3 weeks).

For mAb-based therapy, intended for treatment of certain chronic ailments, e.g., rheumatoid arthritis, delivery via the subcutaneous route using a device such as a prefilled syringe/auto-injector, may be employed for a patient's at-home use/self-administration and compliance (see, e.g., Eisenstein, M. Something new under the skin. *Nat Biotech* 29, 107-109 (2011)). A few mAb products are commercially available in a device for at-home use, e.g., Humira® by Abbott, and Simponi® by Centocor, etc., and several are currently being evaluated in clinical trials. In order to deliver several hundred milligrams of the active drug in a small volume (~1 mL) using a device, a liquid formulation containing high concentrations of mAb is required (see, e.g., Eisenstein, M. Something new under the skin. *Nat Biotech* 29, 107-109 (2011); Shire, S. J., Shahrokh, Z. & Liu, J. Challenges in the development of high protein concentration formulations. *Journal of Pharmaceutical Sciences* 93, 1390-1402 (2004)). Such delivery systems necessitate that the solution is of low viscosity because higher viscosity solutions are difficult to manufacture and administer, and could be painful to inject due to the need for a larger gauge needle and forces involved (see, e.g., Shire, S. J., Shahrokh, Z. & Liu, J. Challenges in the development of high protein concentration formulations. *Journal of Pharmaceutical Sciences* 93, 1390-1402 (2004)). Furthermore, it is necessary that the antibody remains stable (minimal chemical or physical degradation) in solution without losing efficacy while maintaining safety to attain sufficient shelf-life. Additionally, to avoid multiple injections per dose or more frequent dosing with the requisite low volume subcutaneous route of administration, it is advantageous to develop a mAb candidate with sufficient bioavailability and which also exhibits a normal clearance profile associated with a long plasma half-life (see, e.g., Wang, W., Wang, E. Q. & Balthasar, J. P. Monoclonal Antibody Pharmacokinetics and Pharmacodynamics. *Clin Pharmacol Ther* 84, 548-558 (2008); Zheng, Y. et al. Minipig as a potential translatable model for monoclonal antibody pharmacokinetics after intravenous and subcutaneous administration. *mAbs* 4, 243-255; see also Chennamsetty, N., Voynov, V., Kayser, V., Helk, B. & Trout, B. L. Design of therapeutic proteins with enhanced stability. *Proceedings of the National Academy of Sciences* 106, 11937-11942 (2009)). Thus, there exists a need for a method or apparatus that facilitates prediction of Ab with desirable properties.

SUMMARY OF INVENTION

Provided herein are aspects and embodiments that relate to novel apparatus and methods to aid in antibody selection and manufacturing. Viscosity of mAb solutions at defined concentrations, clearance rate in vivo, such as in Cynomolgus (Cyno) monkeys, tryptophan (Trp) oxidation and aspartic acid (Asp) isomerization, were studied as exemplary mAb properties important for optimal manufacturability, development, injectability, shelf-life and pharmacokinetic behavior, and therefore enabling drug delivery, efficacy and patient's ease of use. It is shown herein that using the structural parameters identified by the instant invention and through molecular dynamics (MD) simulations, one may reasonably well predict the desirable attributes of mAbs and risk-rank mAb candidates for final selection.

As described herein, properties extracted from Ab amino acid sequence ("sequence extracted properties," "sequence-based properties," "structural parameters" or ""sequence-based structural parameters") such as charge, charge asymmetry, and hydrophobicity, along with multivariate analysis tools, are sufficient to differentiate between mAbs of varying viscosity-concentration profiles, between mAbs of normal and fast clearance values and between mAbs of desirable and undesirable stability, such as with respect to Trp oxidation and Asp isomerization. While intermolecular and intramolecular interactions contributing to viscosity, clearance and stability involve three dimensional structure and associated dynamics, it is an unexpected result of the current work that the sequence-based structural parameters described herein may sufficiently determine or predict Ab properties such as viscosity, clearance rate and stability. In addition, it is an unexpected result of the current work that the sequence-based structural parameters may sufficiently predict or differentiate Ab properties among multiple Abs, especially Abs within the same class.

For site-specific properties such as Trp oxidation or Asp isomerization, local dynamics and conformational attributes appear to play an important role; therefore a structure-based MD analysis may be required. Inclusion of computational in-silico tools modeling structural MD may enable screening of a larger number of candidates with minimal time and resources spent as compared to wet and other experimental approaches, and therefore increase efficiency in antibody candidate selection. It is shown in the instant invention that through careful analysis of molecular motions using MD simulations and through extraction of relevant structural properties, one may differentiate between reactive and non-reactive sites relevant to shelf-life of an Ab-containing therapeutic agent. Depending on the reaction mechanism, different sets of parameters may need to be assessed. For example, for Trp oxidation, time-averaged solvent accessible surface area (SASA) of a Trp residue (side chain) was sufficient to differentiate between reactive and non-reactive sites; however, additional structural parameters along with multivariate analysis were required to differentiate between the Asp isomerization sites. The instant invention shows that one may perform in-silico sequence-based structural analysis on mAbs to select lead candidates with desirable development attributes. This ability may improve the probability of technical success to move novel mAb-based therapeutics efficiently into clinical development and ultimately benefit patients.

In additional aspects, the invention also provides antibodies selected, produced and/or antibodies determined to satisfy a certain design criterion, by the methods described herein.

BRIEF DESCRIPTION OF THE DRAWINGS

FIGS. 1A and B are Tables of Parameters for Principal Component Regression Analysis for viscosity prediction from results of 10 mAbs at high ionic strength (IS) (FIG. 1A) and 10 partially overlapping mAbs at low IS (FIG. 1B).

FIG. 2 is a Table of Clearance Values in Cyno monkeys and the calculated sequence-based structural parameters for a training set of 13 mAbs. Hatching in Table columns HI Sum, Fv Charge pH 5.5 and Clearance correspond to ranges of FIG. 3's Table columns HI Sum Value, Charge and Clearance, respectively. Rightward forward-slash hatching of a FIG. 2 table entry indicates that the entry's value lies within a range given in FIG. 3's upper row of values. Leftward back-slash hatching of a FIG. 2 table entry indicates that the entry's value lies within a range given in FIG. 3's lower row of values.

FIG. 3 is a Table of Assigned Criteria based on the training set of 13 mAbs as shown in FIG. 2 to differentiate between fast clearance and normal clearance in Cyno monkeys.

FIG. 4 is a Table of Experimental versus Predicted Clearance Assignment on a set of 45 mAbs based on the criteria listed in FIG. 3, with FIG. 4's Table column CI corresponding to FIG. 2's Table column Clearance, and with FIG. 4's hatching as in FIG. 2 and extended to FIG. 4's Experimental and Predicted Assignment columns.

FIG. 5 is a Table of Trp Oxidation Hot Spot Prediction using Trp side chain SASA for Trps of various residue number (Resnum) along a heavy chain (HC) or a light chain (LC) in the training set of 13 mAbs. (See Detailed Description, below, for other Table column headings.) Rightward forward-slash hatching of a table entry indicates that the entry's value lies within a desired range. Leftward back-slash hatching of a table entry indicates that the entry's value lies outside a desired range.

FIG. 8A presents Fv Charge at pH 5.5; FIG. 8B presents Fv Charge Asymmetry Parameter (FvCAP) at pH 5.5; FIG. 8C presents Hydrophobicity (or Hydrophobicity Index, HI). Charge was calculated using the whole variable fragment (Fv) sequence for FIG. 8A and using the heavy chain variable (VH) domain sequence and the light chain variable (VL) domain sequence for calculation of FvCAP for FIG. 8B. HI was calculated using the amino acid composition of complementarity determining regions (CDRs) for FIG. 8C.

In FIG. 9A the parameter is hydrophobicity; in FIG. 9B, Fv charge at pH 5.5; and in FIG. 9C, FvCAP at pH 5.5. Viscosity values were obtained in buffered solutions of low ionic strength at 20 mM buffer concentration at pH 5.5.

In FIG. 10A the parameter is hydrophobicity; in FIG. 10B, Fv charge at pH 5.5; and in FIG. 10C, FvCAP at pH 5.5. Viscosity values were obtained in buffered solutions of high ionic strength at 200 mM arginine HCl buffer concentration at pH 5.5.

FIGS. 11A-E show Principal Component Regression (PCR) analysis plots showing predicted viscosity values against experimentally observed viscosity values for various different mAbs under varied conditions: FIGS. 11A, 11B and 11E show PCR analysis of sets of 10 different mAbs. FIGS. 11C and 11D show PCR analysis of sets of 14 different mAbs. The results shown in FIGS. 11A, 11B, 11C and 11D were obtained under high ionic strength buffer solution conditions. The results shown in FIG. 11E were obtained under low ionic strength buffer solution conditions. FIGS. 11A and 11E show plots at a mAb concentration of 150 mg/mL. FIGS. 11B, 11C and 11D show plots at a mAb concentration of 180 mg/mL. The predicted viscosity values are output values from PCR analysis and are described by Equations described in the Examples section, below, for 150 mg/mL and for 180 mg/mL of mAb. Each data point represents a mAb and the curved lines, where present, represent 90% confidence intervals.

FIG. 13A shows a relationship between antibody clearance in Cyno monkeys and calculated antibody isoelectric point (in logarithmic form, pI); and FIG. 13B shows a relationship between antibody clearance in Cyno monkeys and Hydrophobicity Index calculated using mAb CDR H1 sequences.

FIGS. 14A-E show a comparison of the average value and standard deviation of various properties extracted from MD simulations for labile (leftward back-slash hatching, on the left of each figure) vs. stable Asp residues (rightward forward-slash hatching, on the right of each figure). Each plot includes average value and standard deviation. Calculated p-values are shown on each plot. RMSF, Asp SASA and SASA (N+1, N) all demonstrate a significant difference (80% confidence interval (CI)) between labile and stable residues. Intra-residue mutual information (MI) and Shannon entropy properties do not differ significantly between the averages of stable vs. labile residues.

FIG. 15D shows pKa distribution of charged side chains in the Fab used in plot A. The y-axis shows standard, non-structure-based, pKa values of amino acid side chains of D, E, H, Y, K, and R (as also marked by the value along the x-axis of the associated vertical line). Each horizontal data point for a given amino acid side chain is the structure-based pKa value obtained from PROPKA for that amino acid. While FIG. 15D shows a distribution of pKa values obtained for each amino acid side chain, the overall charge-pH profile based on structure-based charge calculation was comparable to the sequence-based calculations, as shown in FIGS. 15A-15C, in which the similarity in charge-pH profiles between sequence and structure was independent of Fab pI.

FIG. 16 shows a comparison of sequence-based Hydrophobicity Index (HI) values with those calculated from the structure. The sequence-based HI was calculated as described in the Exemplary Methods section, below, and is based on the relative ratio of hydrophobic to hydrophilic amino acids, where each amino acid is weighted by its Eisenberg hydrophobicity scale value. The structure-based Hydrophobicity Index is calculated similarly, except that the SASA determined from the structure is included in the calculation for each amino acid. The index is defined as:

$$HI\ (structure) = \Sigma(S_i E_i / S_j E_j)$$

where i represents the hydrophobic amino acids, i.e., A, F, I, L, V, W, Y and j represents the hydrophilic amino acids, i.e., D, E, G, H, K, M, N, Q, R, S, T. (For key to 1-letter identifying abbreviations for amino acids, see Table 1, below in text.)

S is the SASA value and E is the Eisenberg scale value of each amino acid. The calculation is done over all amino acids present in a given sequence/structure. A reasonable correlation is obtained between the structure-based HI and the sequence-based HI (Pearson's r=0.9).

Figure 17:
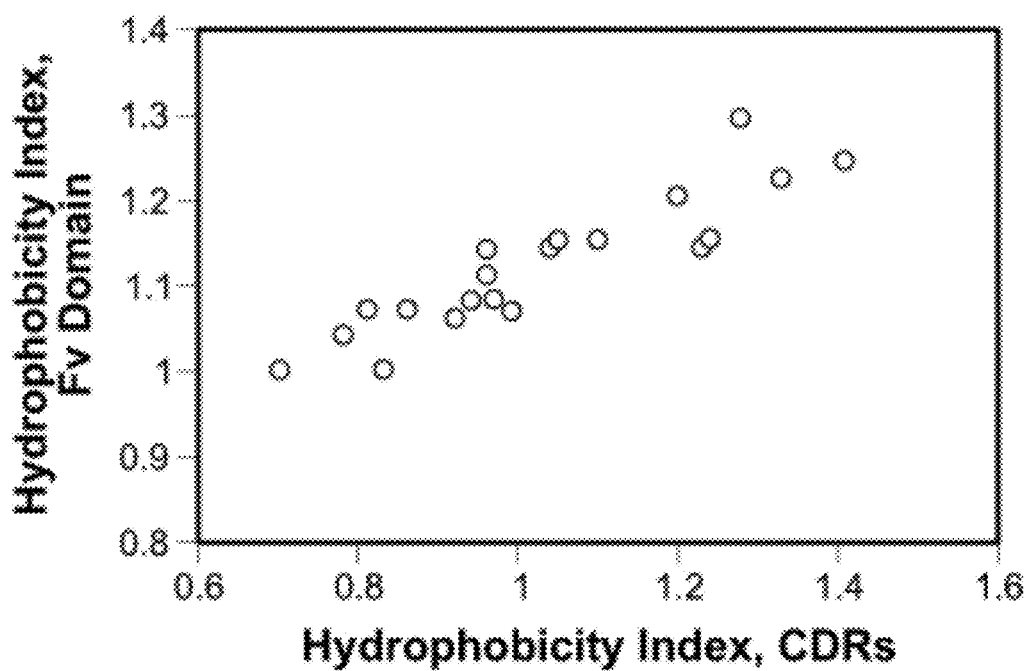

FIG. 17 shows a comparison of sequence-based HI values calculated from CDRs only to those calculated from their respective Fv domains for several mAbs of the sub/class of study, IgG1. HI values calculated using CDRs correlated well with those obtained using Fv (Pearson's r=0.9).

Figure 18:
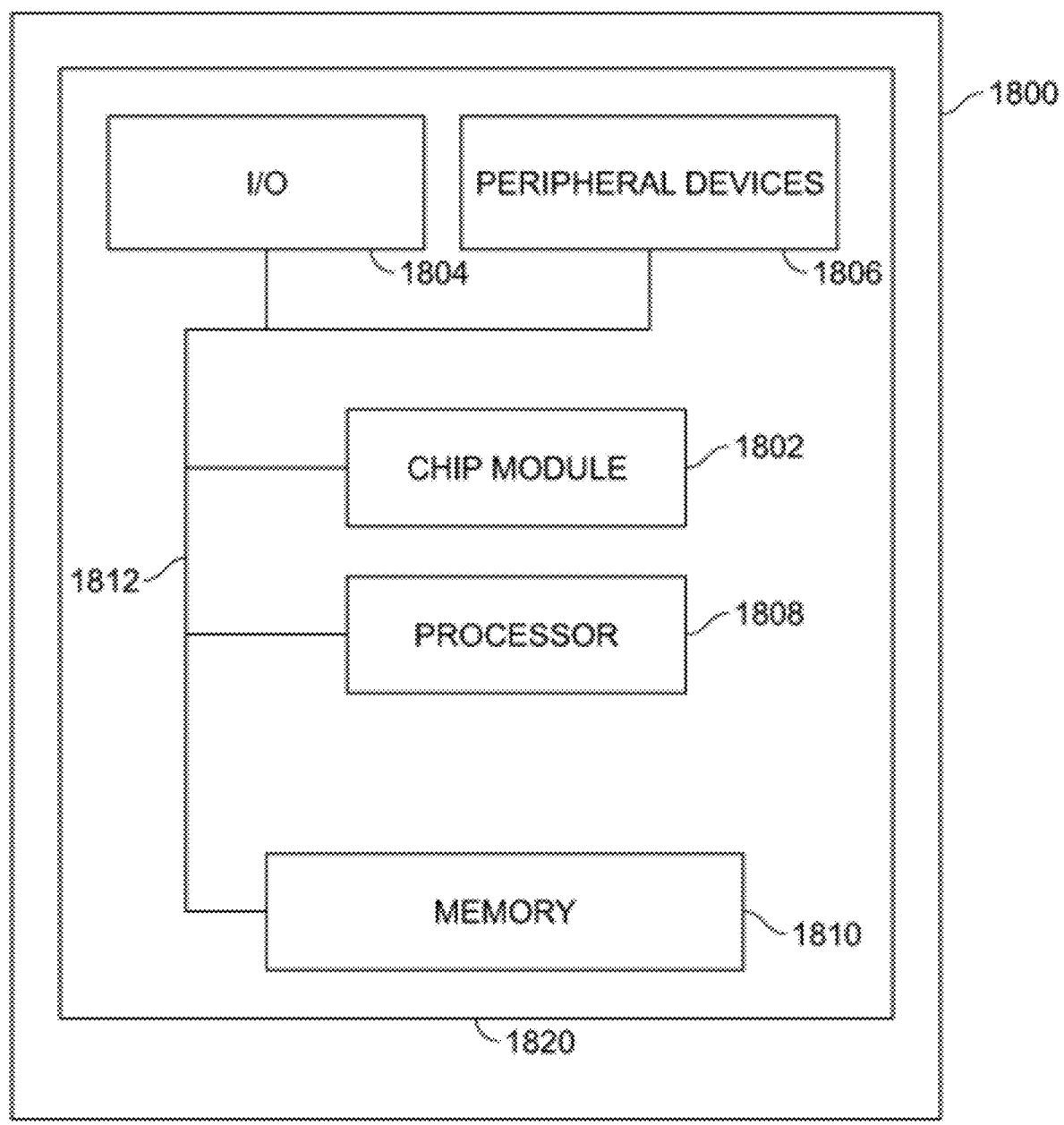

FIG. 18 shows an illustrative apparatus that may be configured in accordance with the principles of the invention.

Figure 19A:
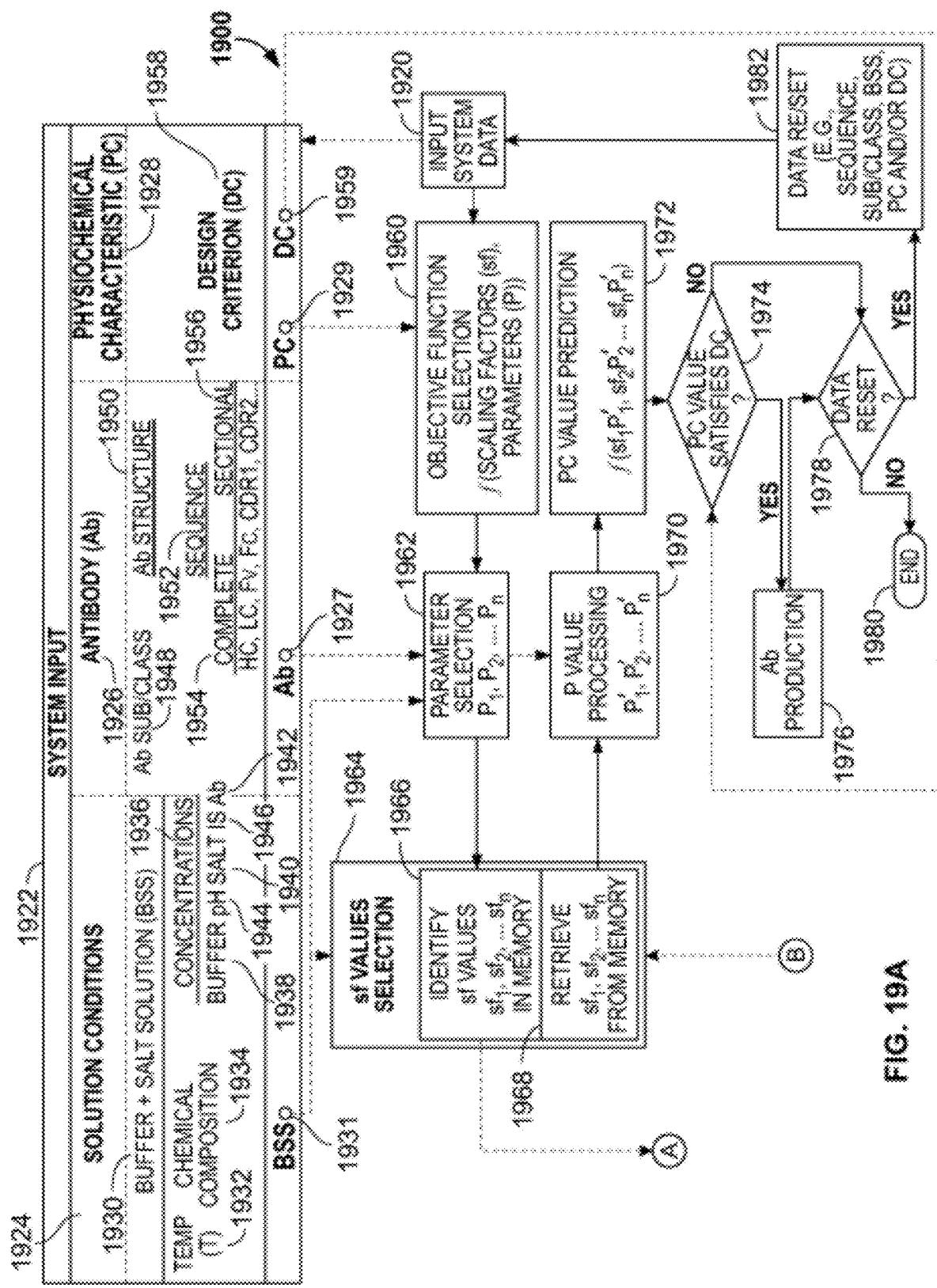
Figure 19B:
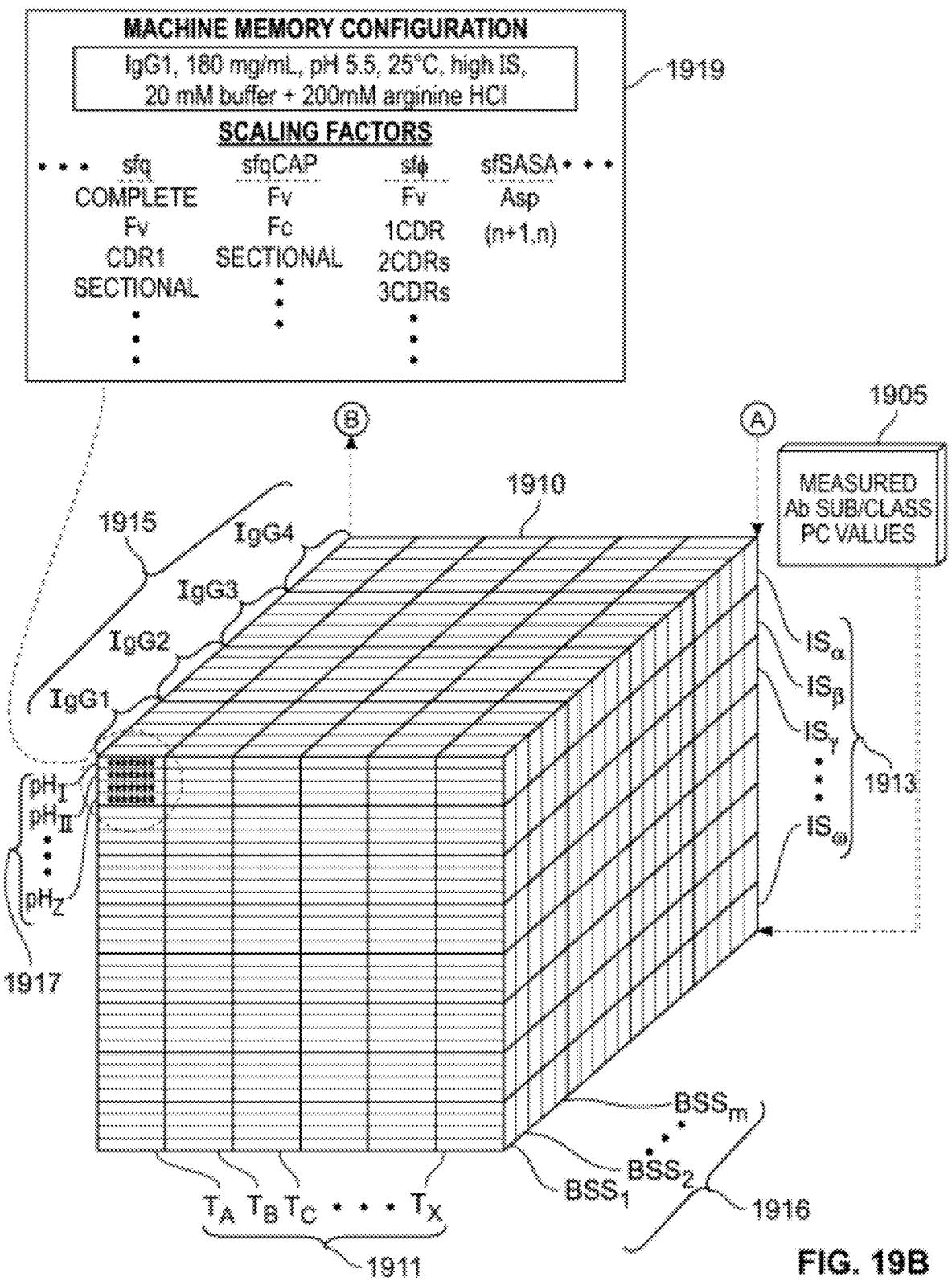

FIGS. 19A and 19B are a flow diagram of illustrative processes in accordance with the principles of the invention.

DETAILED DESCRIPTION OF THE DISCLOSURE

Apparatus, methods, articles of manufacturing, and corresponding computer-readable media, for determining whether an antibody has one or more physiochemical characteristics that satisfy one or more corresponding design criteria are provided. For any one of the one or more physiochemical characteristics, the determining may be a proxy for an empirical determination of a value of the physiochemical characteristic. The proxy may be a prediction of the value in the absence of, before or in lieu of an empirical determination. Values of empirical determinations and values of predictions and solution conditions under which determinations and predictions may be performed, may be approximate.

The one or more design criteria may be for a therapeutic agent comprising an antibody. The one or more design criteria may be for an antibody for any in vitro or in vivo use. The one or more design criteria may be for a composition, a pharmaceutical formulation or a pharmaceutical composition comprising an antibody. The determining may be a determination of the fitness or suitability of the antibody for inclusion in the therapeutic agent or for inclusion in a pharmaceutical formulation or a pharmaceutical composition.

The term "therapeutic agent" refers to an agent that at an effective amount exerts a desirable therapeutic effect in an animal, preferably a mammal, more preferably a primate, most preferably a human. A therapeutic agent may be formulated in a pharmaceutical composition, which may comprise more than one type of therapeutic agent.

The therapeutic agent comprising an antibody may be for intravenous injection, subcutaneous injection, intraperitoneal injection or any other form of administration. The therapeutic agent may be at high concentration in small volume for subcutaneous injection using a dispensing device. The therapeutic agent may require low viscosity. The therapeutic agent may be designed for infrequent dosing and may require long plasma half-life.

A "design criterion" for a therapeutic agent may refer to a physical, chemical or physiochemical target characteristic that the therapeutic agent is to have.

Apparatus and methods, and corresponding computer-readable media, for selecting the antibody for use in the therapeutic agent are provided. The computer-readable storage media may include non-transitory waves. The computer-readable storage media may include non-transitory signals. The antibody may be selected from two or more candidate-antibodies.

Apparatus and methods, and corresponding computer-readable media, for producing or manufacturing the antibody are provided. The antibody obtained may be for use in a therapeutic agent. The antibody obtained may be modified from a pre-existing antibody. The pre-existing antibody may be modified to produce a target-antibody that satisfies the one or more design criteria. The design criteria may be for a therapeutic agent.

The apparatus may perform one or more steps of the methods. The apparatus may include a logical processing device. The apparatus may include a data receiving device. The apparatus may include a data transmitting device. The apparatus may include machine-readable memory. Two or more of the devices may be in electronic communication with each other.

The media may be one or more non-transitory computer-usable media. The computer-usable media may have computer-readable program code embodied therein. The computer-readable program code, when executed by one or more processors, may cause a computer system to carry out steps of the methods.

The steps may be executed to determine the fitness or suitability of the antibody for inclusion in the therapeutic agent. The steps may be executed to select the antibody from several candidate-antibodies. The steps may be executed for manufacturing the antibody. The steps may be executed for modifying the pre-existing antibody. The steps may be executed for modifying the pre-existing antibody to produce the target-antibody.

Some or all of the steps may be executed in concert with each other, based on one of the physiochemical characteristics or a combination of two or more of the physiochemical characteristics, to combine one or more of the following: determination of the fitness of the antibody for inclusion in the therapeutic agent; selection of the antibody from several candidate-antibodies; manufacture of the antibody; modification of the pre-existing antibody to generate a target antibody; and production of the target-antibody.

Antibody physiochemical characteristics; antibody structural information; antibody structural parameters; design criteria; objective functions; objective function scaling factors; physiochemical characteristic indicies; antibodies; antibody production; logical processing devices, data transmitting devices and data receiving devices; and combination of features and principles of the invention will now be discussed.

Antibody Physiochemcial Characteristics

The exemplary physiochemical characteristics include viscosity, clearance, stability, aspartic acid lability and tryptophan lability.

The physiochemical characteristic may be a viscosity. The physiochemical characteristic may be a pharmacokinetic clearance rate. The physiochemical characteristic may be a lability. The lability may correspond to a stability of the antibody. The lability may correspond to a shelf-life of the antibody.

The physiochemical characteristic may be a stability. The physiochemical characteristic may be a shelf-life. The physiochemical characteristic may be an aspartic acid (Asp) lability. The physiochemical characteristic may be a tryptophan (Trp) lability. The Asp lability may correspond to Asp isomerization. The Trp lability may correspond to Trp oxidation. The lability may affect the stability and shelf-life of the antibody.

The physiochemical characteristic may depend on a solution condition. The solution condition may be an aqueous solution condition. The solution condition may be a temperature. The solution condition may be a pH. The solution condition may be an ionic strength. The solution condition may be an antibody concentration. The ionic strength of an aqueous solution of antibody may be set in whole or in part by the concentration of an ionic buffer solution in which the antibody is present. An example of an ionic buffer solution may be a histidine acetate buffer solution. The solution condition may include solute concentration. The solute concentration may include antibody concentration.

Antibody Structural Information

The antibody structural information may be used to calculate the structural parameters. The methods may include calculating the structural parameters from the antibody structural information.

The structural information may correspond to a three-dimensional structure. The structural information may correspond to a primary structure. The primary structure may refer to the primary amino acid sequence. The primary structure may include primary structure of a variable domain of the antibody. The primary structure may be exclusively variable domain primary structure. The primary structure may include a variable domain light chain (VL) amino acid sequence. The primary structure may include a variable domain heavy chain (VH) amino acid sequence. The primary structure may include one or more CDR amino acid sequences. The primary structure may include primary structure of a constant region of the antibody. The primary structure of the constant region may include a constant region light chain (CL) amino acid sequence. The primary structure of the constant region may include a constant region heavy chain (CH) amino acid sequence. The primary structure of the constant region may include one or more of a constant region heavy chain CH1, CH2 and CH3 amino acid sequence.

A structural parameter may be calculated from the primary structural information, and may include no information from structures other than the primary structure. The primary sequence may be derived from the DNA sequence obtained by DNA sequencing. DNA sequencing technique is well-known in the art.

The antibody structural information may be electronically encoded. The electronically encoded information may be stored in the machine-readable memory. The logical processing device may retrieve the antibody structural information from the machine-readable memory. The data receiving device may receive the antibody structural information. The logical processing device may calculate the physiochemical parameters from the antibody structural information. The data transmitting device may transmit the antibody structural information. The data transmitting device may transmit a signal corresponding to an outcome of the calculations.

The term "electronically encoded" refers to a form of information suitable for storage in, and retrieval from, an electronic database and/or for manipulation by an electronic computation device.

Antibody Structural Parameters

The structural parameter may be a net charge of the antibody. The structural parameter may be a charge asymmetry of the antibody. The structural parameter may be a hydrophobicity of the antibody. The structural parameter may be calculated from antibody structural information.

Antibody structural information may include primary structure information, for example, the amino acid sequence of the antibody. The amino acid sequence may be the amino acid sequence of a structural element of an antibody. Each of the structural elements may be an amino acid sequence. The structural elements may be adjacent to each other in the antibody amino acid sequence. The structural elements may be near each other in the antibody sequence. The structural elements may be associated with each other in the antibody. The structural element may be the heavy chain variable domain (VH) and/or the light chain variable domain (VL). The structural element may be one or more complementarity determining regions (CDRs). The structural element may be one or more constant regions (e.g., CH1, CL, CH2 and CH3). The structural element may be the heavy chain and light chain (half antibody). The structural element may be the entire antibody. The primary amino acid sequence may be the amino acid sequence of the heavy chain variable domain (VH), and/or the light chain variable domain (VL). The primary amino acid sequence may be the amino acid sequence of one or more of the CDRs. The primary amino acid sequence may be the amino acid sequence of one or more constant regions of the antibody. The antibody structure information may also include secondary structure information and higher level structural information, such as information as to three-dimensional molecular interactions that may contribute to viscosity, clearance and stability.

The structural parameters may include a net charge. The net charge may be the sum of charges of all amino acids within a structural element of the antibody. The net charge may be the sum of charges of all amino acids within a structural element of the antibody at a certain pH. The pH may be a pH from pH 4 to pH 9. The pH may be pH 5.5. A structural element may be the VH and VL domains. The net charge may be the sum of charges of all amino acids within the VH and VL domains. The net charge may be the sum of charges of all amino acids within one or more CDRs. The net charge may be the sum of charges of all amino acids within one or more constant regions.

The structural parameters may include a charge asymmetry. The charge asymmetry may be a product of the net charge of one structural element of the antibody and a net charge of at least one other structural element of the antibody. The charge asymmetry may be a product of the net charge of the VH and the net charge of VL of the antibody. Further, the charge asymmetry may be a product of, for example, the net charge of the Fv and Fc, or Fv and CH3 domain, or Fab and Fc, etc.

The structural parameters may include a hydrophobicity. The hydrophobicity may include a total of summation functions of hydrophobicity values corresponding to one or more CDRs. Each summation function may be a ratio of: (1) a sum of the values of hydrophobicity of hydrophobic residues of a CDR; and (2) a sum of the values of hydrophobicity of hydrophilic residues of the CDR. The value of hydrophobicity for each amino acid residue of the CDR may be an Eisenberg hydrophobicity scale value. Alternatively, the hydrophobicity may include a hydrophobicity value of Fv.

The structural parameters may be calculated by using molecular dynamics (MD) simulations. The MD simulations may correspond to a set of simulated solution conditions. The set may include solution conditions of a virtual solution. The simulated solution conditions may include temperature. The MD simulations may be maintained at a temperature. The simulated solution conditions may include virtual water molecules. The MD simulations may employ explicit water solvation. The simulated solution conditions may include virtual solute ion for maintaining neutrality.

The MD simulations may calculate a mean root square of fluctuation of an alpha-carbon (α-carbon) of an amino acid residue (at the "N" position) (RMSF). The amino acid residue may be a residue in VH and/or VL amino acid sequence. The amino acid residue may be a residue in a CDR amino acid sequence. The amino acid residue may be a residue in a framework region (FR). The amino acid residue may be an aspartic acid residue. The amino acid residue may be a tryptophan residue. The amino acid residue may be any potentially labile residue.

The structural parameters may include a time-averaged SASA of an amino acid residue. The MD simulations may calculate a time-averaged SASA of the residue. The amino acid residue may be an aspartic acid residue. The amino acid residue may be a tryptophan residue. The amino acid residue may be an amino acid residue immediately adjacent to a potentially labile residue.

The structural parameters may include a time-averaged SASA of a main-chain nitrogen atom immediately adjacent to the amino acid residue that occupies the N position. The MD simulations may calculate a time-averaged SASA of a main-chain nitrogen atom immediately adjacent to the residue at the N position along an amino acid sequence. The amino acid residue at the N position may be an Asp residue. "Immediately adjacent" may be defined as adjacent along the amino acid sequence in a direction toward either the amino-terminus (N-terminus) or the carboxyl-terminus (C-terminus) of the amino acid sequence. The amino acid residue immediately adjacent to the residue at the residue at the N position may be adjacent along the amino acid sequence in a direction toward the C-terminus of the amino acid sequence (i.e., the "N+1" position). For example, if the residue is an aspartic acid residue occupying position "N", position "N+1" may be the position of the residue immediately adjacent to the aspartic acid residue along the amino acid sequence in a direction toward the C-terminus of the amino acid sequence. The residue at "N+1" may be glycine. The residue at "N+1" may be threonine. The residue at "N+1" may be aspartic acid. The residue at "N+1" may be alanine. The residue at "N+1" may be any residue.

The MD simulations may calculate different values of the structural parameters for different solution conditions.

Design Criteria

Each of the physiochemical characteristics may have a corresponding design criterion. The design criterion may be a limit, a threshold or a cut-off value. As described below, depending on the physiochemical characteristics and corresponding objective functions, when an index corresponding to the physiochemical characteristic is below the limit, above the limit, not exceeding the limit, or not less than the limit, the design criterion may be deemed satisfied. In certain particular embodiments, the index corresponding to the physiochemical characteristic is below the limit. Depending on the physiochemical characteristics and objective functions, the index may be further converted, e.g., to give a binary indication that signals whether or not the physiochemical characteristic of the antibody satisfies the design criterion.

The design criterion may be a viscosity limit. The design criterion may be a pharmacokinetic clearance rate limit. The design criterion may be a lability limit. The design criterion may be an aspartic acid lability limit. The design criterion may be a tryptophan lability limit. The design criterion may be a stability limit. The design criterion may be a shelf-life limit. The design criterion may be for a therapeutic agent. The design criterion may be for a non-therapeutic agent. The design criterion may be for a composition including the antibody. The composition may be a composition for an in vivo or in vitro application.

The design criterion may be for a particular class (or subclass) of antibody. The class may be IgG. The class (subclass) may be IgG1 or IgG4.

The design criterion may be a criterion associated with manufacturing of the antibody. The design criterion may be a criterion associated with fluid transfer of the antibody. The design criterion may be a criterion associated with storage of the antibody. The design criterion may be a criterion associated with shelf-life of the antibody. The design criterion may be a criterion associated with dosing of the antibody. The design criterion may be a criterion associated with plasma half-life of the antibody. The design criterion may be a criterion associated with clearance rate of the antibody. The design criterion may be a criterion associated with dispensing of the antibody. The design criterion may be for a therapeutic agent including the antibody. The administration or dispensing of the therapeutic agent may be self-administered by a patient. The administration may be intravenous, intraperitoneal, or subcutaneous administration.

Objective Functions

In certain aspects, the invention provides methods for determining whether an antibody has a physiochemical characteristic that satisfies a design criterion. The methods may include quantifying or calculating an index from an objective function that corresponds to a physiochemical characteristic. The objective function may include a value of a calculated structural parameter as described throughout the application.

The objective function may include a summation of multiplicative products of objective function scaling factors and values of corresponding structural parameters. The summation may be included in an argument of an exponential term in the objective function. The objective function may yield a prediction of a value of the physiochemical characteristic, which may be compared with the design criterion. For example, the viscosity objective function may comprise a summation of multiplicative products of values of sequence-based structural parameters according to the invention and of corresponding objective function scaling factors, where the mAb structural attributes contributing to viscosity may be net charge, charge asymmetry and hydrophobicity of at least a portion of the antibody variable domain. The calculation of the objective function yields a viscosity index. The index may be converted to a viscosity value and the comparison of the viscosity value and the viscosity limit set by the design criterion may be used to determine whether the antibody has a viscosity that satisfies the design criterion.

The structural parameters and the corresponding scaling factors of a particular objective function may depend on the class (or subclass) of the antibody. For example, the viscosity objective function described in the preceding paragraph may be used for prediction of viscosity of an IgG1 antibody, while for an IgG4 antibody, the summation may further comprise a product of a constant region net charge or a constant region charge asymmetry and a corresponding objective function scaling factor, depending on the physiochemical characteristics of the antibody of interest.

The objective function may yield a value that does not correspond to a value that is directly relatable or convertible to a physiochemical characteristic; however, the value may nevertheless indicate whether the antibody has a physiochemical characteristic that satisfies a design criterion. The value may be converted to a binary code that indicates whether or not the antibody has a physiochemical characteristic that satisfies a design criterion. For example, an index between zero and one calculated from the aspartic acid lability objective function may be rounded to a single significant figure to produce a second index, wherein the antibody is determined to satisfy the aspartic acid lability design criterion when the second index is zero, and to not satisfy the aspartic acid lability design criterion when the second index is one.

The logical processing device may derive the index by processing the calculation of the objective function.

The objective function may have the form of any suitable polynomial or probability density function employed, modified and/or derived by the mathematical analytical methods implemented herein.

Objective functions corresponding to different physiochemical characteristics may have different functional forms.

Objective Function Scaling Factors

The methods may include selecting the scaling factors. Selecting the scaling factors may include selecting the scaling factors from a set of scaling factors. "Scaling factors" may also be referred to as "coefficients."

The scaling factor sets may include scaling factors for each of one or more antibody classes. The antibody class may include IgG, IgA, IgE, IgM and IgD. The antibody class may also include subclass; unlimited examples of subclass include IgG1, IgG2, IgG3 and IgG4. The antibody class may be IgG. The antibody class may be IgG1. The antibody class may be IgG4.

The scaling factor set may include for each class (or subclass) a set of scaling factors for each of one or more solution conditions. The solution conditions may be simulated solution conditions, as may be used for MD simulations. The solution conditions may be actual, wet solution conditions.

The scaling factor set may include for each class (or subclass), and for each solution condition, a scaling factor corresponding to each of the structural parameters.

The scaling factor set may be stored in the machine-readable memory. The logical processing device may select the scaling factors. Selecting the scaling factors may include retrieving the scaling factors from the machine-readable memory. The logical processing device may retrieve the scaling factors from the machine-readable memory.

Selecting the scaling factors may include deriving the scaling factors. The scaling factors may be derived by fitting the objective function to empirical values of the physiochemical characteristics of a set of test antibodies. The scaling factors may be coefficients or constants arrived at by regressing calculated values of structural parameters comprising an objective function against measured values of the physiochemical characteristics of a training set of antibodies (also referred to herein as "test antibodies") under each of the different solution conditions. The scaling factors may be derived by any other means of fitting the structural parameters comprising an objective function to the measured values of the physiochemical characteristics. The logical processing device may fit the structural parameters of an objective function to the measured values of the physiochemical characteristics. Once derived, the same scaling factor set may apply to prediction of viscosity or Asp isomerization or other physiochemical characteristic of antibodies of the same class or subclass under the same conditions.

The measured values may be empirical values. The measured values may be publicly documented or published values. The measured values may be electronically encoded. The measured values may be stored in the machine-readable memory.

Physiochemcial Characteristic Indicies

For one or more of the physiochemical characteristics, an index may be computed from the corresponding objective functions. The index may correspond to the physiochemical characteristic. The index may be compared to the design criterion.

The index may be electronically calculated. The term "electronically calculated" or "electronically quantified" may refer to computational derivation by an electronic computing device, such as the logical processing device.

The logical processing device may perform the computation. The logical processing device may perform the comparison. The data transmitting device may output an indication that the index satisfies the design criterion.

The logical processing device may select the antibody from two or more candidate-antibodies based on indices corresponding to the candidate-antibodies. The selection may select the candidate-antibody whose index conforms to or better conforms to the limit of a physiochemical characteristic or the design criterion.

The index may be the basis for determining whether to manufacture or produce the antibody.

The index may be the basis for determining whether or how to modify the pre-existing antibody. The index may be the basis for modifying the pre-existing antibody to produce the target antibody having one or more physiochemical characteristics that are improved from those of the pre-existing antibody and/or that satisfy one or more design criteria.

Antibodies

One or more of the antibody, the test antibodies, the candidate-antibodies, the pre-existing antibody and the target antibody may include a monoclonal antibody (mAb), a polyclonal antibody, a class-switched antibody or any other type of antibody.

One or more of the antibody, the test antibodies, the candidate-antibodies, the pre-existing antibody and the target antibody may include an antibody fragment, a single-chain fragment variable antibody, a single-domain antibody, or any other type of fragment or antibody.

One or more of the antibody, the test antibodies, the candidate-antibodies, the pre-existing antibody and the target antibody may include a human antibody, a non-human antibody, a chimeric antibody, a humanized antibody, an engineered antibody, an artificial antibody or any other type of antibody.

One or more of the antibodies, the test antibodies, the candidate-antibodies, the pre-existing antibodies and the target antibodies may belong to an antibody class. The class may be IgG, IgM or any other suitable class. The class may be a switched class. The class may include one or more subclasses. The subclass may be IgG1. The subclass may be IgG4. The subclass may be any subclass.

The term "antibody" herein is used in the broadest sense and encompasses various antibody structures, including but not limited to monoclonal antibodies, polyclonal antibodies, multispecific antibodies (e.g., bispecific antibodies), and antibody fragments. An "antibody fragment" refers to a molecule other than an intact antibody that comprises a portion of an intact antibody that binds the antigen to which the intact antibody binds.

The term "variable region" or "variable domain" refers to the domain of an antibody heavy or light chain that is involved in binding the antibody to antigen. The variable domains of the heavy chain and light chain (VH and VL, respectively) of an antibody generally have similar structures, with each domain comprising four conserved framework regions (FRs) and three hypervariable regions (HVRs or CDRs). (See, e.g., Kindt et al. Kuby Immunology, 6$^{th}$ ed., W.H. Freeman and Co., page 91 (2007).) A single VH or VL domain may be sufficient to confer antigen-binding specificity.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3).

"Framework" or "FR" refers to variable domain residues other than HVR residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3(L3)-FR4.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method.

The "class" of an antibody refers to the type of constant domain or constant region possessed by its heavy chain. There are five major classes of mammalian antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. As used herein, "classes" of antibodies broadly include classes and subclasses of antibodies.

Antibody Production

In certain aspects, the invention further provides methods of producing an antibody wherein the antibody obtained is determined to have one or more physiochemical characteristics that satisfy one or more design criteria. The invention may provide methods of producing a target antibody that is modified from a pre-existing antibody not satisfying the design criteria so that the modified antibody, i.e., the produced target antibody, has one or more physiochemical characteristics that satisfy one or more design criteria. The production may be for small scale antibody preparation or for large scale antibody manufacturing.

The antibody produced may be further included in a pharmaceutical composition. Pharmaceutical formulations of an antibody are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The formulation herein may also contain more than one active ingredient as necessary for the particular indication being treated, preferably with those ingredients having complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

The monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci.

Antibodies may be produced by any methods known in the art. The antibody may be produced by a method of culturing a host cell comprising nucleic acid encoding the antibody under conditions suitable for expressing the antibody. The antibody may be produced recombinantly in the host cell. The host cell may be a prokaryotic cell (including, without limitation, an *E. coli* cell) or a eukaryotic cell (including, without limitation, an insect cell such as an SF9 cell or a mammalian cell such as a Chinese Hamster Ovary cell). The antibody may be produced by a transiently transfected cell or a stably transfected cell line. The antibody may be produced in a transgenic animal. The antibody may be produced by any synthetic method known in the art. The antibody may be obtained by purification using standard methods such as chromatography methods.

The term "pre-existing antibody" may refer to the antibody of which the amino acid sequence is modified so that one or more physiochemical characteristics determined according to the instant invention are improved and/or satisfy one or more design criteria. The pre-existing antibody may have acceptable antigen-binding specificity, affinity and other effector activities. The pre-existing antibody may have undesirable or unacceptable physiochemical characteristics as determined by the instant invention.

The term "target antibody," "modified antibody" or "mutagenized antibody" may be used interchangeably. These terms may refer to an antibody with one or more changes to the amino acid sequence of the pre-existing antibody so that the target, modified or mutagenized antibody has one or more physiochemical characteristics that satisfy one or more design criteria, and at the same time, at least substantially retains the antigen-binding affinity, specificity and other desirable activities, such as antibody-dependent cell-mediated cytotoxicity (ADCC) and other effector activities of the pre-existing antibody. The target, modified or mutagenized antibody may exhibit one or more properties superior to the pre-existing antibody, for example, improved antigen-binding affinity, specificity and/or other desired activities.

Modifying the pre-existing antibody may include modifying an amino acid sequence of the pre-existing antibody. The amino acid sequence of the pre-existing antibody may be modified to conform to a target amino acid sequence that conforms to the design criterion.

Modifying the amino acid sequence of the pre-existing antibody may include adjusting one or more amino acids in a pre-existing antibody amino acid sequence. Adjusting one or more amino acid residues may include chemical modification of one or more residues. Chemical modification of one or more residues may include changing chirality of one or more residues. Chemical modification of one or more residues may include changing one or more atoms of one or more residues.

Modifying the amino acid sequence of the pre-existing antibody may include replacing or substituting one or more amino acids residues in the pre-existing antibody amino acid sequence with a different amino acid residue. Modifying the amino acid sequence of the pre-existing antibody may include deleting one or more amino acids residues from the pre-existing antibody amino acid sequence. Modifying the amino acid sequence of the pre-existing antibody may include adding or inserting one or more amino acid residues to the pre-existing antibody amino acid sequence.

An amino acid substitution may be a conservative substitution or a non-conservative substitution. It is generally understood in the art what constitutes conservative or non-conservative amino acid substitution. Conservative substitutions are shown in Table 1 below under the heading of "preferred substitutions." More substantial changes are provided in Table 1 under the heading of "exemplary substitutions," and as further described below in reference to amino acid side chain classes. Amino acid substitutions may be introduced into the pre-existing antibody to produce a modified antibody, i.e., a target antibody. The modified antibody may be screened for a desired attribute, e.g., a desired physiochemical characteristic, in addition to its retention of the desired attributes of the pre-existing antibody.

TABLE 1

| Original Residue (1-letter abbreviation) | Exemplary Conservative Substitutions | Preferred conservative Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. Non-conservative substitutions will entail exchanging a member of one of these classes for another class.

It may be within the ability of a researcher to increase or decrease net charge or hydrophobicity in accordance with the instant invention by substituting one or more amino acid residues in the antibody sequence, so that the antibody may have a physiochemical property that satisfies a design criterion. For example, a substitution from a basic amino acid residue to an acidic or neutral amino acid residue may decrease calculated net charge, and a substitution from a hydrophilic amino acid residue to a hydrophobic amino acid residue may increase calculated hydrophobicity, of a relevant index as the basis for determining whether the antibody satisfies a certain design criterion. The target, modified or mutagenized antibody may be subjected to further in-silico analysis or wet experimental analysis to confirm that the target, modified or mutagenized antibody does have at least one physiochemical property that satisfies a design criterion.

The target, modified or mutagenized antibody may be subjected to further analysis to ensure that the modified antibody at least substantially retains a desired activity of the pre-existing antibody such as antigen-binding specificity or affinity using methods known in the art. For example, antigen-binding specificity, affinity and binding kinetics may be measured by ELISA, fluorescence-based immunoassay, radioimmunoassay or BIACORE® assay (Biacore AB, Uppsala, Sweden).

The term "substantially retains" an activity may refer to retaining at least 80%, 81%, 82%, 83%, 84%, 85%, 86%, 87%, 88%, 89%, 90%, 91%, 92%, 93%, 94%, 95%, 96%, 97%, 98%, or 99% of the activity.

Logical Processing Devices, Data Transmitting Devices, Data Receiving Devices

One or more of the logical processing devices, data transmitting devices and data receiving devices may be implemented as, or part of, a computing machine.

The computing machine may be a client, a server, both a client and a server, a programmable logic controller ("PLC"), or any other suitable processing device. The computing machine may include a central processing unit ("CPU"), memory and input/output ("I/O") circuitry, and/or any other suitable apparatus.

The CPU may include one or more of a microprocessor, a microcomputer and a microcontroller. Microprocessors, microcomputers and microcontrollers may include digital circuitry components such as gates and flip-flops. The CPU may be constructed using one or more discrete digital circuitry components such as flip-flops and gates.

Microprocessors, microcomputers and microcontrollers may conform to one or more architectures, such as reduced instruction set computers ("RISC") or complex instruction set computers ("CISC") or very large instruction words ("VLIW") or any other suitable architecture. The architectures may define the configuration of one or more of a data paths, control circuitry, clock circuitry, memory circuitry, and any other suitable paths or circuit configurations.

The data paths may or may not be pipelined. The data paths may include an arithmetic logic unit ("ALU"). The control circuitry may interpret instructions. The control circuitry may control the data paths. The clock circuitry may govern timing of one or more of the control unit and data paths. The control circuitry may include one or more finite state machines, read-only memory and internal processing units in any suitable combination.

The memory circuitry may supply computational variable values, such as scaling factors. The memory may supply instructions, such as those required to calculate an objective function. The memory may include one or more registers. The memory may include one or more levels of cache. The memory may include addressing components. The addressing components may govern a virtual memory system. The addressing components may govern access to external memory and or memory devices.

The microprocessor may be integrated on a single silicon die together with registers and some or all of the cache. One or more levels of cache may be external to the microprocessor die.

The memory may include one or more of random access memory ("RAM"), read-only memory ("ROM"), Flash memory, electrically erasable programmable memory ("EEPROM"), electrically programmable memory ("EPROM"), magnetic disc, magnetic tape, drums, optical discs and any other suitable memory.

The memory may be divided into "on board" components (e.g., register memory and memory designated as cache), which may be included on the microprocessor die and "external memory" components, which may be external to the microprocessor die. External memory may be part of physically addressable memory (e.g., memory that may be designated as main memory/core memory) or virtually addressable memory. Magnetic disc memory may be used for nonvolatile storage. Magnetic disc memory and may be part of a virtual memory system.

I/O circuitry may be internal or external to the microprocessor die. I/O connectivity may involve direct connection to hardware components (e.g., printers, process-control elements and other suitable hardware components). I/O connectivity may involve one or more networking components (such as wired modems, wireless connectivity WIFI, near-field connection and other suitable networking components) for communication with a network. The network may include nodes in wired communication. The network may include nodes in wireless communication. The networks may include a wide area network ("WAN"), a local area network ("LAN"), a WIFI network, or any other suitable type of network.

For a type of I/O connectivity, information may be sent using a transmitter. For a type of I/O connectivity, information may be received using a receiver. In some cases, the transmitter and receiver may be combined into a transceiver. Typically information is digital information organized in packets. However, information may be a single transmitted bit, such as one that turns on a machine or indicates a state of a process or calculation, a single received bit, such as one that indicates the state of a sensor, a process or a calculation, or it may include analog voltages or currents.

The transmitter may include hardware components. The transmitter may include software components. Hardware may be included to physically interact with wired connectivity or with wireless media through which radio frequency energy propagates. The transmitter hardware may include a radio transmitter. The transmitter may have only hardware components. Portions of the hardware may be external to the microprocessors, microcomputers and microcontrollers. For example, a single bit output may utilize a level shifting amplifier to control a machine. Some transmitter protocols may be updated via software updates.

The receiver may include hardware components. The receiver may include software components. Hardware may be included to physically interact with wired connectivity or with wireless media through which radio frequency energy propagates. The receiver hardware may include a radio receiver. The receiver may have only hardware components. Portions of the hardware may be external to the microprocessors, microcomputers and microcontrollers. For example, a single bit output may utilize a level shifting amplifier to receive data from a sensor. Some receiver protocols may be updated via software updates.

The computing machine may be configured to include means for selecting an objective function corresponding to one or more of the physiochemical characteristics of an antibody.

The computing machine may be configured to include means for identifying in the machine-readable memory (machine memory) values of the objective function scaling factors under the antibody solution conditions. The computing machine may be configured to include means for retrieving the identified scaling factors values.

The computing machine may be configured to include means for processing the antibody structural parameters. The processing may be logical processing. The processing may be numerical processing. The processing may include evaluating the parameters. The processing may produce values of the parameters. The processing may be based on the antibody structural features. The processing may be based on the solution conditions.

The computing machine may be configured to include means for evaluating the objective function. The evaluating may be based on the values of the parameters and the values of the scaling factors. Evaluating the objective function may produce a prediction of value of the one or more physiochemical characteristics of the antibody under the solution conditions.

The computing machine may be configured to include means for comparing the prediction to a design criterion corresponding to the one or more physiochemical characteristics.

The computing machine may be configured to include means for selecting the antibody on the basis of the comparing. The antibody may be selected if the prediction conforms to the design criterion. The antibody may be selected for antibody production.

Combination of Features and Principles of the Invention

Methods for applying the above described features and principles of the invention to exemplary physiochemical characteristics will now be described. The exemplary physiochemical characteristics include viscosity, clearance, aspartic acid lability and tryptophan lability.

It will be understood that the methods may include applying the above described features and principles to one of the physiochemical characteristics or to a combination of two or more of the physiochemical characteristics in any combination with each other.

The methods may be implemented by any combination of features of the apparatus, media, or both.

Viscosity

The physiochemical characteristic may be the viscosity of the antibody. The design criterion may be a viscosity limit. The design criterion may be deemed to be satisfied if the viscosity of the antibody is equal to the viscosity limit. The design criterion may be deemed to be satisfied if the viscosity of the antibody is less than the viscosity limit. The viscosity limit may be 50, 45, 40, 35, 30, 25, 20, 15, 10, or 5 cP. Viscosity-based methods of determining the fitness of the antibody for inclusion in the therapeutic agent, selecting the antibody from several candidate-antibodies, manufacturing the antibody, modifying the pre-existing antibody and producing the target-antibody are discussed below. It will be understood that one or more steps of one of the methods may be performed in combination with one or more steps of the other methods.

Viscosity: Methods for Determining Fitness or Suitability of Antibody for Inclusion in a Therapeutic Agent The methods may include determining, based on viscosity, the fitness of the antibody for inclusion in the therapeutic agent. The methods may comprise (a) calculating from the antibody structural information that may comprise: (1) a net charge; and (2) a charge asymmetry; (b) selecting for the antibody: a first scaling factor (or a net charge scaling factor) that corresponds to the net charge, and a second scaling factor (or a charge asymmetry scaling factor) that corresponds to the charge asymmetry; (c) calculating an index from an objective function comprising the scaling factors, the index corresponding to viscosity; (d) comparing the index to a design criterion; and (e) determining whether the antibody has the viscosity that satisfies the design criterion.

The calculating from the structural information may comprise calculating from information of a primary structure. The primary structure may comprise a light chain variable domain (VL) amino acid sequence and a heavy chain variable domain (VH) amino acid sequence. The methods may include calculating the net charge from structural information of a variable domain. The net charge may comprise a sum of a net charge of the VL amino acid sequence and a net charge of the VH amino acid sequence. The methods may include calculating the charge asymmetry from structural information of the variable domain. The charge asymmetry may comprise an arithmetic product of the net charge of the VL amino acid sequence and the net charge of the VH amino acid sequence. The method may further comprise calculating (3) from one or more complementarity determining regions, a hydrophobicity.

The method may further comprise the step of sequencing the amino acid sequence of the antibody. The method may further comprise the step of producing the antibody.

The methods may include calculating the hydrophobicity from structural information of a single complementarity determining region of the variable domain. The single complementarity determining region may be any one of a CDR1, a CDR2 and a CDR3 of the antibody. The methods may include calculating the hydrophobicity from structural information of one or more complementarity determining regions (CDRs). The one or more complementarity determining regions may include two, three, four, five or six complementarity determining regions. The one or more complementarity determining regions may include six complementarity determining regions. The hydrophobicity may be calculated as a sum of hydrophobicity values of one or more complementarity determining regions. The hydrophobicity may comprise a total of summation functions of values of hydrophobicity of the one or more CDRs. Each of the summation function may be a ratio of a sum of the values of hydrophobic residues of a CDR to a sum of the values of hydrophilic residues of the CDR. The methods may include calculating the hydrophobicity from structural information of an Fv domain. The methods may include calculating the hydrophobicity from structural information of an Fv domain when the training set of antibodies includes antibodies of different classes or subclasses. The value of hydrophobic residue or hydrophilic residue may be the Eisenberg hydrophobicity scale value for a given amino acid residue.

Viscosity may be experimentally measured by using a rheometer, including without limitation, cone-and-plate type and falling ball type rheometer.

The methods may include electronically quantifying the index. The index may be quantified from the objective function. The objective function may include the scaling factors. The index may correspond to the viscosity.

The methods may include comparing the index to the design criterion viscosity limit for determining whether the antibody has the viscosity that satisfies the design criterion viscosity limit.

In the objective function, $\log_{10}$ of the index may depend on the sum:
(the net charge×the first scaling factor) plus
(the charge asymmetry×the second scaling factor) plus
(the hydrophobicity×the third scaling factor).
The objective function may have the general form of index=$10^{constant}10^{sum}$.

The methods may include selecting scaling factors. The scaling factors may include a first scaling factor (or a net charge scaling factor). The first scaling factor may correspond to the net charge. The scaling factors may include a second scaling factor (or a charge asymmetry scaling factor). The second scaling factor may correspond to the charge asymmetry. The scaling factors may include a third scaling factor (or a hydrophobicity scaling factor). The third scaling factor may correspond to the hydrophobicity. The scaling factors may be selected from the set of scaling factors that may include a plurality of first scaling factors, a plurality of second scaling factors and a plurality of third scaling factors. The methods may further comprise deriving the scaling factors from data of at least one viscosity measurement of at least one test antibody, wherein the antibody and the test antibody are of the same antibody class. The scaling factors may be derived scaling factors.

The solution conditions may include ionic strength. For low ionic strength solutions, the third scaling factor may be zero. An example of a low ionic strength solution may be a buffer solution of 20-30 millimolar concentration.

For low ionic strength solutions, the methods may not include calculating the hydrophobicity from the antibody structural information and neither the sum nor the scaling factors may include the third scaling factor. For low ionic strength solutions, the methods may not include selecting the third scaling factor. In the objective function for low ionic strength solutions, $\log_{10}$ of the index may depend on the sum:
(the net charge×the first scaling factor) plus
(the charge asymmetry×the second scaling factor).

For high ionic strength solutions, a close correspondence of the index to the physiochemical characteristic may be achieved by including one, two, three, four, five or six CDRs in calculating the hydrophobicity. An example of a high ionic strength solution may be an ionic buffer of about 200 millimolar concentration.

For example, for a monoclonal IgG1 in an approximately 200 millimolar solution of buffer at about 25° C. and about pH 5.5, first, second and third scaling factors may track with antibody concentration as follows:

for an antibody concentration of about 150 milligrams per milliliter, the first scaling factor may be about −0.036, the second scaling factor may be about −0.012 and the third scaling factor may be about 0.34; and for an antibody concentration of about 180 milligrams per milliliter, the first scaling factor may be about −0.05, the second scaling factor may be about −0.017 and the third scaling factor may be about 0.42.

The term "about" a given value or range may refer to sufficiency of closeness to the value or range to obtain a result substantially similar to that obtained at the value or within the range. A "substantially similar" result may be within 1%, 2%, 3%, 4%, 5%, 6%, 7%, 8%, 9% or 10% of a result obtained at the value or within the range.

For this high ionic strength example, quantification of the index for each of the exemplary antibody concentrations may yield an index closely corresponding to measured viscosity, as measured in centipoise. For some antibody classes and subclasses, the method may include calculating from the constant region structural information of the antibody, a constant region charge asymmetry. For these classes and subclasses, the set of scaling factors may include a plurality of constant region charge asymmetry scaling factors and the methods may include selecting for the antibody a constant region charge asymmetry scaling factor (or a fourth scaling factor) that may correspond to the constant region charge asymmetry. For these classes and subclasses, the objective function may include the constant region charge asymmetry scaling factor. The antibody class (or subclass) may be IgG4.

For these classes and subclasses, $\log_{10}$ of the index may depend on the sum:
(the net charge×the first scaling factor) plus
(the variable domain charge asymmetry×the second scaling factor) plus
(the hydrophobicity×the third scaling factor), and,
depending on the class (or subclass), the constant region charge asymmetry×the constant region charge asymmetry scaling factor).

For these classes and subclasses, for low ionic strength solutions, the third scaling factor may be zero. For low ionic strength solutions, the methods may not include calculating the hydrophobicity from the antibody structural information and neither the sum nor the scaling factors may include the third scaling factor. For low ionic strength solutions, the methods may not include selecting the third scaling factor. In the objective function for low ionic strength solutions, $\log_{10}$ of the index may depend on the sum:
(the net charge×the first scaling factor) plus
(the variable domain charge asymmetry×the second scaling factor) plus
(the constant region charge asymmetry×the constant region charge asymmetry scaling factor).

Classes and subclasses for which the methods may calculate and utilize a constant region charge asymmetry, and the methods may select and utilize a corresponding constant region charge asymmetry scaling factor, may include IgG4.

Viscosity: Methods of Selecting Among Candidate-Antibodies for Inclusion in a Therapeutic Agent The methods may include selecting the antibody, based on viscosity, from among two or more candidate-antibodies and may include none, some or all steps of the methods for determining viscosity fitness.

The methods may include providing first structural information of a first candidate-antibody. The first structural information may include a first amino acid sequence of the first candidate-antibody. The methods may include providing second structural information of a second candidate-antibody. The second structural information may include a second amino acid sequence of the second candidate-antibody.

The methods may include numerically calculating from the first structural information a first set of structural parameters: (1) a first net charge; (2) a first charge asymmetry; and, (3) a first hydrophobicity. The methods may include numerically calculating from the second structural information a second set of structural parameters: (1) a second net charge; (2) a second charge asymmetry; and, (3) a second hydrophobicity.

The methods may include electronically quantifying a first index from a first objective function. The first objective function may include a first set of scaling factors corresponding to the first set of physiochemical parameters. The first index may correspond to the first candidate-antibody. The first index may correspond to a first viscosity of the first candidate-antibody. The methods may include electronically quantifying a second index from a second objective function. The second objective function may include a second set of scaling factors corresponding to the second set of structural parameters. The second index may correspond to the second candidate-antibody. The second index may correspond to a second viscosity of the second candidate-antibody. The first and second set of scaling factors and objective functions may be the same. The first and second set of scaling factors and objective functions may be different.

Each set of scaling factors may include a net charge scaling factor corresponding to net charge, a charge asymmetry scaling factor corresponding to charge asymmetry and a hydrophobicity scaling factor corresponding to hydrophobicity. For some classes and subclasses of candidate-antibodies, the charge asymmetry scaling factors of the first set and/or the second set of scaling factors may be variable domain charge asymmetry scaling factors.

For certain classes and subclasses of candidate-antibodies, the methods may include calculating, from constant region structural information of the first candidate-antibody and/or of the second candidate-antibody, a first constant region charge asymmetry for the first set of structural parameters and/or a second constant region charge asymmetry for the second set of structural parameters, respectively. An example of such classes and subclasses may be IgG4.

The first objective function and the second objective function may include the scaling factors for the first candidate-antibody and the second candidate-antibody, respectively. For candidate-antibodies in low ionic strength solutions, hydrophobicity scaling factors may be zero. For candidate-antibodies in low ionic strength solutions, the methods may not include calculating hydrophobicities. For candidate-antibodies in low ionic strength solutions, the objective functions may not include hydrophobicity scaling factors.

If the class or subclass of the first candidate-antibody is the class or subclass of the second candidate-antibody, the first set of scaling factors may be identical to the second set of scaling factors. If the solution conditions of the first candidate-antibody are the solutions conditions of the second candidate-antibody, the first set of scaling factors may be identical to the second set of scaling factors.

The first index may satisfy the design criterion viscosity limit. The second index may satisfy the design criterion viscosity limit.

The methods may include selecting the first candidate-antibody or the second candidate-antibody to be the antibody for use in the therapeutic agent based on the relative value of the first index and the second index. The methods may include selecting the first candidate-antibody if the first index is lower than the second index. The methods may include selecting the second candidate-antibody if the second index is lower than the first index. The methods may further comprise the step of comparing the first and or second index with a design criterion. The selected antibody may have a viscosity that satisfies the design criterion.

Viscosity: Methods of Manufacturing a Therapeutic Agent

The manufacturing methods may include setting a viscosity limit for the antibody based on a manufacturing or therapeutic dispensing vessel. Methods of manufacturing the therapeutic agent may include none, some or all steps of the methods for determining viscosity fitness.

The manufacturing methods may include identifying a fluid conducting element in the manufacturing vessel or in the dispensing vessel. The fluid conducting element may include a pipe, a valve, a porous plug or any other fluid conducting element. Any other fluid conducting element may include a tube, a chromatographic medium or a filter. The fluid conducting element may have a fluid flow resistance. The fluid flow resistance may depend on the viscosity of the antibody under the set of aqueous solution conditions of manufacture and/or of dispensing.

The manufacturing methods may include electronically quantifying, from structural information of the antibody, the index corresponding to the viscosity of the antibody. The quantifying may follow the methods of determining viscosity fitness of the antibody.

The methods may include transmitting the antibody through the fluid conducting element only if the index does not exceed the limit. The methods may include manufacturing the antibody only if the index does not exceed the limit.

The methods may include constructing the target-antibody such that the viscosity of the therapeutic agent does not exceed the viscosity limit.

The methods may include determining an amino acid sequence for the target-antibody. The amino acid sequence may correspond to a viscosity index that is below the viscosity limit.

The determining of the amino acid sequence may include electronically quantifying a trial viscosity from a trial-antibody amino acid sequence of the pre-existing antibody. The quantifying may include none, some or all of the steps for determining viscosity fitness of the antibody.

The invention also provides methods of manufacturing a composition comprising an antibody, The methods may include setting a viscosity limit for the antibody based on a fluid flow resistance of a fluid conducting element in a manufacturing vessel, the fluid flow resistance depending on a viscosity of fluid that flows through the element; transmitting structural information of the antibody across a network; receiving across the network an index of a viscosity of the antibody calculated from the structural information; and only if the index does not exceed the viscosity limit, transmitting the antibody through the element for manufacturing the composition.

The method may include setting a viscosity limit for the antibody based on a fluid flow resistance of a fluid conducting element in a manufacturing vessel, the fluid flow resistance depending on a viscosity of fluid that flows through the element; calculating from structural information of the antibody an index of a viscosity of the antibody; and only if the index does not exceed the viscosity limit, transmitting the antibody through the element for manufacturing the composition.

Viscosity: Methods of Producing an Antibody

The methods of producing an antibody that has a viscosity that satisfies a design criterion may comprise the steps of (a) setting a viscosity limit for the antibody; (b) calculating, from structural information of the antibody according to the methods described throughout the application, an index that corresponds to viscosity of the antibody; and determining whether the antibody has a viscosity that satisfies the design criterion; and (c) if the index does not exceed the viscosity limit, producing the antibody.

The methods of producing an antibody that has a viscosity that satisfies a design criterion may comprise the steps of setting a viscosity limit for the antibody, the viscosity limit satisfying the design criterion; transmitting structural information of the antibody across a network; receiving across the network an index that corresponds to viscosity of the antibody, the index calculated from the structural information; determining whether the antibody has a viscosity that satisfies the design criterion; and only if the index does not exceed the viscosity limit, producing the antibody.

For each embodiment described herein, the index is calculated by the method comprising the steps of: calculating from the structural information of the antibody: a net charge and a charge asymmetry; selecting for the antibody: a first scaling factor that corresponds to the net charge, and a second scaling factor that corresponds to the charge asymmetry; and calculating the index from an objective function comprising the scaling factors, the index corresponding to the viscosity. The calculating from the structural information may comprise calculating from information of a primary structure. The primary structure may comprise a light chain variable domain (VL) amino acid sequence and a heavy chain variable domain (VH) amino acid sequence. The net charge may comprise a sum of a net charge of the VL amino acid sequence and a net charge of the VH amino acid sequence. The charge asymmetry may comprise an arithmetic product of the net charge of the VL amino acid sequence and the net charge of the VH amino acid sequence. The method may further comprise deriving the scaling factors from data of at least one viscosity measurement of at least one test antibody, wherein the antibody and the test antibody are of the same antibody class. The selecting the scaling factors may comprise selecting the first scaling factor and the second scaling factor from a set of scaling factors for each of one or more aqueous solution conditions. The objective function, log 10 of the index may comprise the sum of (the net charge×the first scaling factor) plus (the charge asymmetry×the second scaling factor).

For each embodiment described herein, the methods may further comprise calculating from the structural information, from information of one or more complementarity determining regions (CDRs) of the antibody, a hydrophobicity; and selecting a third scaling factor that corresponds to the hydrophobicity, wherein the objective function further comprises the third scaling factor. The hydrophobicity may comprise a total of summation functions of values of hydrophobicity of the one or more CDRs. Each of the summation functions may be a ratio of a sum of values of hydrophobic residues of a CDR and of a sum of values of hydrophilic residues of the CDR. The values may be Eisenberg hydrophobicity scale values. The one or more CDRs may comprise one, two, three, four, five or all six CDRs. The selecting the scaling factors may further comprise selecting the first scaling factor, the second scaling factor and the third scaling factor from a set of scaling factors for each of one or more aqueous solution conditions. The objective function, log 10 of the index may comprise the sum of (the net charge×the first scaling factor) plus (the charge asymmetry×the second scaling factor) plus (the hydrophobicity×the third scaling factor).

For each embodiment described herein, the methods may further comprise the step of mutagenizing one or more amino acid residues of the light chain and/or heavy chain variable region amino acid sequence of the antibody to generate a target antibody when the index exceeds the viscosity limit. The step of mutagenizing the light chain and/or heavy chain variable region amino acid sequence may reduce hydrophobicity, increases net charge, and/or increase or decrease charge asymmetry so that the index of the target antibody does not exceed the viscosity limit. The method may further comprise the step of producing the target antibody.

In additional embodiments, the invention provides antibodies selected, produced and/or determined to satisfy the design criterion of viscosity by the methods and apparatus described herein.

Clearance

The physiochemical characteristic may be the pharmacokinetic clearance rate of the antibody. The design criterion may be a pharmacokinetic clearance rate limit. The design criterion may be deemed to be satisfied if the clearance rate of the antibody is equal to the clearance rate limit. The design criterion may be deemed to be satisfied if the clearance rate of the antibody is less than the clearance rate limit. The clearance rate limit may be 20, 19, 18, 17, 16, 15, 14, 13, 12, 11, 10, 9, 8, 7, 6 or 5 mL/kg/day. The clearance rate limit may be 10 mL/kg/day in Cyno monkeys.

Clearance-rate-based methods of determining the fitness of the antibody for inclusion in the therapeutic agent, selecting the antibody from several candidate-antibodies, manufacturing the antibody, modifying the pre-existing antibody and producing the target-antibody are discussed below. It will be understood that one or more steps from one of the methods may be performed in combination with one or more steps of the other methods.

Clearance: Methods for Determining Fitness or Suitability of Antibody for Inclusion in a Therapeutic Agent The methods may include determining, based on clearance, the fitness of the antibody for inclusion in the therapeutic agent. The methods may include calculating the net charge from the antibody structural information. The net charge range may depend on the aqueous solution conditions. The net charge may conform to a net charge range. The net charge range may be from −4 to 12. The net charge range may be −2 to 6.2. The net charge range may be 0 to 6.2. The net charge range may vary depending on the solution conditions and the sample size of the training set of antibodies.

The methods may include, (a) if the net charge may conform to the net charge range, calculating a hydrophobicity from structural information of one or more CDRs and (i) determining that the antibody has a clearance rate that satisfies the design criterion when the hydrophobicity does not exceed a hydrophobicity limit or (ii) determining that the antibody has a clearance rate that does not satisfy the design criterion when the hydrophobicity is higher than the hydrophobicity limit; and (b) if the net charge does not conform to the net charge range, determining that the antibody has a clearance rate that does not satisfy the design criterion. The structural information may be information of a primary structure. The primary structure may comprise a light chain variable domain (VL) amino acid sequence and a heavy chain variable domain (VH) amino acid sequence. The net charge may be the net charge of VH and VL at pH 5.5. The net charge range may be from about −2.0 to about 6.2. The hydrophobicity limit may be about 4.

The methods may include calculating the hydrophobicity from structural information of a single complementarity determining region of the variable domain. The methods may include calculating the hydrophobicity from structural information of one or more complementarity determining regions as described herein. The plurality of complementarity determining regions may include two, three, four five or six complementarity determining regions. The hydrophobicity may be calculated as a sum of hydrophobicity values of one or more complementarity determining regions. The one or more CDRs may be light chain (LC) CDR1, LC CDR3 and heavy chain (HC) CDR3. The method may further comprising the step of producing the antibody.

The Illustrative Results section and FIGs. disclose correspondence of the index to the clearance rate.

Clearance: Methods of Selecting Among Candidate-Antibodies for Inclusion in a Therapeutic Agent The methods may include selecting the antibody, based on clearance rate, from among two or more candidate-antibodies and may include one or more steps of the methods for determining clearance fitness.

For example, the antibody may be selected from two candidate-antibodies for inclusion in the therapeutic agent. The methods of selection may include providing first structural information of a first candidate-antibody. The first structural information may include a first amino acid sequence of the first candidate-antibody. The methods of selection may include providing second structural information of a second candidate-antibody. The second structural information may include a second amino acid sequence of the second candidate-antibody.

The methods may include calculating from the first structural information a first net charge and, from one or more CDRs of the first candidate-antibody, a first hydrophobicity. The methods may include calculating from the second structural information a second net charge and, from one or more CDRs of the second candidate-antibody, a second hydrophobicity.

The first net charge range and the second net charge range may depend on the aqueous solution conditions. The first net charge range and the second net charge range may depend on the class or subclass of the first candidate-antibody and the class or subclass of the second candidate-antibody, respectively. The first and second net charge range may be the same. The first and second net charge range may be different.

The methods may include selecting the first candidate-antibody or the second candidate-antibody to be the antibody for use in the therapeutic agent based on the relative value of the first index and the second index. The methods may include selecting the candidate-antibody that has a lower hydrophobicity than other candidate-antibody or candidate-antibodies. The methods may include selecting the candidate-antibody that has a clearance rate that satisfies the design criterion.

Clearance: Methods of Manufacturing a Therapeutic Agent

The manufacturing methods may include setting a clearance rate limit for the antibody based on a maintenance dose. Methods of manufacturing the therapeutic agent may include one or more steps of the methods for determining clearance rate fitness.

The manufacturing methods may include identifying the maintenance dose for the therapeutic agent. The maintenance dose may depend on the pharmacokinetic clearance rate of the antibody. The clearance rate may be a clearance rate of the antibody under a set of physiological conditions. The physiological conditions may be encountered in therapeutic use of the antibody.

The methods may include manufacturing or producing the antibody only if the antibody has a clearance rate that does not exceed the limit. The method may comprise transmitting structural information of the antibody across a network; receiving across the network a net charge of the antibody, the net charge calculated from the structural information; if the net charge conforms to a net charge range, receiving across the network a hydrophobicity calculated from the structural information, from information of one or more complementarity determining regions (CDRs) of the antibody, and (i) if the hydrophobicity does not exceed a hydrophobicity limit, determining that the antibody has a clearance rate that satisfies the design criterion or (ii) if the hydrophobicity exceeds the hydrophobicity limit, determining that the antibody has a clearance rate that does not satisfy the design criterion; if the net charge does not conform to the net charge range, determining that the antibody has a clearance rate that does not satisfy the design criterion; and only if the antibody is determined to have the clearance rate that satisfies the design criterion, producing the antibody.

The invention also provides methods of producing an antibody that has a clearance rate that satisfies a design criterion, the method comprising: calculating a net charge of the antibody from structural information of the antibody; if the net charge conforms to a net charge range, calculating a hydrophobicity from the structural information, from information one or more complementarity determining regions (CDRs) of the antibody, and (i) if the hydrophobicity does not exceed a hydrophobicity limit, determining that the antibody has a clearance rate that satisfies the design criterion or (ii) if the hydrophobicity exceeds the hydrophobicity limit, determining that the antibody has a clearance rate that does not satisfy the design criterion; if the net charge does not conform to the net charge range, determining that the antibody has a clearance rate that does not satisfy the design criterion; and only if the antibody is determined to have the clearance rate that satisfies the design criterion, producing the antibody.

For each embodiment described herein, calculating from the structural information may comprise calculating from information of a primary structure. The primary structure may comprise a light chain variable domain (VL) amino acid sequence and a heavy chain variable domain (VH) amino acid sequence. The net charge may comprise a sum of a net charge of the VL amino acid sequence and a net charge of the VH amino acid sequence. The net charge may comprise the sum of the net charge of VH and of the net charge of VL, at about pH 5.5. The hydrophobicity may comprise a total of summation functions of values of hydrophobicity of the one or more CDRs. The summation functions may be a ratio of a sum of values of hydrophobic residues of a CDR and of a sum of values of hydrophilic residues of the CDR. The values may be Eisenberg hydrophobicity scale values. The one or more CDRs may comprise one, two, three, four, five or all six CDRs. The one or more CDRs may be light chain (LC) CDR1, LC CDR3 and heavy chain (HC) CDR3. The clearance rate may be no more than about 10 mL/kg/day measured in a cynomolgus monkey model. The net charge range may be from about −2.0 to about 6.2. The hydrophobicity limit may be about 4.

The methods may include mutagenizing one or more amino acid residues of a pre-existing antibody to generate a target-antibody such that the clearance rate of the target antibody does not exceed the clearance rate limit. The methods may further comprise the steps of increasing or decreasing the net charge so that the net charge of the target antibody conforms to the net charge range and/or increasing or decreasing hydrophobicity so that the hydrophobicity of the target antibody does not exceed the hydrophobicity limit.

The methods may include determining an amino acid sequence for the target-antibody. The methods may further comprise the step of producing the target antibody.

In additional embodiments, the invention provides antibodies selected, produced and/or determined to satisfy the design criterion of clearance by the methods and apparatus described herein.

Aspartic Acid Lability

The physiochemical characteristic may be the aspartic acid (Asp) lability of the antibody. The Asp lability may correspond to an isomerization of the Asp residue. The Asp residue may be in a CDR of the antibody. The design criterion may be an Asp lability limit. The design criterion may be deemed to be satisfied if the Asp lability of the antibody is equal to the Asp lability limit. The design criterion may be deemed to be satisfied if the Asp lability of the antibody is less than the Asp lability limit. The Asp lability limit may be 10, 9, 8, 7, 6, 5, 4, 3, 2, 1% or less. The Asp lability limit may be 10, 9, 8, 7, 6, 5, 4, 3, 2, 1% or less over two weeks at 40° C. The Asp lability limit may be 5% or less over two weeks at 40° C.

Asp-lability-based methods of determining the fitness of the antibody for inclusion in the therapeutic agent, selecting the antibody from several candidate-antibodies, manufacturing the antibody, modifying the pre-existing antibody and producing the target-antibody are discussed below. It will be understood that one or more steps from one of the methods may be performed in combination with one or more steps of the other methods.

Asp Lability: Methods for Determining Fitness of Antibody for Inclusion in a Therapeutic Agent The methods may include determining, based on Asp lability, fitness of the antibody for inclusion in the therapeutic agent. The methods may include (a) calculating from the antibody structural information: (1) a fluctuation of the Asp α-carbon, (2) a time-averaged SASA of the Asp residue and (3) a time-averaged SASA of a main-chain nitrogen atom associated with a residue immediately adjacent to the Asp residue. The main-chain nitrogen atom may be associated with a residue immediately adjacent in sequence to the Asp residue; (b) selecting for the antibody (i) a fluctuation scaling factor, (ii) an aspartic acid residue surface area scaling factor, and (iii) a main-chain nitrogen atom surface area scaling factor; (c) calculating an index from an objective function comprising the scaling factors, the index corresponding to the aspartic acid lability; and (d) determining whether the antibody has the aspartic acid lability that satisfies the design criterion. The calculating may use MD simulations. The MD simulations may employ the set of simulated solution conditions and may employ explicit water solvation.

The Asp residue may be in a CDR. The amino acid residue immediately adjacent to the aspartic acid residue is at an N+1 position relative to the aspartic acid residue at the N position.

The methods may include selecting scaling factors. The scaling factors may be derived scaling factors. The scaling factors may include a fluctuation scaling factor corresponding to the Asp α-carbon fluctuation. The scaling factors may include an Asp SASA scaling factor corresponding to the Asp SASA. The scaling factors may include a main-chain nitrogen atom SASA scaling factor corresponding to the main-chain nitrogen atom SASA. The scaling factors may be selected from the set of scaling factors that may include a plurality of fluctuation scaling factors, a plurality of Asp SASA scaling factors and a plurality of main-chain nitrogen atom SASA scaling factors.

The methods may include electronically quantifying the index. The index may be quantified from the objective function. The objective function may include the scaling factors. The index may correspond to the Asp lability.

The methods may include comparing the index to the design criterion Asp lability limit for determining whether the antibody has the Asp lability that satisfies the design criterion Asp lability limit.

In the objective function, the index may depend on Euler's number (the base e) raised to the sum:
(the Asp α-carbon fluctuation×the fluctuation scaling factor) plus
(the time-averaged Asp SASA×the Asp SASA scaling factor) plus
(the time-averaged solvent accessible SASA of the main-chain nitrogen atom×the main-chain nitrogen atom SASA scaling factor). The objective function may have the general form of index=$e^{constant}e_{sum}$. The objective function may have the general form of index=$1/(e^{constant}e^{sum})$. The objective function may have the general form of index=$1/(1+e^{constant}e^{sum})$.

For example, for a monoclonal IgG1 at a simulated temperature of about 300 K with explicit water solvation and other simulated solution conditions as described in the Exemplary Methods section, the fluctuation scaling factor may be about 3.3; the Asp SASA scaling factor may be about −22.2; and the main-chain nitrogen atom SASA scaling factor may be about 16.0.

The methods may include the index being a first index and the first index being rounded to one significant figure to produce a second index. The second index may be either 1 or zero. The second index being zero may correspond to an indication that the first index satisfies the design criterion lability limit.

Asp Lability: Methods of Selecting Among Candidate-Antibodies for Inclusion in a Therapeutic Agent The methods may include selecting the antibody, based on Asp lability, from among two or more candidate-antibodies and may include one or more steps of the methods for determining Asp lability fitness.

The methods of selection may include providing first structural information of a first candidate-antibody. The first structural information may include a first variable domain amino acid sequence of the first candidate-antibody. The methods of selection may include providing second structural information of a second candidate-antibody. The second structural information may include a second variable domain amino acid sequence of the second candidate-antibody.

The methods may include calculating from the first structural information a first set of physiochemical parameters including: (1) a first fluctuation of a first Asp α-carbon of the first candidate-antibody, (2) a first time-averaged SASA of the first Asp residue and (3) a first time-averaged SASA of a first main-chain nitrogen atom associated with a residue immediately adjacent to the first Asp residue. The first Asp residue may be in a CDR of the first candidate-antibody. The first main-chain nitrogen atom may be associated with a residue immediately adjacent in sequence to the first Asp residue.

The methods may include numerically calculating from the second structural information a second set of physiochemical parameters including: (1) a second fluctuation of a second Asp α-carbon of the second candidate-antibody, (2) a second time-averaged SASA of the second Asp residue and (3) a second time-averaged SASA of a second main-chain nitrogen atom associated with a residue immediately adjacent to the second Asp residue. The second Asp residue may be in a CDR of the second candidate-antibody. The second main-chain nitrogen atom may be associated with a residue immediately adjacent in sequence to the second Asp residue.

The methods may include electronically quantifying a first index from a first objective function. The first objective function may include a first set of scaling factors corresponding to the first set of physiochemical parameters. The first index may correspond to the first candidate-antibody. The first index may correspond to a first Asp lability of the first candidate-antibody. The first Asp lability may correspond to a first aspartic acid isomerization.

The methods may include electronically quantifying a second index from a second objective function. The second objective function may include a second set of scaling factors corresponding to the second set of physiochemical parameters. The second index may correspond to the second candidate-antibody. The second index may correspond to a second Asp lability of the second candidate-antibody. The second Asp lability may correspond to a second aspartic acid isomerization.

Each set of scaling factors may include an $\alpha$-carbon fluctuation scaling factor corresponding to $\alpha$-carbon fluctuation, an Asp SASA scaling factor corresponding to Asp SASA and a main-chain nitrogen SASA scaling factor corresponding to main-chain nitrogen SASA.

The first objective function and the second objective function may include the scaling factors for the first candidate-antibody and the second candidate-antibody, respectively. Under the same simulated solution conditions as the antibody to which are applied the methods of determining Asp lability fitness, the objective functions for the candidate-antibodies may be identical to the objective function utilized in the methods for determining Asp lability fitness for candidate-antibodies of the same class or subclass.

If the subclass of the first candidate-antibody is the class or subclass of the second candidate-antibody, the first set of scaling factors may be identical to the second set of scaling factors. If the solution conditions the first candidate-antibody are the solutions conditions of the second candidate-antibody, the first set of scaling factors may be identical to the second set of scaling factors. If the values of water solvation for the first candidate-antibody and the second candidate-antibody are the same, the first set of scaling factors may be identical to the second set of scaling factors.

The first index may satisfy the design criterion Asp lability limit. The second index may satisfy the design criterion Asp lability limit.

The methods may include selecting the first candidate-antibody or the second candidate-antibody to be the antibody for use in the therapeutic agent based on the relative value of the first index and the second index. The methods may include selecting the first candidate-antibody if the first index is lower than the second index. The methods may include selecting the second candidate-antibody if the second index is lower than the first index. The methods may further comprise the step of measuring the Asp lability of the selected antibody. The methods may further comprise the step of producing the selected antibody.

Asp Lability: Methods of Manufacturing a Therapeutic Agent

The manufacturing methods may include setting an Asp lability limit for the antibody based on, for example, a shelf-life for the antibody. Methods of manufacturing the antibody may include one or more steps of the methods for determining Asp lability fitness. The antibody may be a therapeutic agent or may be included in a therapeutic agent.

The manufacturing methods may include identifying the shelf-life. The shelf-life may depend on an Asp lability of the antibody that may be included in the therapeutic agent. The aspartic acid lability may correspond to aspartic acid isomerization. The design criterion may be a lability limit. The lability limit may be based on a shelf-life. The lability limit may be about 2.5%/week aspartic acid isomerization.

The methods may include manufacturing the antibody only if the index does not exceed the limit, wherein an amino acid sequence of a complementarity determining region (CDR) of the antibody comprises an aspartic acid residue. The method may comprise setting an aspartic acid lability limit for the antibody, the aspartic acid lability limit satisfying the design criterion; transmitting structural information of the antibody across a network; receiving across the network an index that corresponds to aspartic acid lability of the antibody, the index calculated from the structural information; determining whether the antibody has an aspartic acid lability that satisfies the design criterion; and only if the index does not exceed the viscosity limit, producing the antibody.

The methods may comprise setting an aspartic acid lability limit for the antibody, the aspartic acid lability limit satisfying the design criterion; calculating from structural information of the antibody an index that corresponds to aspartic acid lability of the antibody; determining whether the antibody has an aspartic acid lability that satisfies the design criterion; and only if the index does not exceed the aspartic acid lability limit, producing the antibody.

The manufacturing methods may include electronically quantifying, from structural information of the antibody, the index corresponding to the Asp lability of the antibody. The quantifying may follow the methods of determining Asp lability fitness of the antibody.

The index may be calculated by the method comprising the steps of: calculating from the amino acid sequence of the CDR (i) root-mean-square fluctuations of an alpha carbon associated with the aspartic acid residue, (ii) a time-averaged solvent accessible surface area of the aspartic acid residue, and (iii) a time-averaged solvent accessible surface area of a main-chain nitrogen atom associated with an amino acid residue immediately adjacent to the aspartic acid residue; selecting for the antibody (i) a fluctuation scaling factor, (ii) an aspartic acid residue surface area scaling factor, and (iii) a main-chain nitrogen atom surface area scaling factor; and calculating the index from an objective function comprising the scaling factors, the index corresponding to the aspartic acid lability. The amino acid residue immediately adjacent to the aspartic acid residue may be at an N+1 position relative to the aspartic acid residue at the N position. The scaling factors may be derived from data of at least one aspartic acid lability measurement of at least one test antibody. Aspartic acid lability measurement of the at least one test antibody may include incubation of the at least one test antibody at a temperature, followed by application of mass spectrometry and HPLC-based techniques. The selecting the scaling factors may comprise selecting from a set of scaling factors that comprises, for each of one or more aqueous solution conditions (i) a fluctuation scaling factor, (ii) an aspartic acid residue surface area scaling factor; and (iii) a main-chain nitrogen atom surface area scaling factor. The objective function, the index comprises Euler's number raised to the sum of (the fluctuation×the fluctuation scaling factor) plus (the time-averaged solvent accessible surface area of the aspartic acid residue×the aspartic acid residue surface area scaling factor) plus (the time-averaged solvent accessible surface area of the main-chain nitrogen atom×the main-chain nitrogen atom surface area scaling factor). The aqueous solution conditions may comprise temperature, pH, buffer type and ionic strength. The aqueous solution conditions may comprise 20 mM Histidine-Acetate buffer. The aqueous solution conditions may comprise a temperature of about 313 K. The index is a first index and the first index may be rounded to one significant figure to produce a second index, the second index being zero corresponding to the first index not exceeding the viscosity limit and the second index being 1 corresponding to the first index exceeding the viscosity limit. The amino acid residue immediately adjacent to the aspartic acid residue may be selected from the group consisting of glycine, threonine, aspartic acid and alanine. The methods may include constructing the target-antibody such that the Asp lability of the therapeutic agent does not exceed the Asp lability limit.

For each embodiment described herein, the methods may comprise the step of mutagenizing one or more amino acid residue of a pre-existing antibody to generate a target antibody so that the index of the target antibody satisfies the design criterion. The methods may further comprise the step of measuring the Asp lability of the target antibody. The methods may further comprise the step of producing the target antibody.

The methods may include determining an amino acid sequence for the target-antibody. The amino acid sequence may correspond to an Asp lability index that is below the Asp lability limit.

In additional embodiments, the invention provides antibodies selected, produced and/or determined to satisfy the design criterion of aspartic acid liability by the methods and apparatus described herein.

Tryptophan Lability

The physiochemical characteristic may be tryptophan (Trp) lability of the antibody. The Trp lability may correspond to an oxidation of the Trp residue. The Trp residue may be in a CDR of the antibody. The design criterion may be a Trp lability limit. The design criterion may be deemed to be satisfied if the Trp lability of the antibody is equal to the Trp lability limit. The design criterion may be deemed to be satisfied if the Trp lability of the antibody is less than the Trp lability limit. The Trp lability limit may be 45, 40, 35, 30, 25, 20, 15 or 10% oxidation. The Trp lability limit may be defined for the antibody under a set of defined conditions.

Trp-lability-based methods of determining the fitness of the antibody for inclusion in the therapeutic agent, selecting the antibody from several candidate-antibodies, manufacturing the antibody, modifying the pre-existing antibody and producing the target-antibody are discussed below. It will be understood that one or more steps from one of the methods may be performed in combination with one or more steps of the other methods.

Trp Lability: Methods for Determining Fitness of Antibody for Inclusion in a Therapeutic Agent The methods may include determining, based on Trp lability, fitness of the antibody for inclusion in the therapeutic agent. The methods may include calculating from the antibody structural information a time-averaged SASA of a Trp residue in a CDR. The calculating may use MD simulations. The MD simulations may employ the set of simulated solution conditions and may employ explicit water solvation.

The methods may comprise steps of (a) calculating, from the amino acid sequence of a complementarity determining region (CDR) of the antibody, a time-averaged SASA of a tryptophan residue; (b) comparing the time-averaged SASA to a cutoff value; and (c) determining that the antibody has the tryptophan lability that satisfies the design criterion when the time-averaged SASA is less than the cutoff value. The cutoff value may be 80 Å$^2$ tryptophan side chain SASA. The amino acid sequence of the heavy chain variable domain (VH) and the amino acid sequence of the light chain variable domain (VL) may contain only one tryptophan residue.

Alternatively, the methods may include electronically quantifying the index. The index may be quantified from the objective function. The index may correspond to the Trp lability.

The methods may include comparing the index to the design criterion Trp lability limit for determining whether the antibody has the Trp lability that satisfies the design criterion Trp lability limit.

In the objective function, the index may depend on the time-averaged Trp SASA.

The methods may further comprise the step of producing the antibody that has a Trp lability that satisfies the design criterion.

Trp Lability: Methods of Selecting Among Candidate-Antibodies for Inclusion in a Therapeutic Agent The methods may include selecting the antibody, based on Trp lability, from among two or more candidate-antibodies and may include none, some or all steps of the methods for determining Trp lability fitness.

The methods of selection may include providing first structural information of a first candidate-antibody. The first structural information may include a first variable domain amino acid sequence of the first candidate-antibody. The methods of selection may include providing second structural information of a second candidate-antibody. The second structural information may include a second variable domain amino acid sequence of the second candidate-antibody.

The methods may include calculating from the first structural information a first time-averaged SASA of a first Trp residue. The first Trp residue may be in a CDR of the first candidate-antibody.

The methods may include calculating from the second structural information a second time-averaged SASA of a second Trp residue. The second Trp residue may be in a CDR of the second candidate-antibody.

The methods may comprise selecting the first or second antibody if the first or second antibody has a time-averaged SASA of Trp residue that is less than the cut-off value.

The methods may include electronically quantifying a first index from a first objective function. The first index may correspond to the first candidate-antibody. The first index may correspond to a first Trp lability of the first candidate-antibody. The first Trp lability may correspond to a first tryptophan oxidation.

The methods may include electronically quantifying a second index from a second objective function. The second index may correspond to the second candidate-antibody. The second index may correspond to a second Trp lability of the second candidate-antibody. The second Trp lability may correspond to a second tryptophan oxidation.

The first index may satisfy the design criterion Trp lability limit. The second index may satisfy the design criterion Trp lability limit.

The methods may include selecting the first candidate-antibody or the second candidate-antibody to be the antibody for use in the therapeutic agent based on the relative value of the first index and the second index. The methods may include selecting the first candidate-antibody if the first index is lower than the second index. The methods may include selecting the second candidate-antibody if the second index is lower than the first index.

Trp Lability: Methods of Manufacturing a Therapeutic Agent

The manufacturing methods may include setting a Trp lability limit for the antibody. Methods of manufacturing the therapeutic agent may include one or more steps of the methods for determining Trp lability fitness. The Trp lability limit may be based on a shelf-life for the antibody. Tryptophan lability may correspond to tryptophan oxidation. The antibody may be a therapeutic agent.

The manufacturing methods may include identifying the shelf-life. The shelf-life may depend on a Trp lability of the antibody that may be included in the therapeutic agent.

The invention also provides methods for producing an antibody that has a tryptophan lability that satisfies a design criterion, the method comprising transmitting structural information of the antibody across a network; receiving across the network a time-averaged solvent accessible surface area of a tryptophan residue of a complementarity determining region (CDR) of the antibody, the time-averaged solvent accessible surface area calculated from the structural information, from an amino acid sequence of the CDR; comparing the time-averaged solvent accessible surface area to a cutoff value; and determining that the antibody has a tryptophan lability that satisfies the design criterion when the time-averaged solvent accessible surface area is less than the cutoff value; and only if the antibody is determined to have the tryptophan lability that satisfies the design criterion, producing the antibody.

The methods may comprise the step of calculating a time-averaged SASA of a tryptophan residue; comparing the time-averaged SASA to a cutoff value; and determining that the antibody has the tryptophan lability that satisfies the design criterion when the time-averaged SASA is less than the cutoff value. The methods may further comprise producing the antibody that satisfies the design criterion.

For each embodiment described herein, a value of water solvation may be a basis of calculating the time-averaged solvent accessible surface area. The water solvation may be a parameter in computer modeling molecular dynamics simulations. The molecular dynamics simulation may be performed using AMBER simulation software. The cutoff value may be about 80 Å$^2$ tryptophan side chain solvent accessible surface area. The tryptophan side chain solvent accessible surface area may be determined using AREAIMOL software. The amino acid sequences of all six CDRs of the antibody may contain only one tryptophan residue. The method may further comprise the step of measuring the Trp lability when the antibody is determined to have a Trp lability that satisfies the design criterion.

The manufacturing methods may include electronically quantifying, from structural information of the antibody, the index corresponding to the Trp lability of the antibody. The quantifying may follow the methods of determining Trp lability fitness of the antibody.

The methods may include manufacturing the antibody only if the index does not exceed the limit.

The methods may include substituting the Trp residue with another non-Trp residue in the pre-existing antibody to generate a target antibody. The methods may further comprise the step of producing the target antibody.

In additional embodiments, the invention provides antibodies selected, produced and/or determined to satisfy the design criterion of tryptophan liability by the methods and apparatus described herein.

EXAMPLES

Exemplary Methods

It will be understood that the test antibodies may be included in the training set of antibodies discussed below.

It will be understood that the scaling factors may be referred to as "coefficients" is the discussion below.

It will be understood that none of the features described in connection with the exemplary methods or illustrative results is intended to be limited to the exemplary method or illustrative result in connection with which the feature is described. mAbs The mAbs used were exemplary IgG1 monoclonal antibodies obtained by expression in Chinese Hamster Ovary cells and purified by a series of chromatography methods including affinity purification by protein A chromatography and ion-exchange chromatography.

Sequence-Based Structural Parameters

Charge

The net charge for a given sequence at a given pH was calculated by adding up the contribution from all charged amino acids using the known pKa's of the side chains (see, e.g., Berg, J. M., Tymoczko, J. L. & Stryer, L. Biochemistry. (W.H. Freeman, Basingstoke)) and the Henderson Hasselbalch equation. The Cys pKa was not considered assuming all Cys are involved in disulfide formation.

Fv Charge Asymmetry Parameter (FvCAP)

FvCAP was developed to capture the charge asymmetry between the VH and the VL domains. FvCAP was simply calculated by obtaining the product between the net charge on the VH domain and the VL domain. A negative product therefore, would represent charge asymmetry between the two domains, whereas a positive product would represent similar sign of the charges on the two domains.

Hydrophobicity Index (HI)

HI was developed to represent the relative ratio of the hydrophobic amino acids to those of the hydrophilic amino acids. The relative hydrophobic strength of each amino acid was weighted using the Eisenberg hydrophobicity scale in these calculations (see, e.g., Eisenberg, D., Weiss, R. M., Terwilliger, T. C. & Wilcox, W. Hydrophobic moments and protein structure. *Faraday Symposia of the Chemical Society* 17, 109-120 (1982)). All the amino acids with a positive scale value were classified as hydrophobic, whereas, those with negative scale values were classified as hydrophilic.

Figure 16:
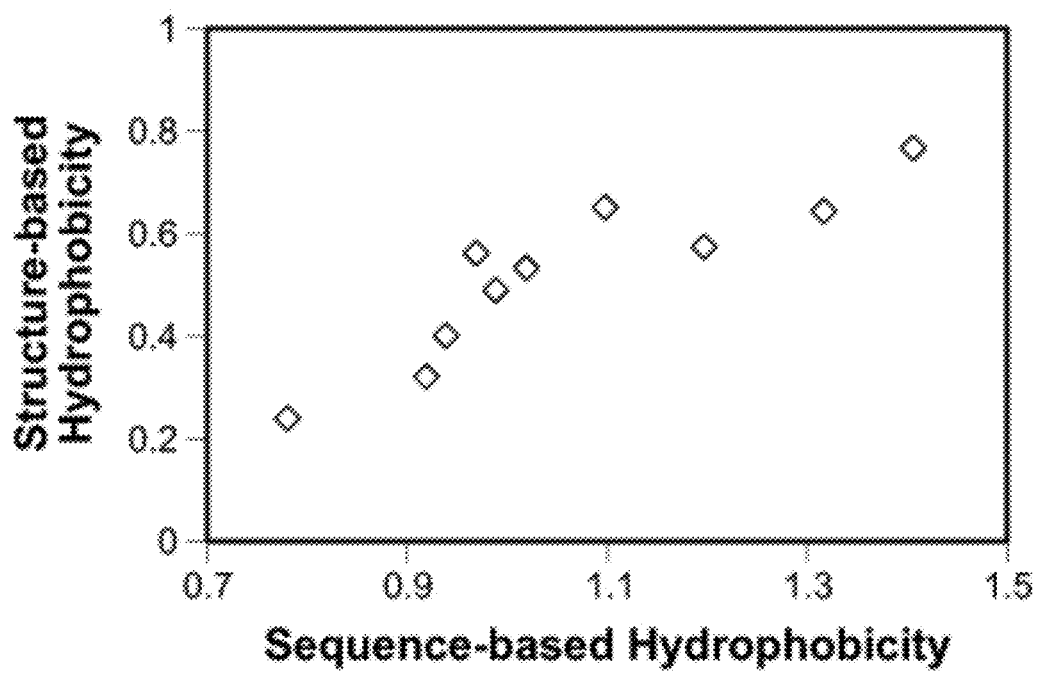

The HI was defined as: $HI=(n_iE_i/n_jE_j)$, where i represents the hydrophobic amino acids, i.e., A, F, I, L, V, W, Y and j represents the hydrophilic amino acids, i.e., D, E, G, H, K, M, N, Q, R, S, T; n is the number of each amino acid and E is the Eisenberg scale value of each amino acid. The calculation may be performed on a 3-D structure of a protein where, in such calculation, the parameter n is replaced by S, where S is defined as the SASA of each amino acid (FIG. 16).

Physiochemical Characteristics

Viscosity

Viscosity measurements were performed using an Anton Paar Physica MCR 501 concentric cylinder cone and plate rheometer (Anton Paar, Graz, Austria). The antibody solutions were adjusted to target concentrations, then 70 μL of each sample protein solution were dispensed onto the sample plate and the cone was lowered. Samples were protected from evaporation and temperature was controlled at 25+/−5° C. Sample viscosity was determined by measuring torque every second for 60 s using a constant shear rate of 1000 s$^{-1}$. Viscosity measurements were reported as an average of the stabilized viscosity measurements using three sample replicates. Sample analysis and data reporting were done with the use of Anton Paar RheoPlus software.

Clearance

Clearance values in Cyno monkeys used in this study were obtained from previously published data (see, e.g. Hötzel, I. et al. A strategy for risk mitigation of antibodies with fast clearance. mAbs 4, 753-760).

MD Simulations

MD Starting Structures

The structures of the Fabs were obtained either from the 3-D crystal structure (if available) or a homology model generated using a local adaption of Modeller (see, e.g., Sali, A. & Blundell, T. L. Comparative Protein Modeling by Satisfaction of Spatial Restraints. *J Mol Biol* 234, 779-815 (1993)). The Fab domain was used as the starting structure for MD before addition of ions (where needed) and explicit solvent molecules.

MD Using GROMACS for Aspartate Isomerization Analysis.

MD simulations of the Fab were carried out with the Gromacs 4.0 simulation software package (see, e.g., Hess, B., Kutzner, C., van der Spoel, D. & Lindahl, E. GROMACS 4: Algorithms for highly efficient, load-balanced, and scalable molecular simulation. *Journal of Chemical Theory and Computation* 4, 435-447 (2008)). The OPLSAA force field (see, e.g., Jorgensen, W. L., Maxwell, D. S. & TiradoRives, J. Development and testing of the OPLS all-atom force field on conformational energetics and properties of organic liquids. *J Am Chem Soc* 118, 11225-11236 (1996); Xu, Z. T., Luo, H. H. & Tieleman, D. P. Modifying the OPLS-AA force field to improve hydration free energies for several amino acid side chains using new atomic charges and an off-plane charge model for aromatic residues. *J Comput Chem* 28, 689-697 (2007)) was used to calculate atomic motions. The charge state of the titrateable residues was evaluated using the empirical method PROPKA (see, e.g. Li, H., Robertson, A. D. & Jensen, J. H. Very fast empirical prediction and rationalization of protein pKa values. *Proteins* 61, 704-721 (2005); Bas, D. C., Rogers, D. M. & Jensen, J. H. Very fast prediction and rationalization of pKa values for protein-ligand complexes. *Proteins* 73, 765-783 (2008)). All the residues were set to their canonical protonation state.

The Fab and Fv fragments were fully solvated with TIP3P (see, e.g., Jorgensen, W. L., Chandrasekhar, J., Madura, J. D., Impey, R. W. & Klein, M. L. Comparison of Simple Potential Functions for Simulating Liquid Water. *J Chem Phys* 79, 926-935 (1983)) water molecules. Approximately 10,000 water molecules were used to solvate the Fv, and 25,500 water molecules were used to solvate the Fab. Chloride or sodium atoms were added to neutralize the overall charge of the system where needed. Octahedral periodic boundary conditions were used in each of the simulations. The electrostatic interactions were calculated using PME (see, e.g., Darden, T., York, D. & Pedersen, L. Particle Mesh Ewald—an N.Log(N) Method for Ewald Sums in Large Systems. *J Chem Phys* 98, 10089-10092 (1993)) with real space electrostatic cut off of 1.0 nm. The Lennard-Jones potential, describing the van der Waals interaction, was cut off at 1.0 nm. The Settle algorithm (see, e.g., Miyamoto, S. & Kollman, P. A. Settle—an Analytical Version of the Shake and Rattle Algorithm for Rigid Water Models. *J Comput Chem* 13, 952-962 (1992)) was used to constrain the bond lengths and angles of the water molecules, Lincs was used to constrain all other bond lengths (see, e.g., Hess, B., Bekker, H., Berendsen, H. J. C. & Fraaije, J. G. E. M. LINCS: A linear constraint solver for molecular simulations. *J Comput Chem* 18, 1463-1472 (1997)), and the vsite algorithm in Gromacs 4.0 was used to remove alkyl and amide hydrogen motions, allowing for a 4 femtosecond (fs) time-step. Throughout these simulations, temperature was kept constant by coupling the system to a temperature bath of 300 K using the V-rescale algorithm (see, e.g., Bussi, G., Donadio, D. & Parrinello, M. Canonical sampling through velocity rescaling. *J Chem Phys* 126, (2007)). During a 200 picosecond (ps) equilibration allowing density of the system to converge, pressure was kept constant by coupling the system to a pressure bath of 1.0 atm (see, e.g., Berendsen, H. J. C., Postma, J. P. M., Vangunsteren, W. F., Dinola, A. & Haak, J. R. Molecular-Dynamics with Coupling to an External Bath. *J Chem Phys* 81, 3684-3690 (1984)). Following equilibration, the simulations were kept at constant volume. Trajectories from these simulations were analyzed with various tools available in GROMACS program suite. All SASAs are calculated using g_sas of GROMACS (see, e.g., Eisenhaber, F., Lijnzaad, P., Argos, P., Sander, C. & Scharf, M. The double cube lattice method: efficient approaches to numerical integration of surface area and volume and to dot surface contouring of molecular assemblies. *J. Comp. Chem.* 16, 273-284 (1995)); mutual information calculation is implemented locally similar to Lange and Grubmüller (see, e.g., Kortkhonjia, E. et al. Solution dynamics of monoclonal antibodies: Experimental and computational approach. mAb In Press (2013); Lange, O. F. & Grubmuller, H. Full correlation analysis of conformational protein dynamics. *Proteins-Structure Function and Genetics* 70, 1294-1312 (2008)); Shannon entropy for φ-ψ distributions is calculated as $S=-\Sigma_{\{\varphi_i,\psi_i,bins\}}p(i,j)\log(p(i,j))$, where p(i,j) is the probability of finding $\{\varphi,\psi\}$ in bin $\{\varphi_i,\psi_j\}$, the bins are defined by a 3° grids and φ-ψ distributions are from g_rama; g_rsmf, g_hbond, and dssp of GROMACS were employed to calculate the root mean square fluctuations, the hydrogen bonds, and the secondary structure status, respectively. The details of the analytical methodology for Shannon entropy and mutual information have been previously published (see, e.g. Kortkhonjia, E. et al. Solution dynamics of monoclonal antibodies: Experimental and computational approach. *mAb* In Press (2013)).

MD Using AMBER for Tryptophan Oxidation Analysis

MD simulations of the Fab fragments were carried out with the Amber 11 simulation software package (see, e.g., D. A. Case, T. A. D., T. E. Cheatham, III, C. L. Simmerling, J. Wang, R. E. Duke, R. Luo, R. C. Walker, W. Zhang, K. M. Merz, B. Roberts, B. Wang, S. Hayik, A. Roitberg, G. Seabra, I. K., K. F. Wong, F. Paesani, J. Vanicek, X. Wu, S. R. Brozell, T. Steinbrecher, H. Gohlke, Q. Cai, X. Ye, J. Wang, M.-J. Hsieh, G. Cui, D. R. Roe, D. H. & Mathews, M. G. S., C. Sagui, V. Babin, T. Luchko, S. Gusarov, A. Kovalenko, and P. A. Kollman University of California, San Francisco; 2011)). The FF99SB fixed-charge force field was used. All residues were set to their canonical protonation state based on their thermodynamic pKa.

The Fab fragments were fully solvated with TIP3P water molecules. Approximately 35,000 water molecules were used to solvate the Fab. Chloride or sodium atoms were added to neutralize the overall charge of the system. Octahedral periodic boundary conditions were used in each of the simulations. The electrostatic interactions were calculated using PME with an electrostatic cut off of 0.8 nm. The SHAKE algorithm was used to remove alkyl and amide hydrogen motions allowing for the use of a time-step of 3 fs.

Throughout these simulations, the temperature was kept constant by coupling the system to a temperature bath of 300 K using Langevin dynamics with a collision frequency of 3/psec. During energy minimization, equilibration, and the subsequent production runs, the pressure was kept constant by coupling the system to a pressure bath of 1.0 atm.

Trajectories from MD simulations were analyzed with publically available tools. All SASAs are calculated using areaimol, a program that is part of the CCP4 program (see, e.g., Bailey, S. The Ccp4 Suite—Programs for Protein Crystallography. *Acta Crystallogr D* 50, 760-763 (1994)). The SASA was determined for each tryptophan side chain, not including peptide backbone atoms.

2,2'-Azobis(2-amidinopropane) dihydrochloride (AAPH)-induced Trp oxidation

AAPH-induced oxidation was carried out by mixing the mAb solution with AAPH at final concentrations of 1 mg/mL and 1 mM, respectively (see, e.g. Ji, J. A., Zhang, B., Cheng, W. & Wang, Y. J. Methionine, tryptophan, and histidine oxidation in a model protein, PTH: Mechanisms and stabilization. *Journal of Pharmaceutical Sciences* 98, 4485-4500 (2009)). The solutions were incubated at 40° C. for 16 hours. The reaction was quenched by addition of 20 mM Met following by buffer exchange into a 20 mM buffer at pH 5.5 using PD-10 desalting columns. The solutions were then analyzed using tryptic digest followed by LC-MS/MS for site specific Trp oxidation. The extracted ion chromatograms of corresponding peptides were manually integrated using an Xcalibur Qual Browser. The relative percentage of oxidation was subsequently calculated by dividing the peak area of the oxidized peptide ions by the sum of the peak areas of oxidized and corresponding non-oxidized peptides Experimental Determination of Asp Degradation Rates The mAb solutions were buffer exchanged using Centricon ultrafiltration tubes with a final formulation of 5 mg/mL protein in a 20 mM buffered solution at pH 5.5, 240 mM sucrose. Samples were placed at 40° C. and withdrawn at t=0, 14 days and 28 days.

LC-MS/MS Tryptic Peptide Mapping

Thermal Stressed samples were analyzed using tryptic peptide digest followed by LC-MS/MS. Protein samples were digested following published protocols with minor modifications (see, e.g., Yu, X. C. et al. Accurate determination of succinimide degradation products using high fidelity trypsin digestion peptide map analysis. *Analytical chemistry* 83, 5912-5919 (2011)).

Peptide mapping was performed on an Agilent 1200 HPLC system equipped with a Jupiter C18 column (Phenomenex, 2.0×250 mm, 5 μm particle size) and coupled to a Thermo Fisher LTQ Orbitrap mass spectrometer. Solvent A consisted of 0.1% TFA in water and solvent B consisted of 0.09% TFA in 90% Acetonitrile. A two-step gradient was used; 0-10% B in 20 minutes followed by 10 to 40% B over 137 minutes. The flow rate was 0.25 mL/min, the column temperature was 55° C. and the protein load was 22 μg. The degradation level at each site was determined by extracted ion chromatography (EIC) using Xcalibur software (see, e.g., Yu, X. C. et al. Accurate determination of succinimide degradation products using high fidelity trypsin digestion peptide map analysis. *Analytical chemistry* 83, 5912-5919 (2011)).

Regression Analysis

Principal Component Regression and Logistic Regression analysis was carried out using XLSTAT® (Addinsoft, New York, N.Y.).

Illustrative Results

Viscosity

Figures 6, 7:
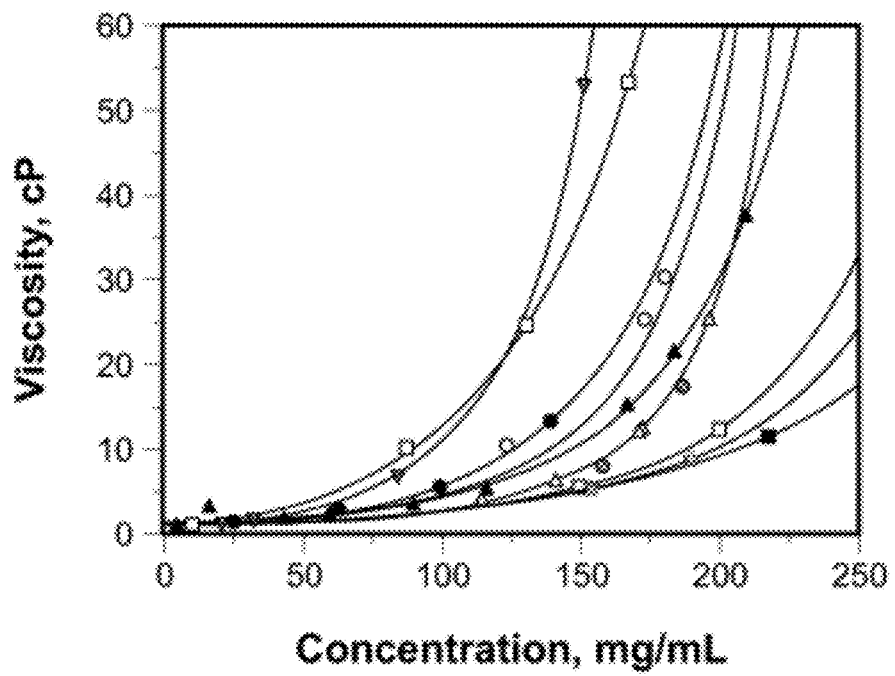
FIG. 6 is a Table of Molecular Properties extracted from MD simulations of Asp residues at various locations "n" along HC and LC (given in Table column Asp) of some of the mAbs of the training set, and the residue at n+1 (given in Table column Seq (N+1) Residue). Properties include SASA of the Asp (SASA_Asp), root-mean-square of an Asp α-carbon fluctuation (RMSF), SASA of the residue at n+1 (SASA(N+1,N)), and measured and predicted value rounded to one significant figure (Binary). (See Detailed Description, below, for other Table column headings.) Rightward forward-slash hatching of a table entry indicates that the entry's value lies within a desired range. Leftward back-slash hatching of a table entry indicates that the entry's value lies outside a desired range.
FIG. 7 shows Viscosity-Concentration profiles of several mAbs in a high ionic strength (200 mM Arginine HCl) buffered solution at pH 5.5. Each set of uniquely shaped data points represents experimental data corresponding to a particular mAb. Profile plot lines were generated using an equation of the form $y=a+be^{cx}$, where y axis is viscosity (in centipoise, cP) and x axis is protein concentration (in mg/mL).

Viscosity may be important for manufacturing and delivery of high concentration mAb solutions (see, e.g., Shire, S. J., Shahrokh, Z. & Liu, J. Challenges in the development of high protein concentration formulations. *Journal of Pharmaceutical Sciences* 93, 1390-1402 (2004)). It was observed that mAbs, differing largely only in the Complementarity Determining Region (CDR) sequence, may exhibit a variety of viscosity-concentration profiles under similar conditions of shear stress (FIG. 7). For similar isotype IgGs, the variable domain Fv (and the CDRs within) may play an important role in defining intermolecular interactions leading to differences in viscosity (see, e.g., Kanai, S., Liu, J., Patapoff, T. & Shire, S. J. Reversible self-association of a concentrated monoclonal antibody solution mediated by Fab-Fab interaction that impacts solution viscosity. *Journal of Pharmaceutical Sciences* (2008); Liu, J., Nguyen, M. D. H., Andya, J. D. & Shire, S. J. Reversible self-association increases the viscosity of a concentrated monoclonal antibody in aqueous solution. *Journal of Pharmaceutical Sciences* 94, 1928-1940 (2005)). One of the aims of the current invention was to determine what parameters may be extracted from the CDRs and Fv to capture the contributing hydrophobic and electrostatic elements (see, e.g., Du, W. & Klibanov, A. M. Hydrophobic salts markedly diminish viscosity of concentrated protein solutions. Biotechnology and Bioengineering 108, 632-636; Yadav, S., Liu, J., Shire, S. J. & Kalonia, D. S. Specific interactions in high concentration antibody solutions resulting in high viscosity. *Journal of Pharmaceutical Sciences* 99, 1152-1168). The focus was on sequence only since this provided the simplest means of data generation and analysis. However, it is noted that any of the parameters as discussed below as calculated from the sequence may be readily calculated from structure as well (FIGS. 15 and 16).

Figure 8A:
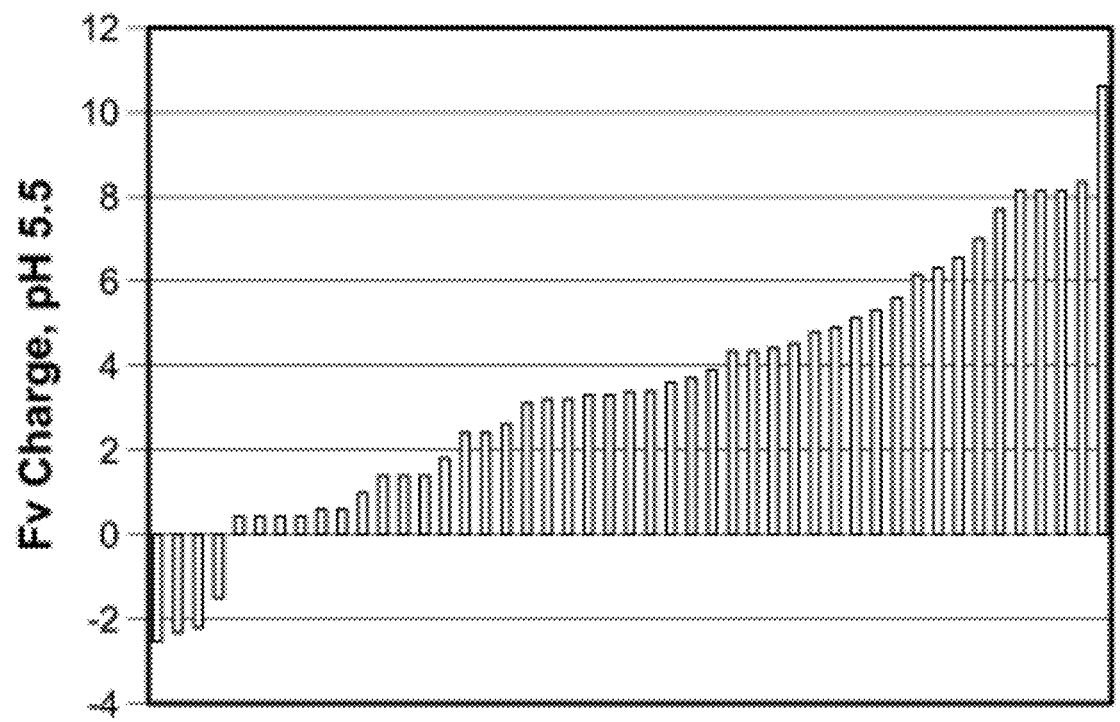
FIGS. 8A-8C show analysis of sequence-based parameters for several mAbs calculated as described in the Examples section, below.
Figure 8B:
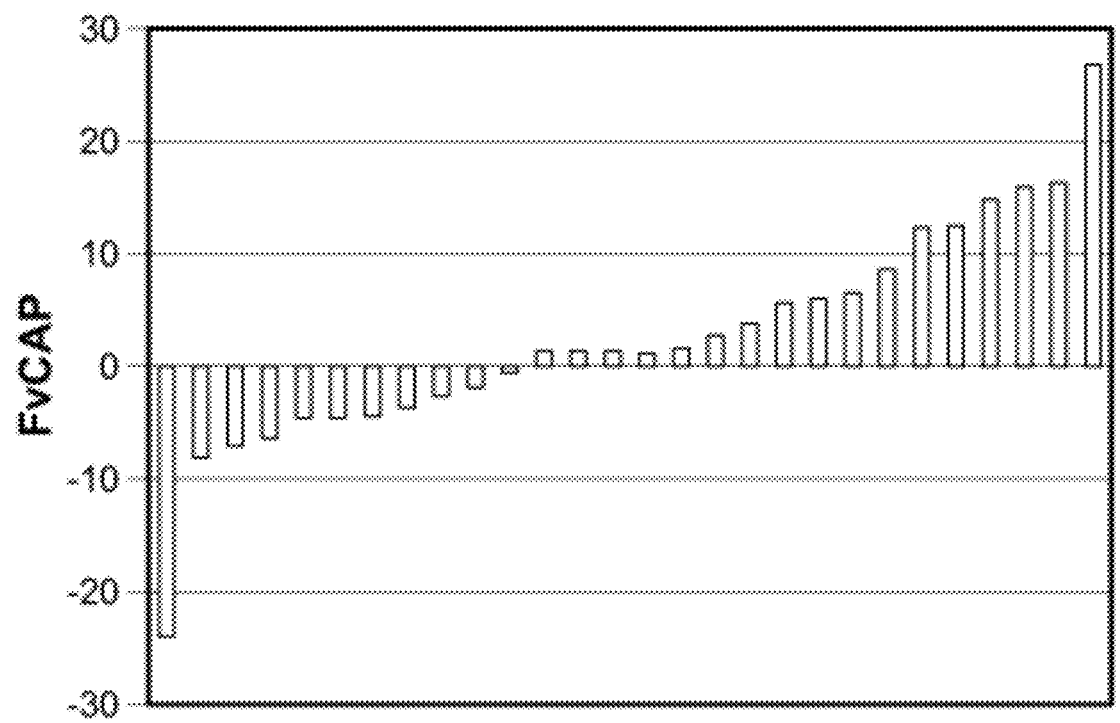
Figure 8C:
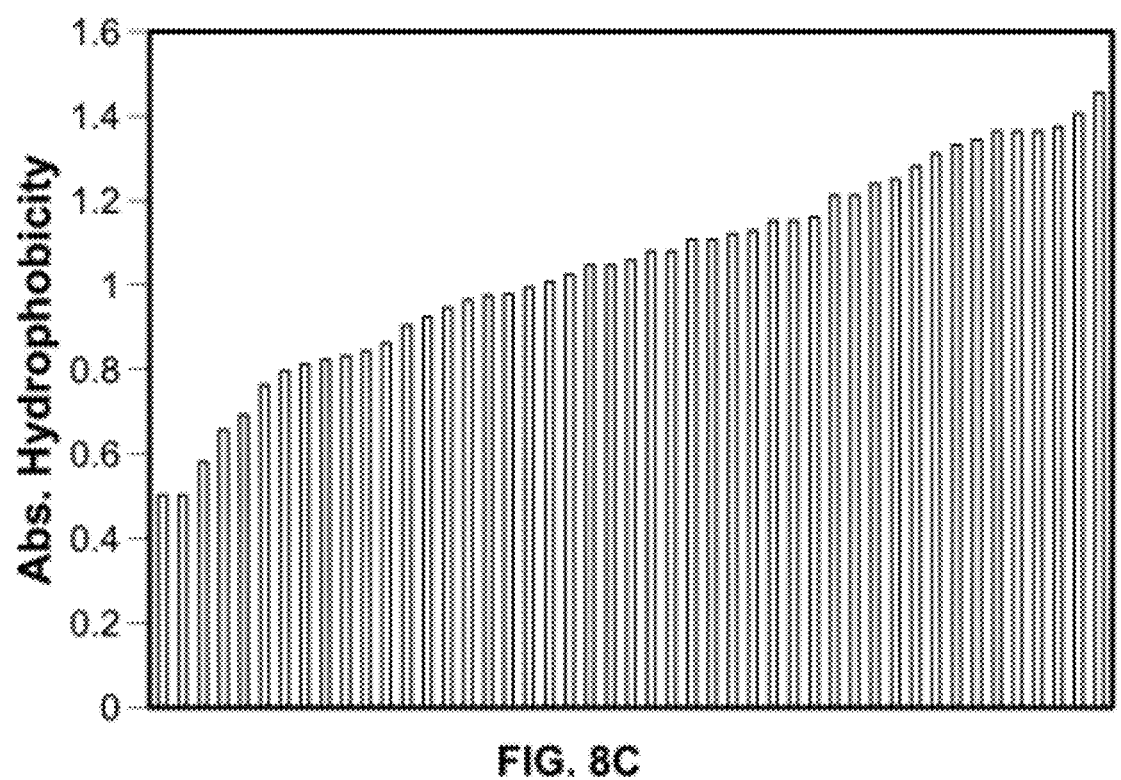

The parameters calculated were: a) net charge of Fv at a given pH (e.g., pH 5.5), b) Fv Charge Asymmetry Parameter (FvCAP), and c) the Hydrophobicity Index (HI) of the CDRs or Fvs. The net charge could potentially contribute to repulsive interactions, whereas FvCAP and HI could contribute to attractive interactions. The FvCAP parameter represents the charge asymmetry between the VH and VL domain. It was hypothesized that opposite net charge between the VH and the VL domain (negative FvCAP) would provide an opportunity for the Fv domain to interact with another Fv domain through a dipole-like interaction or with another charge patch present on the mAb (see, e.g., Yadav, S., Liu, J., Shire, S. J. & Kalonia, D. S. Specific interactions in high concentration antibody solutions resulting in high viscosity. *Journal of Pharmaceutical Sciences* 99, 1152-1168; Yadav, S. et al. Establishing a Link Between Amino Acid Sequences and Self-Associating and Viscoelastic Behavior of Two Closely Related Monoclonal Antibodies. *Pharmaceutical Research* 28, 1750-1764). A larger negative FvCAP value was expected to lead to stronger attractive interactions compared to smaller negative or positive values. It is noted that the actual structural conformation could distribute the charge asymmetry in a way that may not be captured as defined above by the sequence, yet, in the calculations, the sequence-based approach as the first approximation provided a simpler means to capture the lack of charge symmetry at least in one dimension. When compared for a number of mAbs (FIGS. 8A-8C), a wide range of these parameters was observed, even though the primary difference in the sequence lies in the CDR region (all mAbs of IgG1 isotype). The HI values calculated from CDRs trend the same as those calculated from Fv (FIG. 17), therefore the former were used for further analysis.

Figure 9A:
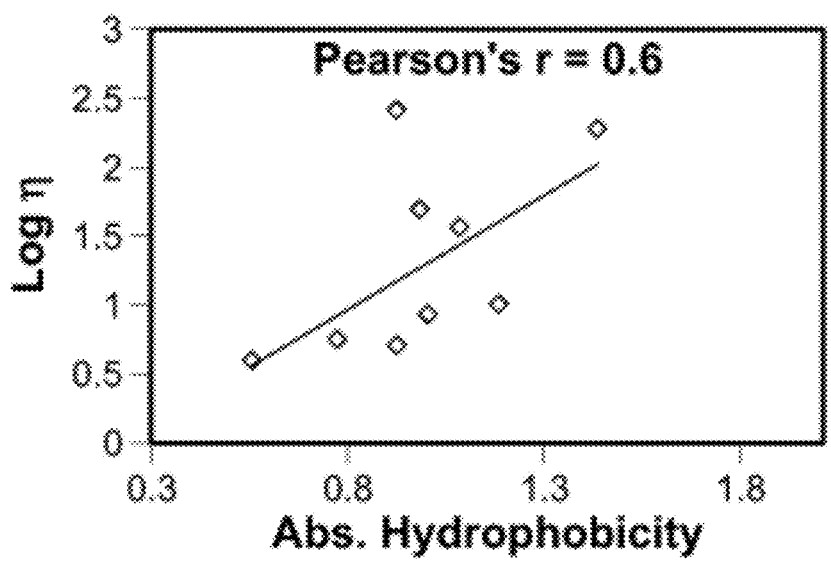
FIGS. 9A-9C show plots of correlation of log viscosity with calculated sequence-based structural parameters.
Figure 9B:
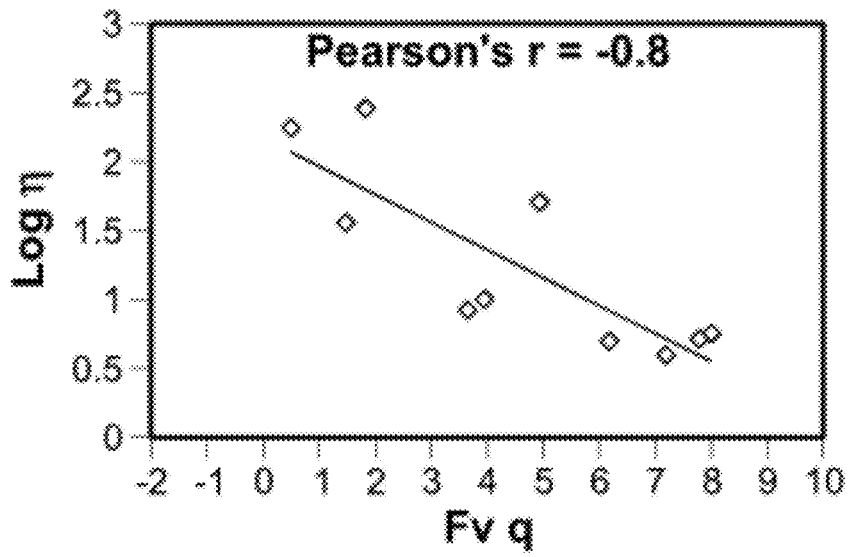
Figure 9C:
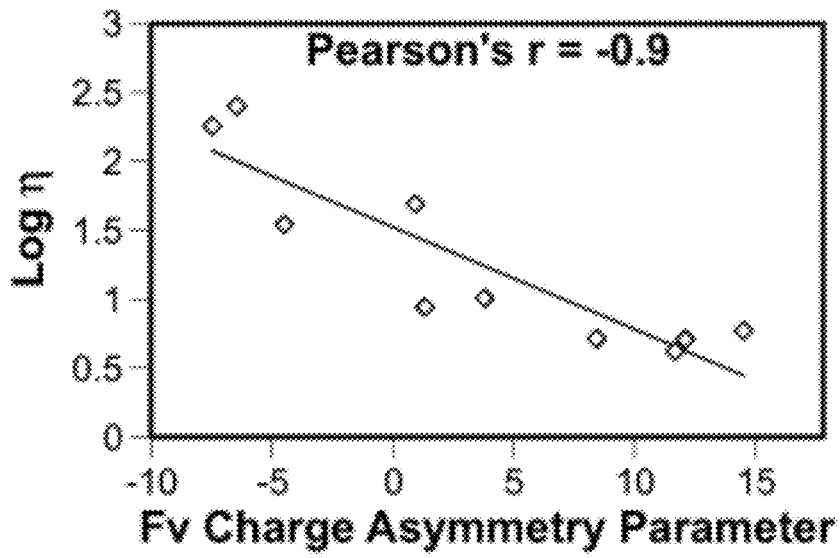
Figure 10A:
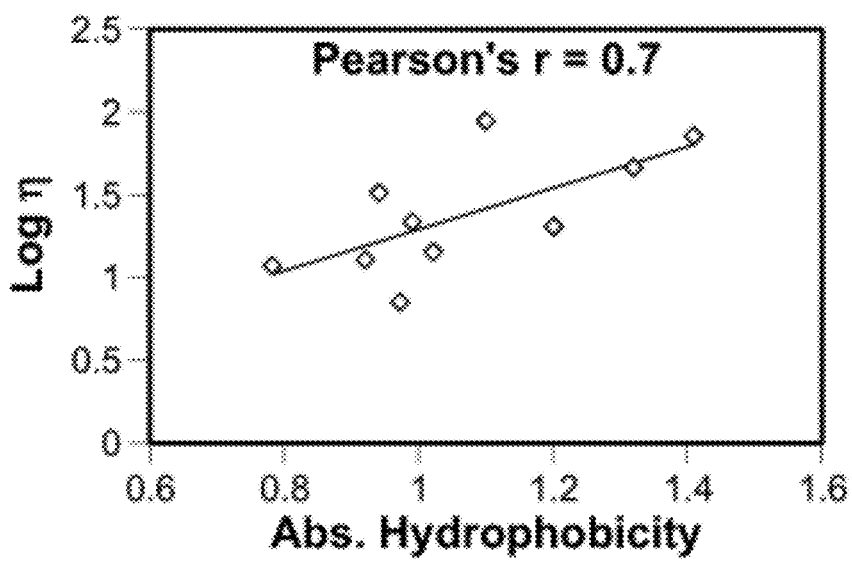
FIGS. 10A-10C show plots of correlation of log viscosity with calculated sequence-based structural parameters.
Figure 10B:
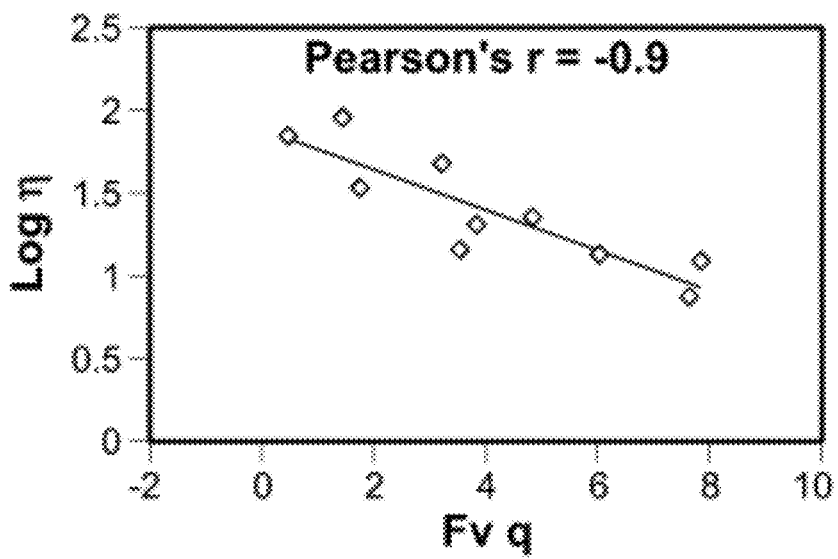
Figure 10C:
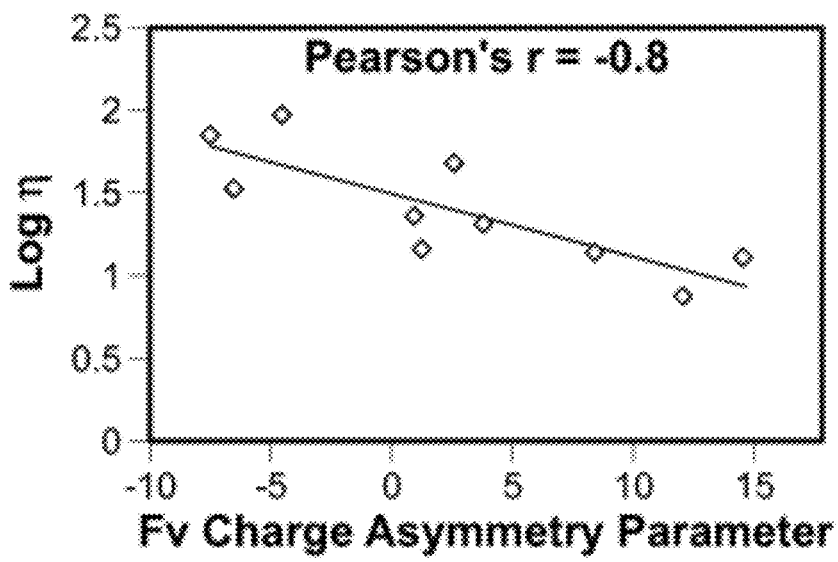

Next, correlations between these parameters and experimental viscosity values under two different solution conditions using a training set of 10 mAbs were examined. The two different solution conditions were a low ionic strength 20 mM buffered solution (histidine acetate) at pH 5.5 (FIGS. 9A-9C) and a high ionic strength 20 mM buffered solution (+200 mM arginine HCl) at pH 5.5 (FIGS. 10A-10C). For the low ionic strength buffer, a fair correlation was observed between the Fv charge and viscosity (Pearson's r=−0.8) and between FvCAP and viscosity (Pearson's r=−0.9). However, only a weak correlation was observed between HI and viscosity. Thus, electrostatic interactions appeared to play a dominant role in modulating viscosity with hydrophobicity contributing to a less extent to the overall viscosity of these mAbs. A stronger correlation between the FvCAP and viscosity pointed to the fact that the charge asymmetry between the VH and VL domain potentially played a role in modulating viscosity as well. For the high ionic strength buffer (FIGS. 10A-10C), correlations existed between Fv charge and viscosity (Pearson's r=−0.9) and between FvCAP and viscosity (Pearson's r=−0.8). A weaker correlation was observed between HI and viscosity, which suggested that under these conditions, all of the parameters contributed to modulating viscosity.

Figure 11A:
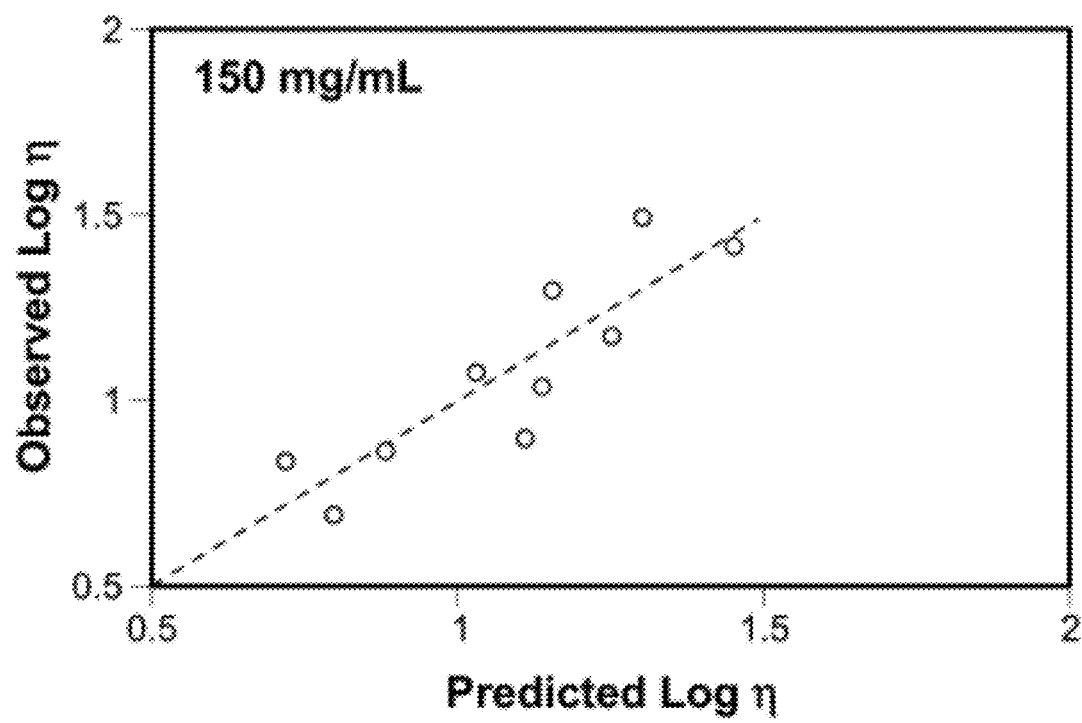
Figure 11B:
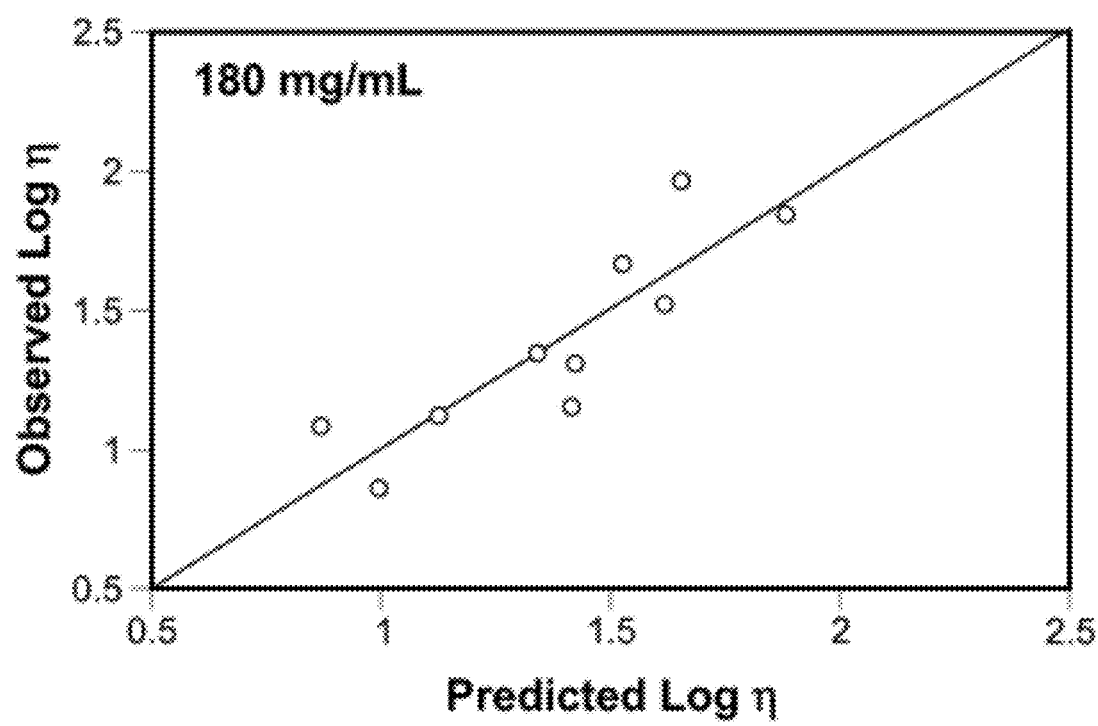
Figure 12A:
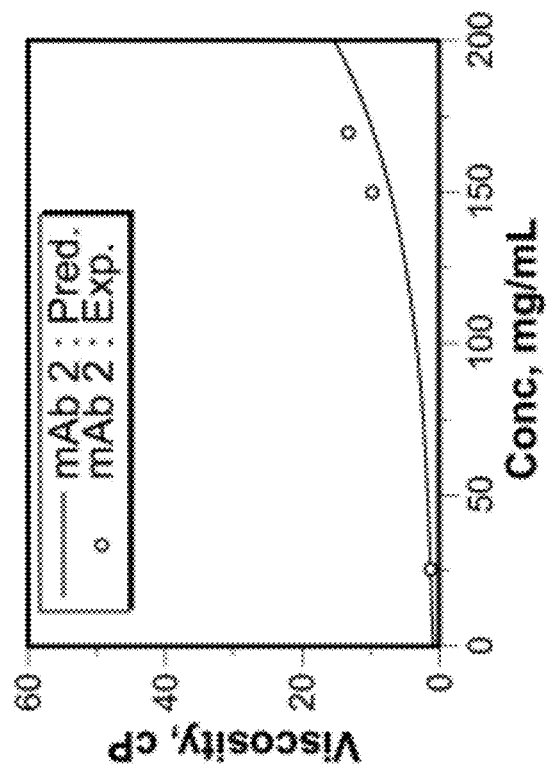
FIGS. 12A-12D show predicted viscosity-concentration profiles of four mAbs (A-D) as compared to their respective experimental data. The data points represent experimentally determined viscosity value in buffered solutions of high ionic strength (20 mM buffered solution at pH 5.5 with 200 mM Arginine HCl). The lines represent an optimized fit to predicted values. The predicted values were obtained using the Equations as described in the Examples section for mAb concentrations of 150 mg/mL and 180 mg/mL. The lines were generated using an equation of the form $y=a+be^{cx}$, where y is viscosity and x is protein concentration. This equation form was used to fit the experimental data up to 200 mg/mL for several mAbs (data not shown) and viscosity values as high as 200 cP. The fit was generated using predicted values at 150 mg/mL, 180 mg/mL and a viscosity value of 1.2 for 25 mg/mL protein concentration.
Figure 12B:
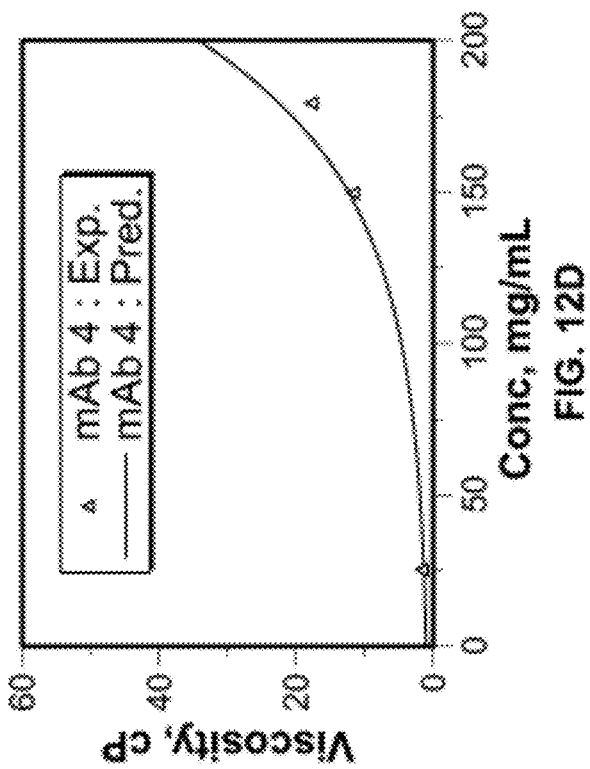
Figure 12C:
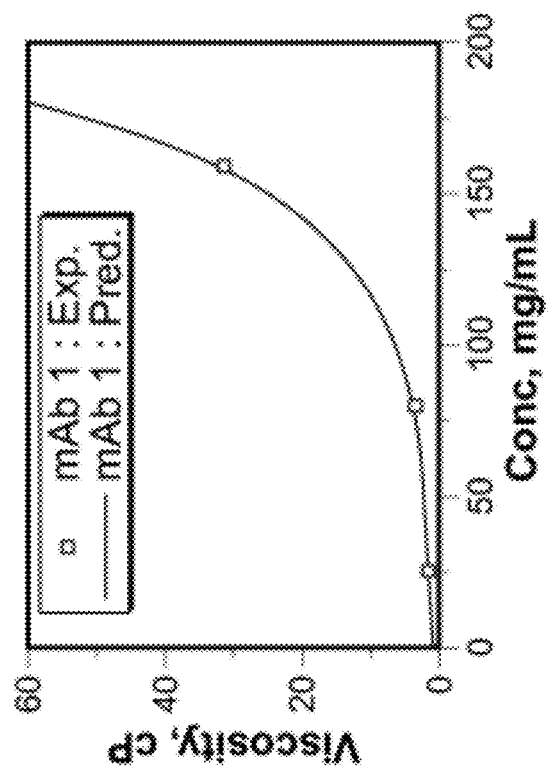
Figure 12D:
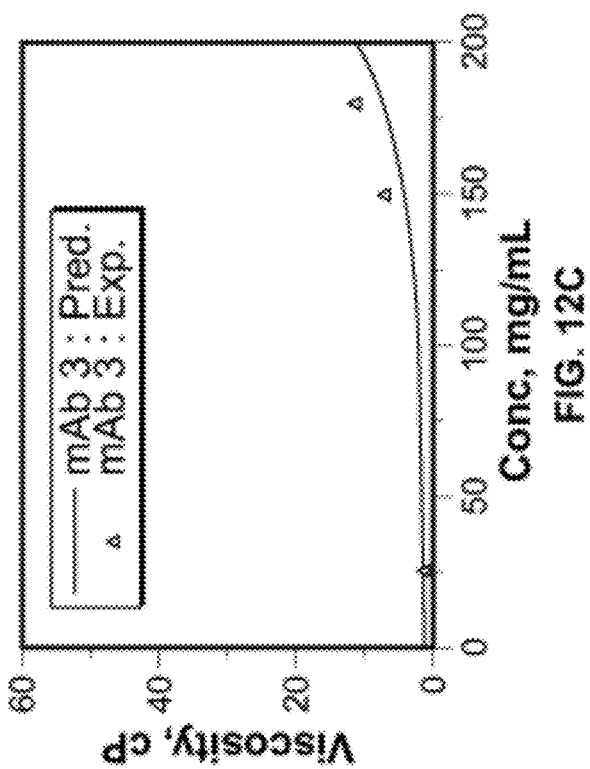

Next, PCR analysis was used as a multivariate (multiple variable) regression tool to assess its utility to be able to develop a predictive model for viscosity. Viscosity data under conditions of high ionic strength buffer was used as an example case along with the theoretically obtained parameters (FIG. 1A). Viscosity data at 150 mg/mL and 180 mg/mL at 25° C. were used as independent variables, whereas Fv charge at pH 5.5 (can also be represented as q), Fv CAP at pH 5.5 (can also be represented as $q_{CAP}$) and HI (can also be represented as $\phi$) were used as dependent variables. FIG. 1B shows viscosity data and calculated parameters, which do not include HI, for conditions of low ionic strength at 150 mg/mL at 25° C. for a training set of 10 mAb (partially overlapping the high ionic strength training set of 10 mAb). FIGS. 11A and 11B show the outcome of PCR analysis using the ~~above-mentioned~~ high ionic strength training set for 150 mg/mL and 180 mg/mL, respectively, where the observed experimental viscosity values are plotted against the predicted viscosity values as obtained through the best fit equation within the 90% confidence interval. The best fit equation is described below $$\eta(180 \text{ mg/mL}, 25°\text{ C.}) = 10^{\wedge}(1.19 + 0.42\phi - 0.05{*}q - 0.017{*}q_{CAP}) \qquad \text{Eq. 1}$$

$$\eta(150 \text{ mg/mL}, 25°\text{ C.}) = 10^{\wedge}(0.90 + 0.34\phi - 0.036{*}q - 0.012{*}q_{CAP}) \qquad \text{Eq. 2}$$

In additional experiments, a training set of 14 mAbs was tested. Instead of calculating the HI of the CDRs, in these experiments, the HI of Fv was calculated. PCR analysis was used as the multiple variable regression tool to assess its utility to be able to develop a predictive model for viscosity. FIG. 11C shows the outcome of PCR analysis, in which the observed experimental viscosity values at 180 mg/mL for various mAbs are plotted against the predicted viscosity values as obtained through the best fit equation within the 90% confidence interval. The best fit equation is described below:

$$\eta(180 \text{ mg/mL}, 25°\text{ C.}) = 10^{\wedge}(0.15 + 1.26\phi - 0.043{*}q - 0.020{*}q_{CAP}) \qquad \text{Eq. 1-1}$$

$$\eta(150 \text{ mg/mL}, 25°\text{ C.}) = 10^{\wedge}(0.06 + 1.13\phi - 0.034{*}q - 0.014{*}q_{CAP}) \qquad \text{Eq. 2-1}$$

It is noted that the coefficients may be specific to this buffer system and the respective protein concentration. Overall, a strong correlation (Pearson's r=0.9) and a mean absolute error of 7±9 at 180 mg/mL between observed and predicted values demonstrates that the model works well in obtaining the viscosity values using the calculated theoretical parameters from antibody sequence. To further test the validity of the model, a leave-one-out cross-validation (LOOCV) approach was used, in which the viscosity value for each of the mAb was used as the validation data point, while viscosity values for the rest of the mAbs were used as the training set. PCR analysis was performed on the training set and model output using the parameters was used to predict the viscosity of the "left-out" mAb; the steps were then repeated for each mAb. FIG. 11D shows a plot of observed experimental viscosity values at 180 mg/mL plotted against the LOOCV predictions. A strong correlation is observed (Pearson's r=0.8) with a mean absolute error of 9±10 between the predicted and the observed viscosity values.

Similarly, PCR analysis was used as the multiple variable regression tool to develop a predictive model for viscosity under conditions of low ionic strength buffer. A training set contained 10 mAbs at a concentration of 150 mg/mL in low ionic strength buffer (20 mM histidine buffer). FIG. 11E shows the outcome of PCR analysis using the 10 mAbs training set for 150 mg/mL, where the observed experimental viscosity values are plotted against the predicted viscosity values as obtained through the best fit equation within the 90% confidence interval. The best fit equation is described below $$\eta(150 \text{ mg/mL}, 25°\text{ C.}) = 10^{\wedge}(0.81 + 0.21{*}q - 0.15{*}q_{CAP}) \qquad \text{Eq. 3}$$

It is noted that the coefficients were specific to this buffer system and the respective protein concentrations. Overall, a strong correlation between observed and predicted values ($r^2$=0.8), demonstrated that the model worked well in obtaining the viscosity values using the calculated theoretical parameters from antibody sequence. To test the validity of the model, the model was implemented on four different antibodies outside the training set. Using the theoretical parameters and Equations 1 and 2, the viscosities were calculated at 180 mg/mL and 150 mg/mL separately and, assuming the viscosity of 1.2 cP at 25 mg/mL and 0.8 at 0 mg/mL, a four-point theoretical viscosity-concentration curve was generated and compared to the experimental viscosity data. FIGS. 12A-12D show such comparison for four mAbs. The theoretical model predicted the viscosity-concentration well when compared with the experimental data. Thus, the model equation obtained through Partial Least Squares regression analysis, using the sequence-derived theoretical parameters, was effective in predicting the viscosity-concentration curves for this protein-buffer system involving the antibodies of the IgG1 isotype.

Clearance

Different antibodies of the same isotype may exhibit notable differences in plasma clearance in humans as well as in Cyno monkeys. (Plasma clearance in Cyno monkeys (Cyno clearance) is an established preclinical model to assess pharmacokinetic profile of mAbs (see, e.g., Hötzel, I. et al. A strategy for risk mitigation of antibodies with fast clearance. *mAbs* 4, 753-760).) A few studies have shown such differences to be correlated to pI or specific mutations in the sequence (see, e.g., Igawa, T. et al. Reduced elimination of IgG antibodies by engineering the variable region. *Protein Engineering Design and Selection* 23, 385-392; Wu, H. et al. Development of Motavizumab, an Ultra-potent Antibody for the Prevention of Respiratory Syncytial Virus Infection in the Upper and Lower Respiratory Tract. *Journal* of *Molecular Biology* 368, 652-665 (2007)). Based on the hypothesis that differences in any observable properties of mAbs should preferably be related to differences in the Fv or CDRs (within the same framework), it was explored to determine if any of the sequence properties would predict the differences in Cyno clearance. The underlying hypothesis was that faster clearance was due to off-target binding of the mAb to surfaces/or proteins in vivo through increased protein-protein interactions that were hydrophobic and/or electrostatic in nature. Therefore, it was surmised that any extremes of such properties in the variable domain such as pI, charge or hydrophobicity would translate into the antibody exhibiting a faster Cyno clearance. Based on published data, a clearance value of >/=10 mL/kg/day in Cyno monkeys was designated as faster clearance and value of <10 mL/kg/day was designated as normal clearance (see, e.g., Hötzel, I. et al. A strategy for risk mitigation of antibodies with fast clearance. *mAbs* 4, 753-760).

Figure 13A:
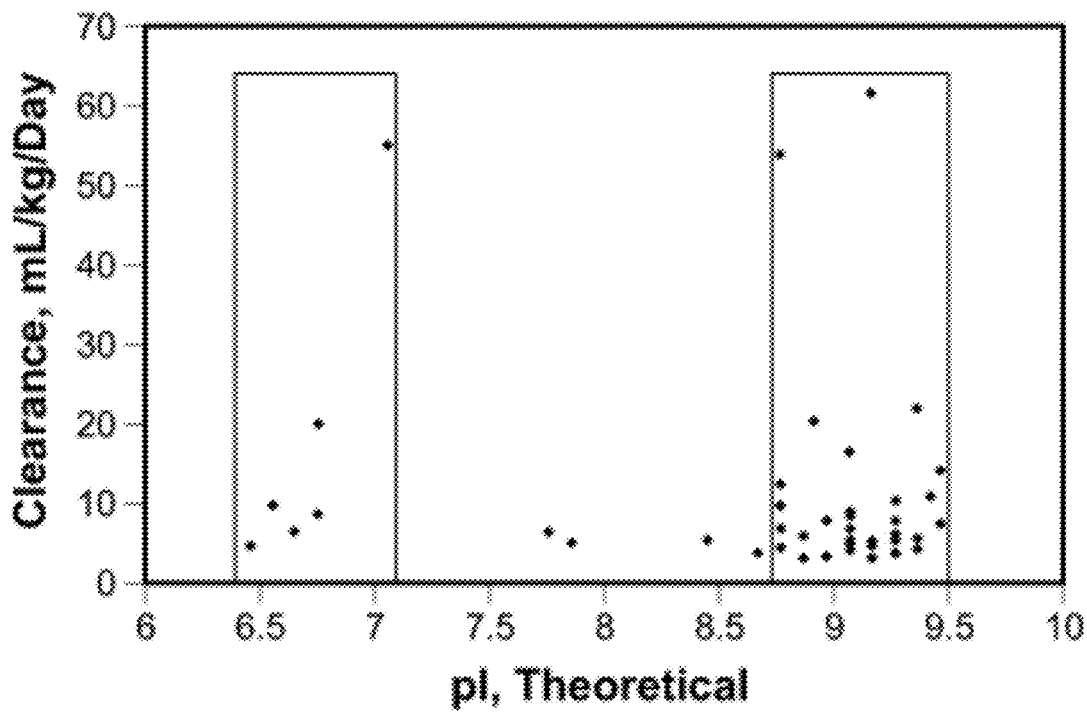
FIGS. 13A and 13B show a relationship between antibody clearance in Cyno monkeys and calculated antibody parameters.
Figure 13B:
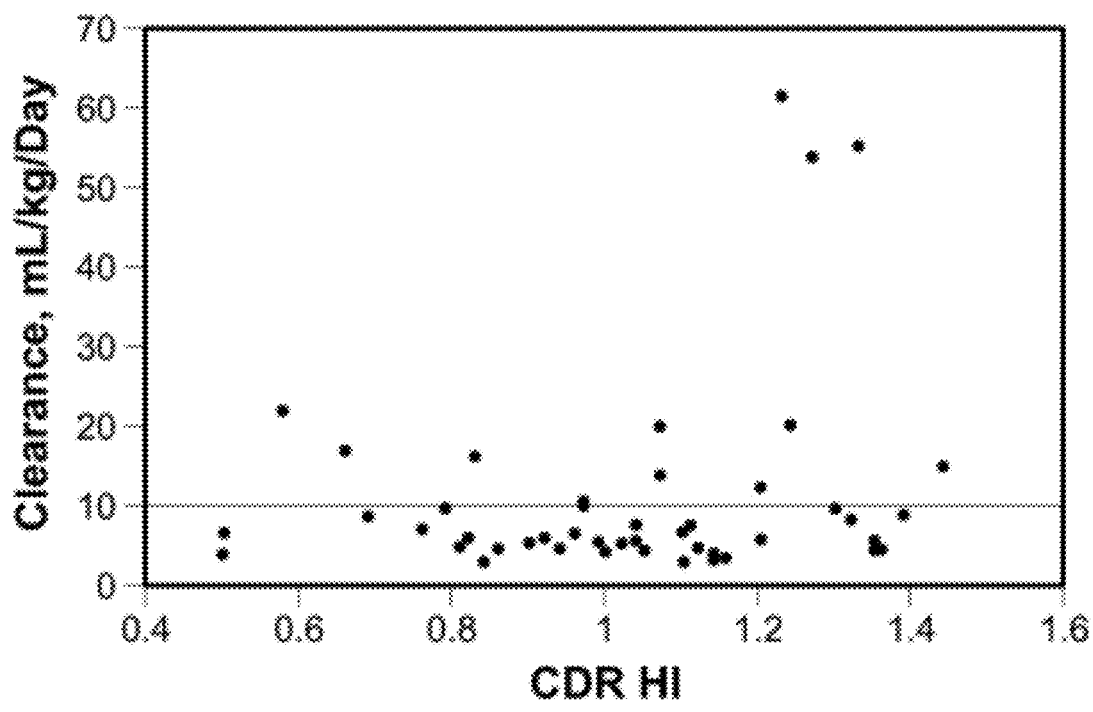
Figure 15A:
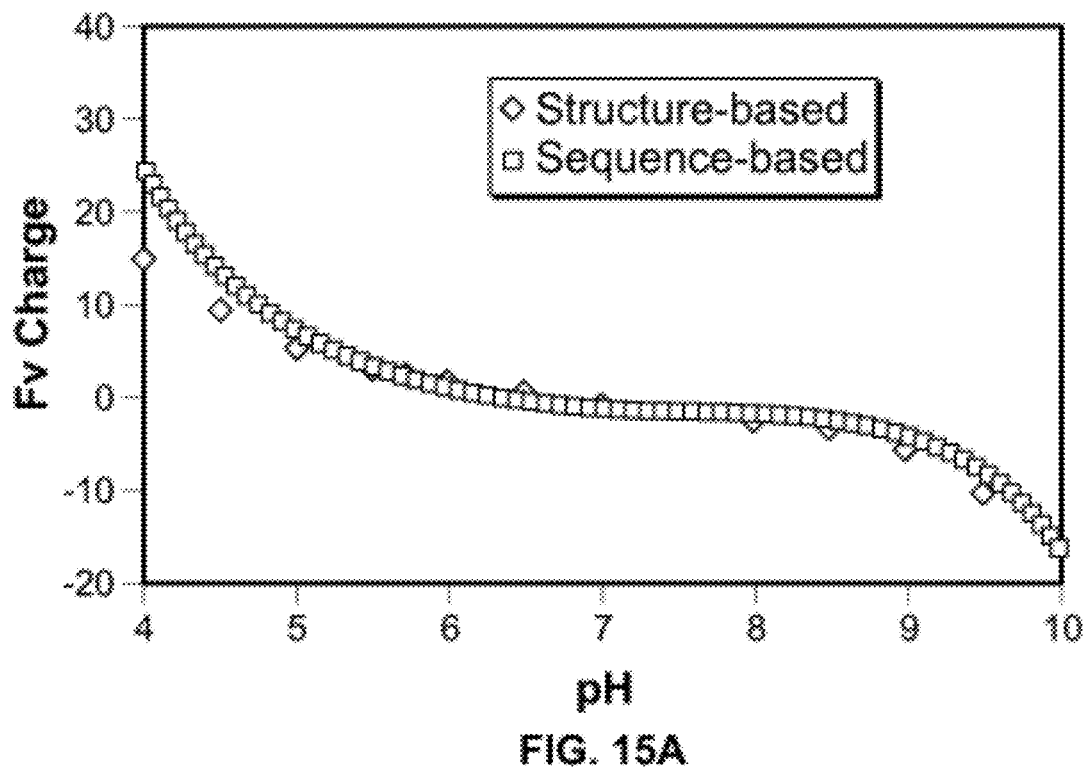
FIGS. 15A-15C show comparisons of the sequence-based and structure-based charge-pH profiles of antigen-binding fragment (Fab) domains of three different mAbs of the Fab pI of (A) 6.5, as shown in FIG. 15A; (B) 7.5, as shown in FIG. 15B; and (C) 9.2, as shown in FIG. 15C. The sequence-based charge-pH profiles were calculated as described in the Exemplary Methods section, below. The structure-based charge-pH profiles were calculated using an empirical method, PROPKA, and Fab structures. Individual association constants (in logarithmic form, pKa) of each charged amino acid side chain were obtained and used in the Henderson-Hasselbalch equation to obtain the side chain's charge at a given pH. The charges were then summed to obtain the net charge at a given pH.
Figure 15B:
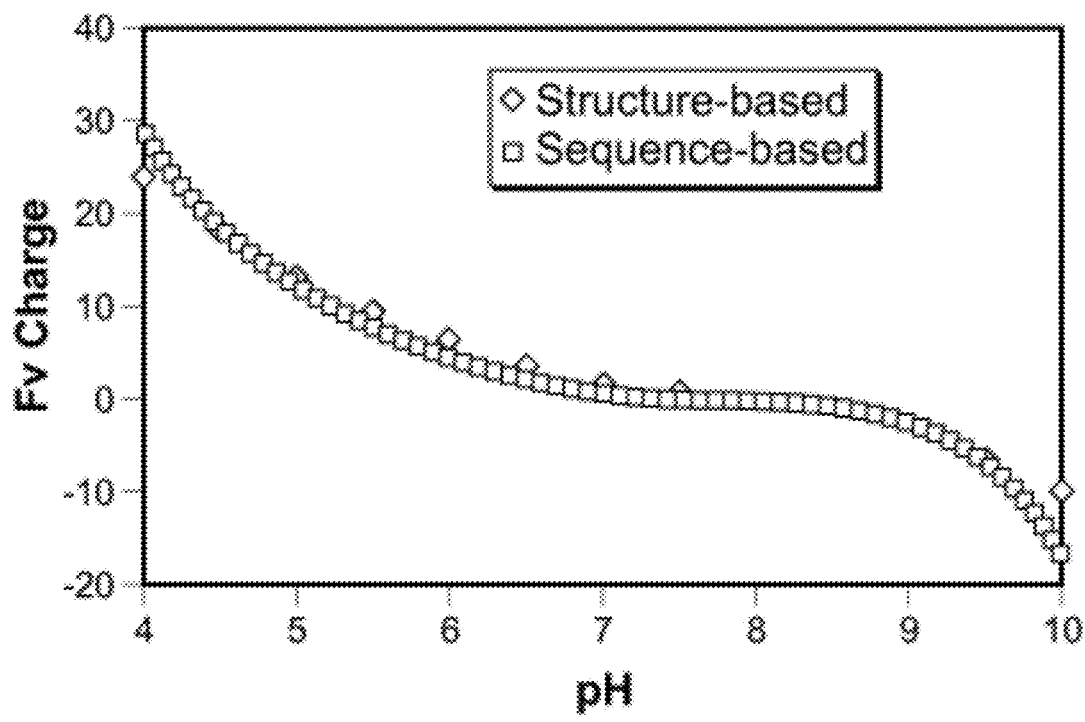
Figure 15C:
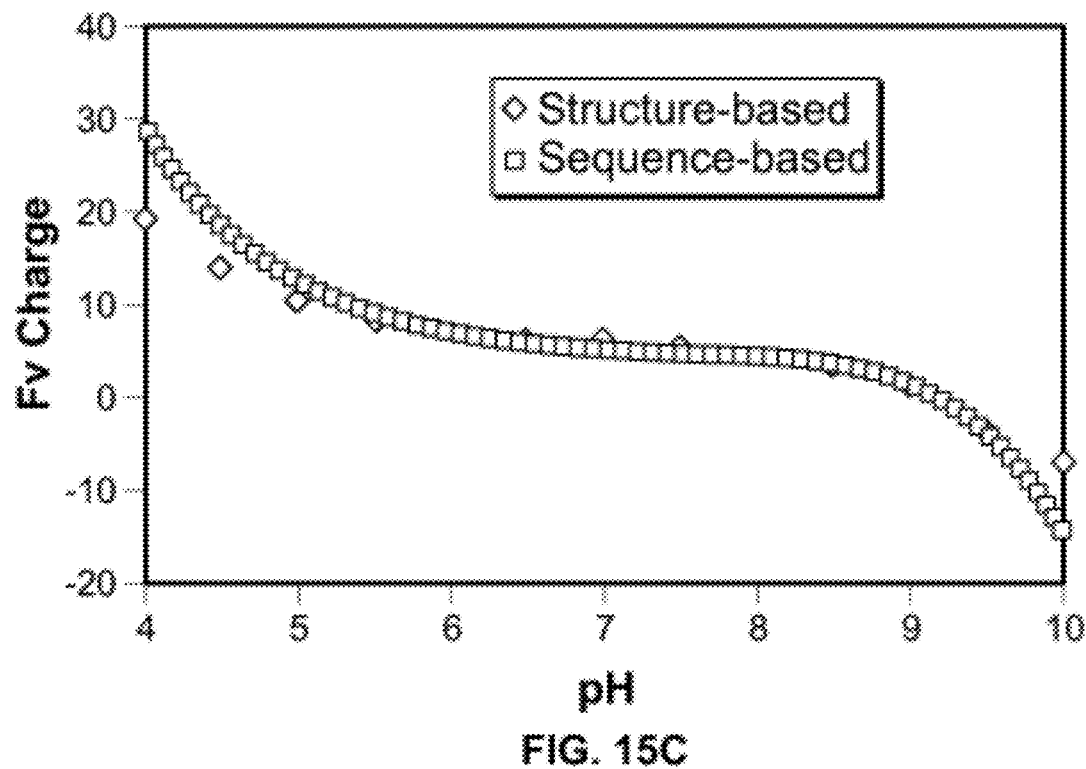
Figure 15D:
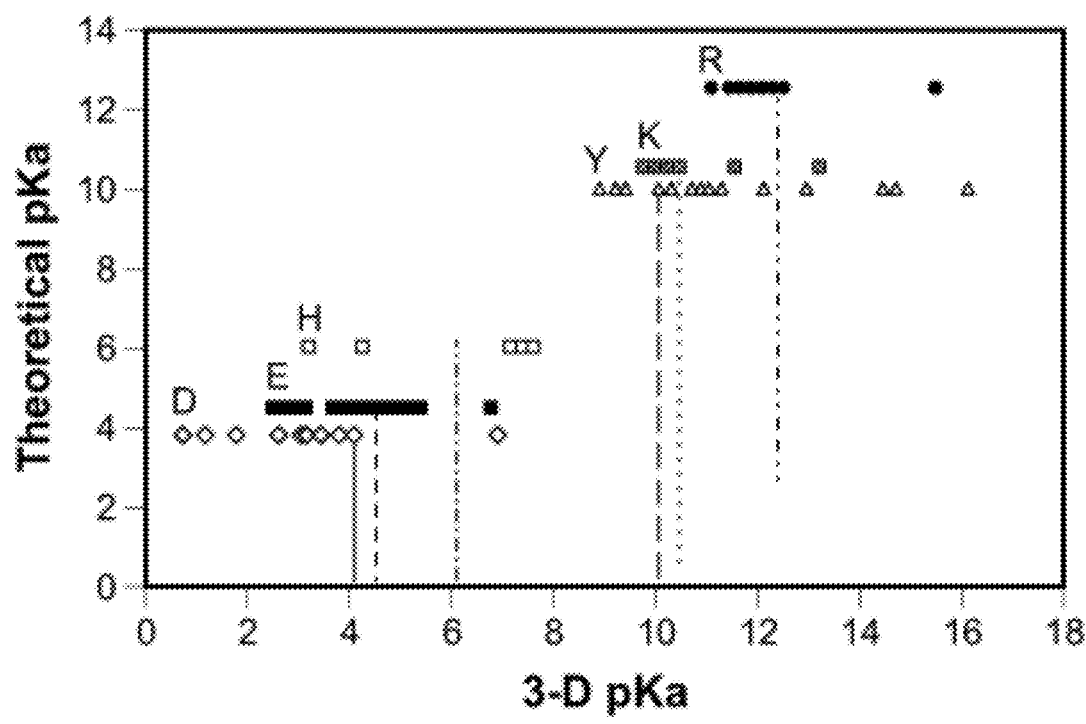

A large set of IgG1 class of mAbs (45 mAbs) was evaluated and compared to the Cyno clearance at the maximum administered dose (ranging from 10 mg/kg to 100 mg/kg) with the calculated pI of the mAb and the HI values of the CDR sequence (FIGS. 13A and 13B). As reported in the literature (see, e.g., Hötzel, I. et al. A strategy for risk mitigation of antibodies with fast clearance. *mAbs* 4, 753-760), no clear correlation was observed between the calculated mAb pI and clearance or between HI (calculated from CDR or Fv) and clearance (data not shown). While no clear correlation was observed between pI and clearance or HI and clearance, it was noticed that at the high pI values (~8.7-9.5) and low pI values (~6.4-7.1), as well as at high HI values (>1.2), more mAbs have high clearance values. A correlation between the calculated charge of the Fv domain at pH 7.4 (physiological pH) and the clearance values (data not shown) was not seen.

Next, it was examined to determine if pI (and/or charge) and hydrophobicity were complementary to each other in defining faster versus normal clearance. Also explored was whether charge at a certain pH would be more discriminating with respect to clearance values (antibody clearance involves neonatal Fc receptor salvation through the endosomal environment that has low pH, pH 5-6 (where Fc is a C-terminal region of an antibody heavy chain that contains at least a portion of the constant region)) (see, e.g., Wang, W., Wang, E. Q. & Balthasar, J. P. Monoclonal Antibody Pharmacokinetics and Pharmacodynamics. *Clin Pharmacol Ther* 84, 548-558 (2008)). Therefore, it was explored whether the correlation of Fv charge to clearance across the pH range of 5.0-7.4 existed. Also examined was whether hydrophobicity of certain CDRs would correlate better with clearance rather than the overall CDR sequence hydrophobicity. With these multitude of variables it was determined that a certain combination of these variables would be more discriminating towards clearance.

To simplify the analysis, a training set of 13 mAbs was generated to cover the full range of clearance values (FIG. 2). The mAbs in the training set were arranged in decreasing order of clearance values. Criteria were evaluated that allowed for separation of the two groups of mAbs, i.e., a group of mAbs with a clearance value of >/=10 mL/kg/day and a group of mAbs with a clearance value of <10 mL/kg/day. As mentioned, the overall hydrophobicity of all of the CDRS was not sufficient for the differentiation. Furthermore, the hydrophobicity of LC CDR2, HC CDR1 and HC CDR2 also did not provide such differentiation as shown by the average HI value calculated for faster clearing mAbs against normal clearing mAbs. On the other hand, a general trend was noticed that faster clearing mAbs tended to have higher hydrophobicity among the remaining 3 CDRs (LC CDR1, LC CDR3, and HC CDR3). The average HI value for the fast clearing mAbs, was in general, higher compared to that for the normal clearing mAbs. This became further evident using a calculated sum of the HI values of these 3 CDRs. The average HI sum (LC CDR1, LC CDR3, and HC CDR3) for the mAbs in the faster clearing group was significantly higher than those in the normal clearing mAbs (3.9+/−1.4 versus 2.5+/−0.7, respectively, p=0.005). With respect to charge, it was noticed that at pH 5.5, mAbs with normal clearance values tended to have charge values between 0.4-6.1, while 4 out of 7 mAbs that clear faster had charge values outside this range. Furthermore, it appeared that the charge and selective HI of CDRs were complementary to each other in differentiating faster clearing mAbs, i.e. those mAbs with charge values between 0.4 and 6.1 in the fast clearance group had a relatively higher HI sum. This data analysis indicated that both extremes of hydrophobicity of certain CDRs as well as extremes of charge values (either negative or highly positive) could be used to predict mAbs with faster clearance.

The above analysis led to developing a criterion to differentiate faster clearing mAbs from those with normal clearance (FIG. 3). If mAbs with the HI sum value of >4.0 and/or an Fv charge value of either </=−2.0 or >/=6.2 (FIG. 2, leftward back-slash hatched background) were segregated from those with the hydrophobicity sum value of </=4.0 and Fv charge values within −2.0 to 6.2 (FIG. 2, rightward forward-slash hatched background), faster clearing mAbs become clearly noticeable compared to the normal clearing mAbs.

Theoretical criteria were extended to the complete set of 45 mAbs to test its validity. In order to facilitate visualization of such analysis the background hatching coding scheme described above was used. All values of HI sum >4.0 were assigned a leftward back-slash hatched background and the rest were assigned a rightward forward-slash hatched background. All charge values of </=−2.0 or >/=6.2 were assigned the leftward back-slash hatched background and the rest were assigned the rightward forward-slash hatched background. All Cyno clearance values of >/=10 were assigned the leftward back-slash hatched background and the remaining were assigned the rightward forward-slash hatched background. Next, the data were sorted based on increasing measured clearance values to determine if the hatching patterns matched up (and therefore if the criteria would predict the right outcome) (FIG. 4). Indeed, the criteria held up well for the complete set of 45 mAbs. Based on either high HI sum or Fv charge extremes, faster Cyno clearance for 15/16 (94%) mAbs (including 6/6 in the original training set) and normal Cyno clearance for 24/29 (83%) mAbs (including 7/7 in the original training set) were correctly predicted.

In additional experiments, the training set was expanded to 14 mAbs to develop criteria to differentiate faster clearing mAbs from those with normal clearance. In this training set, faster clearing mAbs were clearly separated from the normal clearing mAbs when the criteria were set such that mAbs with the HI sum value of >4.0 and/or an Fv charge value of either 0 or 6.2 would be at risk of exhibiting faster clearance, whereas those with the HI sum value of 4.0 and Fv charge values with 0 to 6.2 would exhibit normal clearance. The criteria were extended to a set of 61 mAbs to test its validity. Based on either high HI sum or Fv charge extremes, correct prediction was achieved of faster Cyno clearance for 10/13 (77%) mAbs (excluding 8/8 in the original training set, 86% including the training set mAbs) and of normal Cyno clearance for 24/34 (70%) mAbs (excluding 6/6 in the original training set, 75% including the training set mAbs) (data not shown).

These analyses established the ability of utilizing fundamental molecular properties such as charge and hydrophobicity in assessing the biological properties such as clearance in this case. The analysis supported the hypothesis that non-specific binding was responsible for faster clearance from plasma, as the variable domain with extreme of hydrophobicity or charges could potentially interact with surfaces other than the targeted antigen.

Trp Oxidation and Asp Isomerization

Chemical modifications such as Trp oxidation and Asp isomerization and associated loss in potency may limit the shelf-life of mAb products in aqueous solutions. All-atom MD simulations were employed with explicit water to enable risk-ranking the relative liability of Trp oxidation and Asp isomerization.

For Trp oxidation, correlation was examined between MD generated time-averaged SASA and the extent of oxidation of Trp residues in the presence of 2,2'-Azobis(2-amidinopropane) dihydrochloride (AAPH, a chemical known to oxidize labile amino acid side chains) (see, e.g., Ji, J. A., Zhang, B., Cheng, W. & Wang, Y. J. Methionine, tryptophan, and histidine oxidation in a model protein, PTH: Mechanisms and stabilization. *Journal of Pharmaceutical Sciences* 98, 4485-4500 (2009)). AAPH generated organic free radicals leading to oxidation of exposed side chains. It was therefore hypothesized that SASA could provide a direct indication of the propensity of a Trp to oxidize in solution if an oxidizing species was introduced in the solution during manufacturing or storage. FIG. 5 lists 38 Trp residues in 17 different mAbs. All these Trps were present in the CDRs except for the last 9 Trps, which were present in the constant region.

A criterion was defined where Trps with >35% oxidation in the presence of AAPH were designated as oxidation labile Trps while, below this percentage, as non-labile Trps. Trp residues were background hatching coded with >35% oxidation assigned a leftward back-slash hatched background and those below were assigned a rightward forward-slash hatched background, and all the Trps were sorted on the basis of oxidation (FIG. 5). A pattern was readily recognizable, the average time-averaged SASA of labile Trp residues was significantly higher (122 $A^2$+/−40) compared to the non-labile (37 $A^2$+/−41), with a p-value of 0.0001. Based on this analysis, and to minimize the number of false negatives, a cutoff value of >80 $A^2$ side chain SASA (>30% SASA for Trp side chain) was assigned to correlate with labile Trp sites and to be able to distinguish between reactive and non-reactive sites. This criterion correctly identified 13/14 (93%) labile Trp residues and 20/24 (83%) non-labile Trp residues. It was noticed that for molecules where false positives were identified using the above-mentioned criterion, at least for two out of three mAbs i.e., mAb12 Trp HC109, mAb7 TRP HC33, these molecules tend to have two Trps on a single Fv domain that are nearly equally solvent exposed. The question arouse if experimentally, the statistical probability of oxidizing two exposed Trps on a single Fv is low compared to single Trp site on multiple Fv domains (and therefore mAbs), which would result in only one Trp being preferentially oxidized when exposed to an oxidant, even when the solvent exposure is similar. If it was true, this could have been one of the potential causes for obtaining the false positives identified based on solvent-accessibility. Overall, it was concluded that the time-averaged SASA of Trp side chain was sufficient to be able to differentiate between the labile and the non-labile Trp residues and when two Trps with sufficient solvent accessibility were present in the single Fv domain, such criteria should be used with caution.

For Asp isomerization, multiple variables related to potentially labile Asp residues were generated from MD trajectories. Consistent with the Asp isomerization mechanism (see, e.g., Wakankar, A. A. et al. Aspartate isomerization in the complementarity determining regions of two closely related monoclonal antibodies. *Biochemistry* 46, 1534-1544 (2007)) (nucleophilic attack of the Asp carbonyl by the N-terminal peptide bond nitrogen of the N+1 residue), the following properties were examined: (1) time average SASA for all Asp residues (SASA_Asp), the main chain N atom of the n+1 residue (SASA (n+1), N), and H atom of the n+1 residue (SASA (n+1), H) of Asp residues; (2) intra-residue mutual information (MI) for Asp residues; (3) Shannon entropy for $\phi$-$\psi$ distributions; and (4) Root-mean-square fluctuations for Cα atoms (RMSF). A number of Fabs, which contained both known labile as well as stable Asp residues, were chosen for MD calculations. Motifs which have previously demonstrated to isomerize on timescales that impact shelf-life were focused on (DG, DS, DT, DD, DA) (see, e.g., Radkiewicz, J. L., Zipse, H., Clarke, S. & Houk, K. N. Neighboring Side Chain Effects on Asparaginyl and Aspartyl Degradation: An Ab Initio Study of the Relationship between Peptide Conformation and Backbone NH Acidity. *J. Am. Chem. Soc.* 123, 3499-3506 (2001); Yi, L. et al. Isomerization of Asp-Asp motif in model peptides and a Monoclonal Antibody Fab Fragment. *Journal of Pharmaceutical Sciences* 102, 947-959) and excluded the remaining Asps.

An experimental data set was compiled in which all mAbs were formulated under similar conditions (pH 5.5), thermally stressed (40° C.) and subject to peptide map analysis to calculate the degradation rates for Asp residues. FIG. 6 shows both the experimental results as well as properties determined from the MD simulations. All potentially labile Asp residues are included in FIG. 6, with the exception of non-CDR Asp residues (framework residues) that were only listed for a single protein, as repeating these non-CDR Asp residues would be redundant.

Data analysis was two-fold. Firstly, labile residues (>1=2.5%/wk) were separated from stable residues (<2.5%/wk) and compared the average value of each of the properties among the two groups of Asp residues (FIG. 14). This step enabled identification of which properties showed substantial differences among the two groups. As shown by the p-values, among the six properties tested, four properties, namely the SASA_Asp, RMSF, SASA (n+1, N) and (n+1, H), showed significant differences (80% CI) among the two groups of Asp residues. Since none of these four properties on their own predicted Asp isomerization rates, a multivariate analysis was next used. A direct correlation could not be established using multivariate regression tools of principal component or partial least squares regression. The question was therefore asked if a binary correlation could be established, i.e., can sites with rates 2.5%/wk from ones with <2.5%/wk be differentiated. To this end, a value of 1 was assigned to rates of >2.5%/wk and a value of 0 to rates <2.5%/wk (FIG. 6). Logistic regression were then performed using SASA_Asp, RMSF, SASA (n+1, N) as independent variables and the binary rate output as the dependent variable. The parameter SASA (n+1, H) was excluded as it did not provide additional benefit in the regression analysis. The equation output as a result of this regression is shown below:

$$Y1=1/(1+\exp(+22.2+0.13*SASA\_ASP+3.3*RMSF+16.0*SASA(n+1,N)))) \quad \text{Eq. 4}$$

The output of this equation was rounded off to one significant figure to deliver a result of either 0 (non-reactive) or 1 (reactive) and is shown in FIG. 6.

The logistic regression predicts 5/6 labile sites and all 9/9 non-reactive sites correctly. Essentially, the equation generated through logistic modeling enables one to use the three parameters, (SASA_Asp, RMSF and SASA (n+1, N)), to predict the susceptibility of an Asp residue to degrade at a rate greater than 2.5%/wk under the experimental conditions tested.

The validity of the model was tested using the LOOCV approach. Leaving one mAb out and using the remaining mAbs as a training set for the logistic regression analysis, 5/6 labile sites and 7/9 non-reactive sites were predicted (FIG. 6). While the correct prediction outcome was reduced a little, it still correctly predicted a total of 12/15 sites (80%) and therefore was satisfactory. The lowering of percent of correctly predicted sites using the LOOCV approach points to the likelihood that particular mAbs of the original training set may contribute disproportionally to maintaining a high correct prediction outcome. It is noted that, while this modeling approach may be specific to a specific set of experimental conditions, the underlying approach can likely be extended to any set of experimental conditions as long as the experimental rates are known for a set of Asp residues.

FIG. 18 shows illustrative apparatus 1800. Apparatus 1800 may be a computing machine. Apparatus 1800 may include chip module 1802, which may include one or more integrated circuits, and which may include logic configured to, based on calculated physiochemical characteristics of the antibody, for example, determine the suitability of the antibody for production or inclusion in a therapeutic agent; select an antibody among candidate-antibodies for inclusion in the therapeutic agent; support manufacture of the therapeutic agent comprising the antibody; or to perform any other suitable logical operations associated with in-silico antibody selection or with other related activities.

Apparatus 1800 may include one or more of the following components: I/O circuitry 1804, which may include the transmitter device and the receiver device and may interface with fiber optic cable, coaxial cable, telephone lines, wireless devices, PHY layer hardware, a keypad/display control device or any other suitable media or devices; peripheral devices 1806, which may include counter timers, real-time timers, power-on reset generators or any other suitable peripheral devices; logical processing device 1808, which may compute, from antibody structural information, structural parameters of the antibody; select scaling factors corresponding to structural parameters of the antibody; quantify indicies corresponding to physiochemical characteristics of the antibody; quantify flow resistances of manufacturing and dispensing vessels; and machine-readable memory 1810.

Machine-readable memory 1810 may be configured to store in machine-readable data-structures: antibody structural information; scaling factors corresponding to structural parameters of the antibody; and any other suitable information or data.

Components 1802, 1804, 1806, 1808 and 1810 may be coupled together by a system bus or other interconnections 1812 and may be present on one or more circuit boards such as 1820. In some embodiments, the components may be integrated into a single silicon-based chip.

It will be appreciated that software components including programs and data may, if desired, be implemented in ROM (read only memory) form, including CD-ROMs, EPROMs and EEPROMs, or may be stored in any other suitable computer-readable medium such as but not limited to discs of various kinds, cards of various kinds and RAMs. Components described herein as software may, alternatively and/or additionally, be implemented wholly or partly in hardware, if desired, using conventional techniques.

Various signals representing information described herein may be transferred between a source and a destination in the form of electromagnetic waves traveling through signal-conducting media such as metal wires, optical fibers, and/or wireless transmission media (e.g., air and/or space).

Apparatus 1800 may operate in a networked environment supporting connections to one or more remote computers via a local area network (LAN), a wide area network (WAN), or other suitable networks. When used in a LAN networking environment, apparatus 1800 may be connected to the LAN through a network interface or adapter in I/O circuitry 1804. When used in a WAN networking environment, apparatus 1800 may include a modem or other means for establishing communications over the WAN. It will be appreciated that the network connections shown are illustrative and other means of establishing a communications link between the computers may be used. The existence of any of various well-known protocols such as TCP/IP, Ethernet, FTP, HTTP and the like is presumed, and the system may be operated in a client-server configuration to permit a user to operate logical processing device 1808, for example over the Internet.

Apparatus 1800 may be included in numerous general purpose or special purpose computing system environments or configurations. Examples of well-known computing systems, environments, and/or configurations that may be suitable for use with the invention include, but are not limited to, personal computers, server computers, hand-held or laptop devices, mobile phones and/or other personal digital assistants ("PDAs"), multiprocessor systems, microprocessor-based systems, tablets, programmable consumer electronics, network personal computers, minicomputers, mainframe computers, distributed computing environments that include any of the above systems or devices, and the like.

FIGS. 19A and 19B show illustrative processes 1900, for providing in-silico antibody selection in accordance with the principles of the invention. For the sake of illustration, the steps of the illustrated processes will be described as being performed by a "system." The "system" may include one or more of the features of the apparatus shown in FIG. 18 and/or any other suitable device, such as the computing machine, or approach. The "system" may be provided by the entity implementing in-silico antibody selection or by any other suitable individual, organization or modality.

In FIGS. 19A and 19B, solid arrows indicate flow of process control and flow of information. Dashed arrows indicate flow of information.

The order of performance and/or description of steps of the processes in FIGS. 19A and 19B is illustrative only. Each of the described steps need not be completed in the illustrated order or at all. Processes 1900 may include steps that are not shown.

Processes 1900 may be embodied as an algorithm. The algorithm may include some or all of the steps of processes 1900.

Processes 1900 may begin at step 1920 (shown in FIG. 19A). At step 1920, the system may receive a set of data. Information 1922 may include some or all of the data received at step 1920.

Information 1922 may include information pertaining to antibody (Ab) 1926 under solution conditions 1924. The system may perform processes 1900 to analyze Ab 1926 under conditions 1924 for satisfaction of design criterion (DC) 1958.

Ab 1926 may be of Ab sub/class 1948. Ab sub/class 1948 may be an antibody class such as IgA or IgE. Ab sub/class 1948 may be an antibody subclass such as IgA1. Ab sub/class 1948 may be an antibody subclass such as IgG1 or IgG4. Ab sub/class 1948 may be any antibody class, sub-class or variety.

Ab 1926 may have a structure. The structure of Ab 1926 may be represented by Ab structure 1950. Ab structure 1950 may be a digital code corresponding to the structure of Ab 1926.

Ab structure 1950 may include information about the amino acid sequence of antibody 1926. Sequence 1952 may represent the sequence information. Sequence 1952 may be a digital code corresponding to the sequence of Ab 1926. Sequence 1952 may represent primary structure.

Sequence 1952 may include complete sequence 1954 of Ab 1926. Complete sequence 1954 may contain sequence information of all sections, domains, regions and/or features of Ab 1926, including heavy chain HC, light chain LC, variable domain Fv, constant domain Fc, any or all of the complementarity determining regions CDR1, CDR2, etc., and any other structural feature of Ab 1926.

Sequence 1952 may include sectional sequence 1956 of Ab 1926. Sectional sequence 1956 may be less complete than complete sequence 1954. Sectional sequence 1956 may be a partial sequence of Ab 1926. Sectional sequence 1956 may contain sequence information of one or more sections, domains, regions and/or features of Ab 1926, including heavy chain HC, light chain LC, variable domain Fv, constant domain Fc, any or all of the complementarity determining regions CDR1, CDR2, etc., and/or any other structural feature of Ab 1926.

Information 1922 may include information pertaining to conditions 1924. Conditions 1924 may include information pertaining to buffer+salt solution (BSS) 1930. BSS 1930 may be a digital code corresponding to some of the conditions of the solution containing Ab 1926. Conditions of the solution may include one or more of: temperature (T) 1932; chemical composition 1934 of the buffer+salt solution, which may include identification of the chemical species of the buffer+salt solution, which may or may not contain salt other than that in the buffer; and concentrations 1936 of chemical species that may be present in the solution. Concentrations 1936 may include information pertaining to one or more of: buffer concentration 1938; salt concentration 1940; Ab concentration 1942; pH 1944; and ionic strength 1946 (IS).

BSS 1930 may represent a virtual solution. The virtual solution may be associated with MD simulations. BSS 1930 may represent a real-world solution. Ab 1926 may represent a virtual antibody. The virtual antibody may be associated with MD simulations. The virtual antibody may be based on a real-world antibody, differing from the real-world-antibody by a hypothetical variation of sequence. Ab 1926 may represent a real-world antibody.

Information 1922 may include information pertaining to physiochemical characteristic (PC) 1928. PC 1928 may include one or more physiochemical characteristics such as viscosity, clearance, stability, aspartic acid lability and tryptophan lability. PC 128 may include any other physiochemical characteristic of an Ab solution or an Ab, such as color or isoelectric point. PC 128 may play a role in determining DC 1958. For example, if PC 128 is viscosity, DC 1958 may be related to viscosity; DC 1958 may include, for example, a viscosity limit.

Information 1922 may include BSS output 1931. BSS output 1931 may include data pertaining to conditions 1924. BSS output 1931 may include data pertaining to BSS 1930.

Information 1922 may include Ab output 1927. Ab output 1927 may include data pertaining to Ab 1926.

Information 1922 may include PC output 1929. PC output 1929 may include data pertaining to PC 1928.

Information 1922 may include DC output 1959. DC output 1959 may include data pertaining to DC 1958.

The system may proceed from step 1920 to step 1960. At step 1960, the system may select an objective function. The objective function may include scaling factors (sf) and parameters (P). Parameters P may include one or more structure-related properties such as charge, charge asymmetry, and hydrophobicity. Parameters P may include any other structure-related property, such as magnetic moment and dipole moment. The system may multiply a parameter $P_i$ by a scaling factor $sf_i$. The multiplicative product $sf_iP_i$ may be a term in the objective function.

The system may select the objective function on the basis of information from PC output 1929. The information from PC output 1929 may include information relating to PC 1928. The information relating to PC 1928 may be used in selecting the objective function. For example, if PC 128 is viscosity, the system may select an objective function that, upon being evaluated for Ab 1926 under conditions 1924, may yield an index corresponding to the viscosity of Ab 1926 in BSS 1930. The mathematical form of the objective function may relate $sf_iP_i$ terms to PC 1928.

The system may proceed to step 1962. At step 1962, the system may select parameters to be included in the objective function. The parameters may include parameters $P_1 \ldots P_n$, where n may be the total number of parameters included in the objective function. The system may select parameters $P_1 \ldots P_n$ on the basis of information from Ab output 1927. The information from Ab output 1927 may include information relating to Ab 1926. The information relating to Ab 1926 may be used in selecting parameters $P_1 \ldots P_n$. For example, if the objective function selected at step 1962 relates $sf_iP_i$ terms to viscosity, the selection of parameters $P_1 \ldots P_n$ may depend on Ab sub/class 1948. If Ab sub/class 1948 is IgG4, the system may include in the objective function parameters relating to properties of Fc; if Ab sub/class 1948 is IgG1, the system may exclude from the objective function parameters relating to properties of Fc.

The system may select parameters $P_1 \ldots P_n$ on the basis of information from BSS output 1931. The information from BSS output 1931 may include information relating to BSS 1930. The information relating to BSS 1930 may be used in selecting parameters $P_1 \ldots P_n$. The information from BSS output 1931 may include information relating to ionic strength (IS) 1946. The information relating to IS 1946 may be used in selecting parameters $P_1 \ldots P_n$. For example, if the objective function selected at step 1960 relates $sf_iP_i$ terms to viscosity, the selection of parameters $P_1 \ldots P_n$ may depend on IS 1946. If IS 1946 is a high ionic strength, the system may include in the objective function parameters relating to hydrophobicity; if IS 1946 is a low ionic strength, the system may exclude from the objective function parameters relating to hydrophobicity.

The system may proceed to step 1964. At step 1964, the system may select sf values. Selection of sf values may include, at step 1966, identifying sf values $sf_1 \ldots sf_n$. Each value, $sf_1 \ldots sf_n$, may serve as a multiplier of one of parameters $P_1 \ldots P_n$, respectively. At step 1966, identifying values $sf_1 \ldots sf_n$ may include identifying each scaling factor value in machine memory 1910 (shown in FIG. 19B).

Machine memory 1910 may include one or more of the features of memory 1810 (shown in FIG. 18). Machine memory 1910 may store the scaling factor values. Machine memory 1910 may store scaling factor values by temperature, as represented by memory configured by temperature ($T_A$ to $T_x$) 1911. Machine memory 1910 may store scaling factor values by ionic strength, as represented by memory configured by ionic strength ($IS_\alpha$ to $IS_\omega$) 1913. Machine memory 1910 may store scaling factor values by sub/class, as represented by memory configured by IgG subclasses ($IgG_1$ to $IgG_4$) 1915. Machine memory 1910 may store scaling factor values by buffer+salt solution composition, as represented by memory configured by buffer+salt solution ($BSS_1$ to $BSS_m$) 1916. Machine memory 1910 may store scaling factor values by pH, as represented by memory configured by pH ($pH_I$ to $pH_X$) 1917.

Machine memory 1910 may store data such as those shown in machine memory configuration 1919. Configuration 1919 may represent a view of machine memory 1910 provided by a data-viewing tool such as a display controlled by I/O circuitry 1804 (shown in FIG. 18). Configuration 1919 includes a variety of scaling factors values, based on particular Ab structural features (e.g., complete sequence, Fv, Fc), for an IgG1 under specific conditions (180 mg/mL Ab at 25° C., pH 5.5 and high IS; in 20 mM buffer+200 mM arginine HCl, each value approximate).

Database 1905 may store measured PC values of antibodies of various sub/classes under various conditions. The system may analyze the measured PC values to derive the scaling factors. The system may store the scaling factor values in machine memory 1910.

At step 1964, the system may select values $sf_1 \ldots sf_n$ on the basis of information from BSS output 1931. The information from BSS output 1931 may include T 1932, composition 1934 and concentrations 1936. T 1932, composition 1934 and/or concentrations 1936 may be used in selecting values $sf_1 \ldots sf_n$. For example, for a set of parameters $P_1 \ldots P_n$ selected at step 1962 for an objective function selected at step 1960, values $sf_1 \ldots sf_n$ may depend on T 1932; while one set of values $sf_1 \ldots sf_n$ may be selected for a solution at 25° C., a different set of values $sf_1 \ldots sf_n$ may be selected for a second solution differing from the first solution only in that that the second solution is at 35° C. The two sets of values $sf_1 \ldots sf_n$ for the two solutions differing only by temperature may be located in two distinct locations in machine memory 1910.

The system may select values $sf_1 \ldots sf_n$ on the basis of information from Ab output 1927. Information from Ab output 1927 may be used at step 1964.

The information from Ab output 1927 may include Ab structure 1950. Ab structure 1950 may be used in selecting values $sf_1 \ldots sf_n$. For example, for a set of parameters $P_1 \ldots P_n$ selected at step 1962 for an objective function selected at step 1960, values $sf_1 \ldots sf_n$ may depend on sequence 1952; while one set of values $sf_1 \ldots sf_n$ may be selected for an antibody with complete sequence 1954, a different set of values $sf_1 \ldots sf_n$ may be selected for the same antibody with sectional sequence 1956. The two sets of values $sf_1 \ldots sf_n$ for the same antibody with two different sequences 1952 may be located in two distinct locations in machine memory 1910.

At step 1966, the locations of the scaling factors in machine memory 1910 may be identified in accord with the information from BSS output 1931 and/or from Ab output 1927.

At step 1968, the system may retrieve values $sf_1 \ldots sf_n$. Values $sf_1 \ldots sf_n$ may be retrieved from machine memory locations identified at step 1966.

The system may proceed to step 1970. At step 1970, the system may compute values $P_1' \ldots P_n'$ for parameters $P_1 \ldots P_n$, respectively. Values $P_1' \ldots P_n'$ may be computed on the basis of information from Ab output 1927. Information from Ab output 1927 may be used at step 1970. Values $P_1' \ldots P_n'$ may be computed on the basis of information from BSS output 1931. Information from BSS output 1931 may be used at step 1970.

The system may proceed to step 1972. At step 1972, the system may evaluate the objective function. A value of the objective function may be computed on the basis of values $sf_1 \ldots sf_n$ and values $P_1' \ldots P_n'$. The value calculated for the objective function may correspond to a prediction of the value of PC 1928 for Ab 1926 under conditions 1924.

The system may proceed to step 1974. Information from DC output 1959 pertaining to DC 1958 may be used at step 1974. At step 1974, the system may compare the prediction of the value of PC 1928 to DC 1958 to determine whether Ab 1926 under conditions 1924 satisfies DC 1958.

If DC 1958 is satisfied, the system may proceed to step 1976. At step 1976, Ab production may be carried out. Ab production may include fluid transfer of Ab 1926. Ab production may include storage of Ab 1926. Ab production may include manufacture of Ab 1926. Manufacture of Ab 1926 may include engineering a virtual antibody 1926 into a real-world antibody. Ab production may include any steps and activities associated with production of an antibody.

The system may proceed to step 1978 from step 1976. The system may proceed to step 1978 if, at step 1974, DC 1958 is not satisfied.

At step 1978, the system may query whether one or more of the data from BSS output 1931, Ab output 1927, PC output 1929 and/or DC output 1959 is to be reset. For example, while DC 1958 may have been satisfied at step 1974 and Ab 1926 may be currently in production at step 1976, a need may have arisen to produce Ab 1926 at an antibody concentration different from Ab concentration 1942 of the current production; to produce Ab 1926 in a buffer of chemical composition different from composition 1934 of the current production; or to produce an antibody different from Ab 1926 of the current production.

If the response to the query of step 1978 is negative, the system may proceed to end 1980. The system may default to end 1980 in the absence of a response at step 1978 after elapse of some set time or in accord with some other criterion.

If the response to the query of step 1978 is affirmative, the system may proceed to step 1982. At step 1982, a datum or more than one datum of the data from BSS output 1931, Ab output 1927, PC output 1929 and DC output 1958, may be reset. For example, a datum or more than one datum of sequence 1950 may be reset (by, for example: changing a single amino acid residue; shifting the sequence from complete to sectional; replacing Ab 1926 with an antibody substantially different in sequence from Ab 1926); or a datum or more than one datum of concentrations 1936 may be reset (by, for example: changing pH or IS). Similarly, changes may be made in the data pertaining to Ab sub/class 1948, BSS 1930, PC 1928 and DC 1958.

The system may proceed back to step 1920 from step 1982. The data reset at step 1982 may be received at step 1920.

One of ordinary skill in the art will appreciate that the elements of apparatus, media and code shown and described herein may be configured in other than the recited configuration and that one or more of the elements may be optional. One of ordinary skill in the art will appreciate that the steps of processes and methods shown and described herein may be performed in other than the recited order and that one or more steps illustrated may be optional.

Thus, apparatus, methods and media, including computer readable code, for performing one or more of: determining, based on calculated physiochemical characteristics of the antibody, fitness of the antibody for inclusion in the therapeutic agent; selecting, based on calculated physiochemical characteristics of the antibody, among candidate-antibodies for inclusion in the therapeutic agent; and manufacturing of the therapeutic agent based on calculated physiochemical characteristics of the antibody have been provided. Persons skilled in the art will appreciate that the present invention can be practiced by other than the described embodiments, which are presented for purposes of illustration rather than of limitation. The present invention is defined by the claims that follow.

What is claimed is:

1. A method of manufacturing a composition comprising an antibody, the method comprising:
    setting a viscosity limit for the antibody based on a fluid flow resistance of a fluid conducting element in a manufacturing vessel, the fluid flow resistance depending on a viscosity of fluid that flows through the element;
    calculating a net charge and a charge asymmetry using a light chain variable domain (VL) amino acid sequence and a heavy chain variable domain (VH) amino acid sequence of the antibody;
    obtaining for the antibody:
        a first scaling factor that corresponds to the net charge, and
        a second scaling factor that corresponds to the charge asymmetry; and
    determining a predictive index of a viscosity of the antibody using an objective function comprising the scaling factors, the net charge, and the charge asymmetry; and
    responsive to the predictive index being below the viscosity limit, transmitting the antibody through the element for manufacturing the composition.

2. The method of claim 1 wherein the net charge comprises a sum of a net charge of the VL amino acid sequence and a net charge of the VH amino acid sequence.

3. The method of claim 1 wherein the charge asymmetry comprises an arithmetic product of the net charge of the VL amino acid sequence and the net charge of the VH amino acid sequence.

4. The method of claim 1, wherein obtaining the scaling factors comprises:
    determining the scaling factors from data of at least one viscosity measurement of at least one test antibody, and
    wherein the antibody and the test antibody are of the same antibody class.

5. The method of claim 4
    wherein obtaining the scaling factors further comprises:
        determining the scaling factors from data of a plurality of viscosity measurements of the at least one test antibody, each of the viscosity measurements taken under a different solution condition.

6. The method of claim 5 wherein, in the objective function, log 10 of the predictive index comprises the sum of (the net charge X the first scaling factor) plus (the charge asymmetry X the second scaling factor).

7. The method of claim 1, further comprising the steps of:
    calculating from information of one or more complementarity determining regions (CDRs) of the antibody, a hydrophobicity; and
    selecting a third scaling factor that corresponds to the hydrophobicity, wherein the objective function further comprises the third scaling factor.

8. The method of claim 7 wherein the hydrophobicity comprises a total of summation functions of values of hydrophobicity of the one or more CDRs.

9. The method of claim 8 wherein each of the summation functions is a ratio of a sum of values of hydrophobic residues of a CDR and of a sum of values of hydrophilic residues of the CDR.

10. The method of claim 9 wherein the values are Eisenberg hydrophobicity scale values.

11. The method of claim 8 wherein the one or more CDRs comprise one, two, three, four, five or six CDRs.

12. The method of claim 8 wherein the one or more CDRs comprise all six CDRs.

13. The method of claim 1 wherein the antibody is produced according to a method of culturing, under conditions suitable for expressing the antibody, a host cell comprising nucleic acid encoding the antibody.

* * * * *